(12) United States Patent
Chen et al.

(10) Patent No.: US 12,064,425 B2
(45) Date of Patent: Aug. 20, 2024

(54) COMPOSITIONS AND METHODS FOR TARGETING A VIRAL INFECTION

(71) Applicant: THE CHILDREN'S MEDICAL CENTER CORPORATION, Boston, MA (US)

(72) Inventors: Bing Chen, Boston, MA (US); Gary Frey, Boston, MA (US); Tianshu Xiao, Boston, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 250 days.

(21) Appl. No.: 17/262,540

(22) PCT Filed: Jul. 26, 2019

(86) PCT No.: PCT/US2019/043612
§ 371 (c)(1),
(2) Date: Jan. 22, 2021

(87) PCT Pub. No.: WO2020/023849
PCT Pub. Date: Jan. 30, 2020

(65) Prior Publication Data
US 2021/0338659 A1    Nov. 4, 2021

Related U.S. Application Data

(60) Provisional application No. 62/711,143, filed on Jul. 27, 2018.

(51) Int. Cl.
*A61K 31/4709*    (2006.01)
(52) U.S. Cl.
CPC ............................... *A61K 31/4709* (2013.01)

(58) Field of Classification Search
CPC .................................................. A61K 31/4709
See application file for complete search history.

(56) References Cited

U.S. PATENT DOCUMENTS

| | | | |
|---|---|---|---|
| 5,866,562 | A | 2/1999 | Schohe-Loop et al. |
| 7,183,413 | B2 | 2/2007 | Lin et al. |
| 2002/0114769 | A1 | 8/2002 | Rotenberg et al. |
| 2015/0113742 | A1 | 4/2015 | David |

OTHER PUBLICATIONS

Vial, Drug Discovery in Infectious Diseases, vol. 2, Issue: Apicomplexan Parasites, pp. 137-162, 2011. (Year: 2011).*
Panying, Elsevier, Phytomedicine, vol. 36, 2017, pp. 18-25. (Year: 2017).*
Lalezari, N Engl J Med, 348:22, May 2003, 2175-2180. (Year: 2003).*
Woollard, Drug Desigh, Development and Therapy, 5447-5468, DOI: 10.2147/.DDDT.S90580, 2015. (Year: 2015).*
He, J BIo CHem, vol. 283 (17), 11126-11134, Apr. 2008. (Year: 2008).*
Zhang, AIDS Res Ther, 2016, 13:8, 1-4. (Year: 2016).*
Liu, Protein Cell, 2018, vol. 9(7), 596-615. (Year: 2018).*

* cited by examiner

*Primary Examiner* — D Margaret M Seaman
(74) *Attorney, Agent, or Firm* — NIXON PEABODY LLP; David S. Resnick; Jeanne N. Jodoin

(57) ABSTRACT

Described herein are compounds that inhibits the membrane proximal external region (MPER) of a viral envelope (Env), as well as and compositions thereof. Further provided herein are methods for treating or preventing a viral infection comprises administering to a subject in need thereof an agent or compound that inhibits the MPER of a viral Env. In certain embodiments, the viral infection is an HIV infection.

8 Claims, 37 Drawing Sheets
Specification includes a Sequence Listing.

```
┌─────────────────────────────────────┐
│ Structure determination of compounds in │
│        complex with gp41           │
└─────────────────────────────────────┘
                 │
                 ▼
┌─────────────────────────────────────┐
│ Computational chemistry to predict  │
│      and design new compounds       │
└─────────────────────────────────────┘
                 │
                 ▼
┌─────────────────────────────────────┐
│      Sythesis of focused libraries  │
└─────────────────────────────────────┘
                 │
                 ▼
┌─────────────────────────────────────┐
│  FP assay for binding to the gp41 pocket │
└─────────────────────────────────────┘
 $IC_{50} \leq 5$ μM (or previous round) │ No
                 ▼
┌─────────────────────────────────────┐
│ Assays for inhibition of viral infectivity │
│        and for cytotoxicity         │
└─────────────────────────────────────┘
        $IC_{50} \leq 50$ nM │ No
                 ▼
┌─────────────────────────────────────┐
│ Lead compound for further development │
└─────────────────────────────────────┘
                 ▼
┌ ─ ─ ─ ─ ─ ─ ─ ─ ─ ─ ─ ─ ─ ─ ─ ─ ─ ─ ┐
│ Further optimization to improve clinical properties and │
│ test in the nonhuman primate model for HIV-1 inhibition │
└ ─ ─ ─ ─ ─ ─ ─ ─ ─ ─ ─ ─ ─ ─ ─ ─ ─ ─ ┘
```

FIG. 11

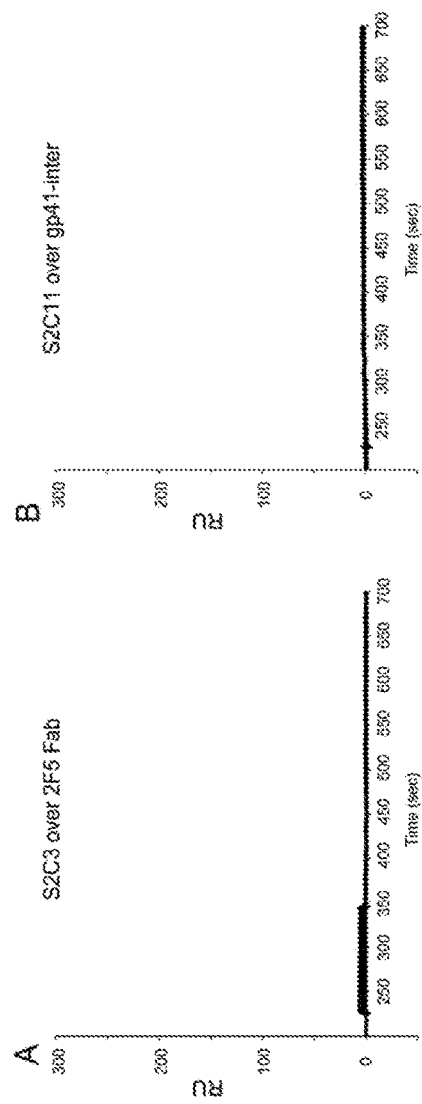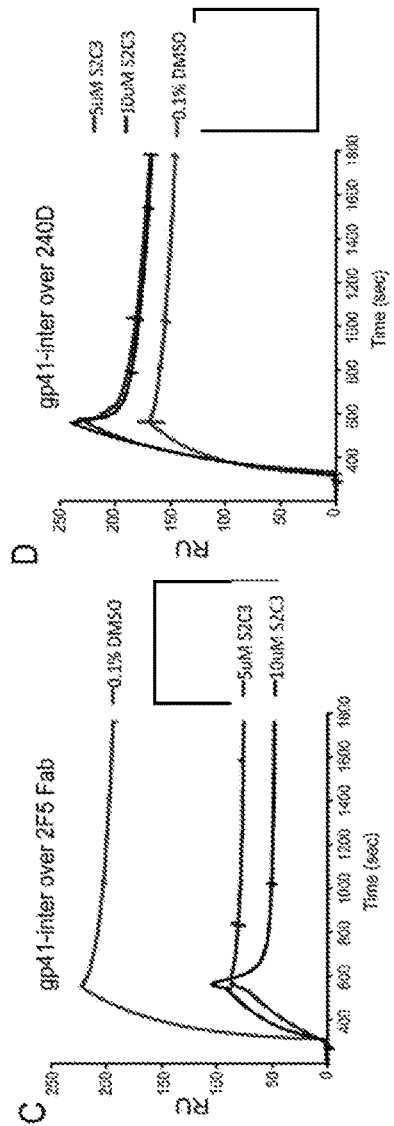
FIG. 16A  FIG. 16B  FIG. 16C  FIG. 16D

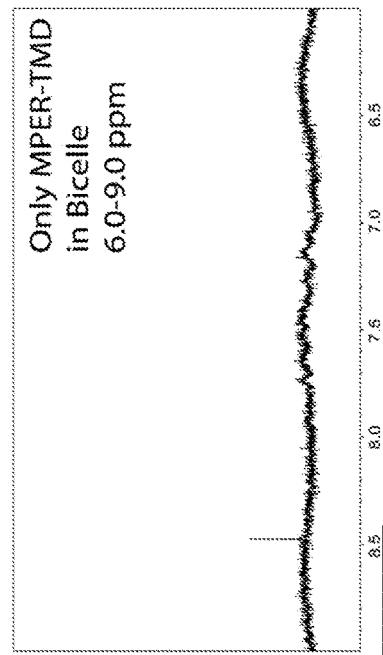
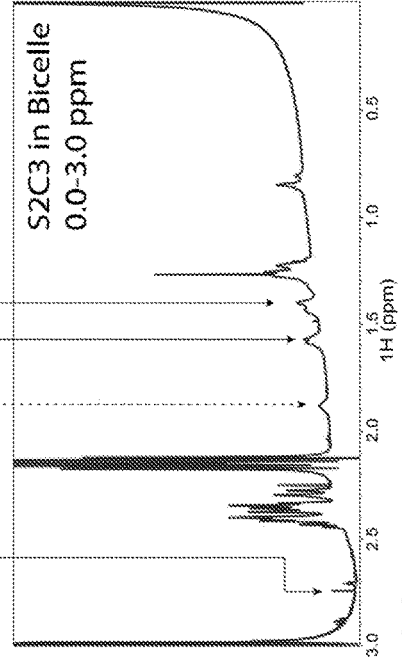
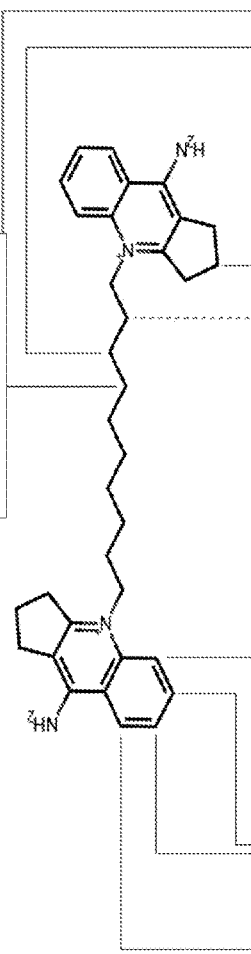
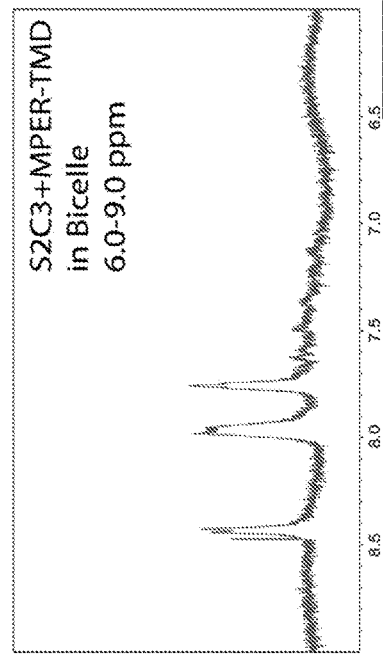
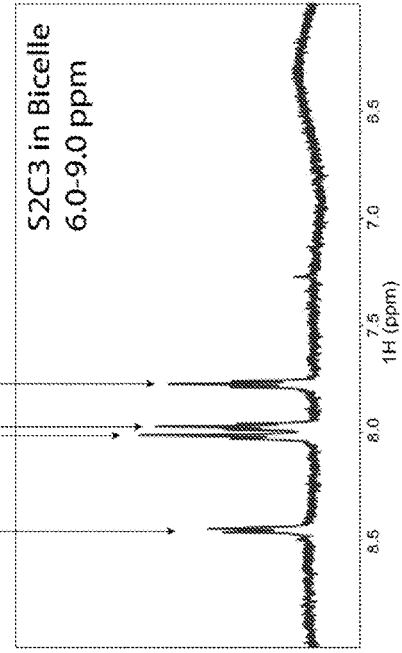
FIG. 20A
FIG. 20B

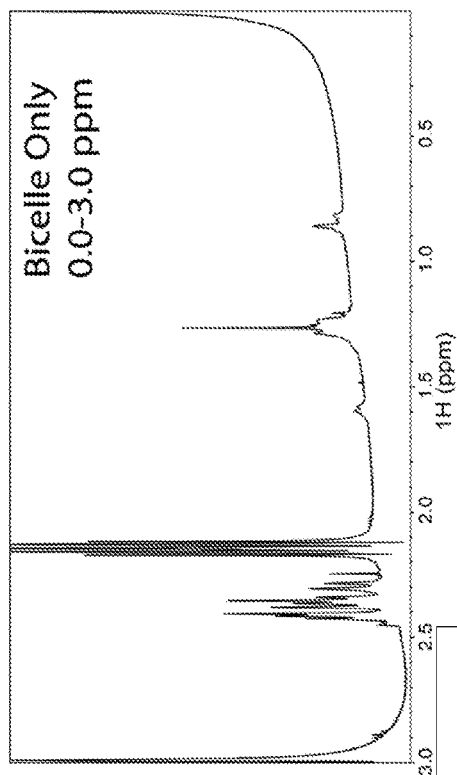
FIG. 20C
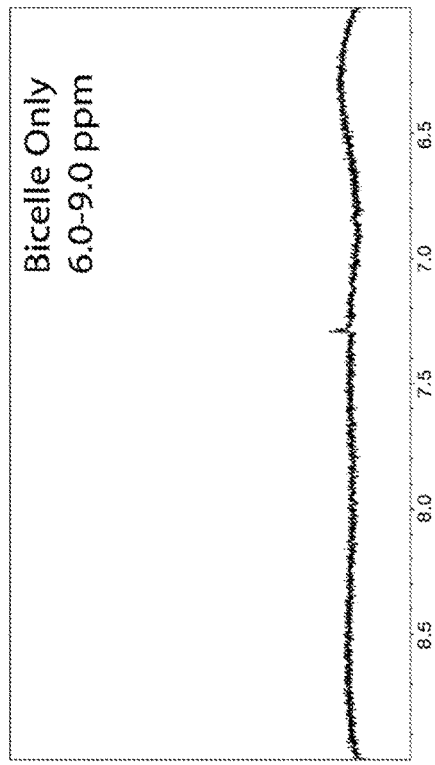
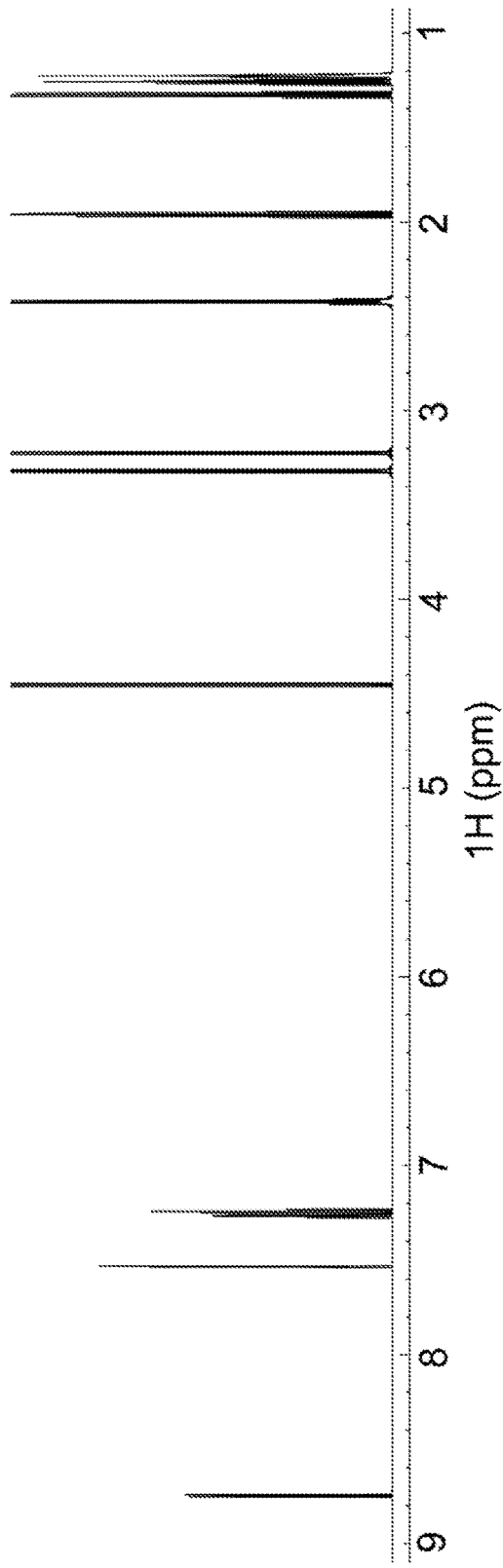
FIG. 20D

COMPOSITIONS AND METHODS FOR TARGETING A VIRAL INFECTION

CROSS-REFERENCE TO RELATED APPLICATIONS

This application is a 371 National Phase Entry of International Patent Application No. PCT/US2019/043612 filed Jul. 26, 2019, which claims benefit under 35 U.S.C. § 119(e) of U.S. Provisional Application No. 62/711,143 filed Jul. 27, 2018, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 29, 2021, is named 701039-093170US-PX_SL.txt and is 19,623 bytes in size.

GOVERNMENT SUPPORT

This invention was made with Government support under Grant numbers AI129721, AI112489, AI141002, AI106488, AI127193 awarded by the National Institutes of Health. The Government has certain rights in the invention.

FIELD OF THE INVENTION

The present disclosure relates to the treatment of a viral infection.

BACKGROUND

Development of anti-Human Immunodeficiency Virus-1 (HIV-1) strategies remains a global health priority as acquired immunodeficiency deficiency syndrome (AIDS) if often fatal. Although it is generally accepted that an effective vaccine is one way to eradicate this devastating disease, currently there are no promising vaccine candidates on the horizon. In developed countries, combination antiretroviral therapy (cART) has transformed this once fatal illness into a manageable chronic condition. The latest cART regimen uses several classes of antiviral therapeutics, including nucleoside/nucleotide reverse transcriptase inhibitors (NRTIs), non-nucleoside reverse transcriptase inhibitors (NNRTIs), protease inhibitors (PIs), fusion inhibitors (FIs), co-receptor inhibitors (CRIs) and integrase inhibitors (INIs). A typical therapy requires a combination of three or more drugs from at least two classes. Drug resistance, severe side effects and difficulties in patient compliance all call for additional drugs and drug targets. The first of its kind fusion inhibitor approved by FDA is Enfuvirtide, a 36-residue peptide derived from gp41. Enfuvirtide is rarely used, however, because of its numerous disadvantages, and it will be necessary to develop next-generation of fusion inhibitors to overcome these limitations. Described herein are small-molecule inhibitors against a novel target, the membrane proximal external region (MPER) of HIV-1 envelope (Env) useful in preventing and/or treating viral infections (e.g., HIV infections).

SUMMARY OF THE INVENTION

The compounds, or compositions or pharmaceutical compositions thereof, and methods described herein are related, in part, to the discovery of small-molecule fusion inhibitors that target the membrane proximal external region (MPER) of HIV-1 envelope (Env) spikes. Accordingly, one aspect of the invention described herein provides a compound of Formula (I):

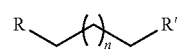

FORMULA (I)

and pharmaceutically acceptable salts thereof,
wherein:
n is an integer from 3 to 14;
R and R' are independently selected from the group consisting of:
(i) Formula (II):

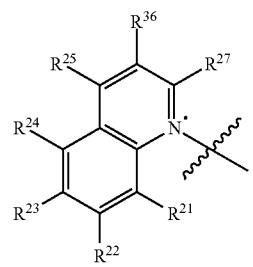

FORMULA (II)

wherein:
$R^{11}$, $R^{12}$, $R^{13}$, and $R^{15}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and
$R^{16}$ and $R^{17}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{26}$ and $R^{27}$, together with the carbon atoms they are attached to, form a 5-8 membered cyclyl, heterocyclyl, aryl or heteryaryl, each of which can be optionally substituted with 1, 2, 3, or more independently selected substituents;
(ii) Formula (III):

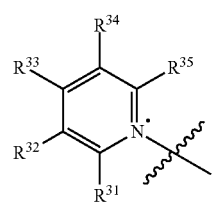

FORMULA (III)

wherein:
$R^{31}$, $R^{32}$ and $R^{33}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and $R^{34}$ and $R^{135}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{34}$ and $R^{35}$, together with the carbon atoms they are attached to, form a 5-8 membered cyclyl, heterocyclyl, aryl or heteryaryl, each of which can be optionally substituted with 1, 2, 3, or more independently selected substituents; and pharmaceutically acceptable salts thereof; and (iii) Formula (IV):

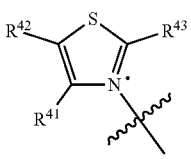

FORMULA (IV)

wherein:

$R^{41}$, $R^{42}$, and $R^{43}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl, and provided that compound is not dequalinium.

In one embodiment of any aspect described herein, n is 6, 8 or 10.

In another embodiment of any aspect described herein, R and R' are independently of Formula (III).

In another embodiment of any aspect described herein, R and R' are the same.

In another embodiment of any aspect described herein, $R^{21}$, $R^{22}$, $R^{23}$, $R^{24}$, and $R^{25}$ are independently selected form the group consisting of H, alkyl, haloalkyl, hydroxyl, alkoxy, amino, alkylamino, dialkylamino, carboxyl, halogen, nitro, cyano, thiol, and thiolalkoxy; and $R^{26}$ and $R^{27}$ are independently selected form the group consisting of H, alkyl, haloalkyl, hydroxyl, alkoxy, amino, alkylamino, dialkylamino, carboxyl, halogen, nitro, cyano, thiol, and thiolalkoxy, or R26 and $R^{27}$, together with the carbon atoms they are attached to, form a 4-8 membered cyclyl.

In another embodiment of any aspect described herein, $R^{21}$, $R^{22}$, $R^{23}$, $R^{24}$, and $R^{25}$ are independently selected form the group consisting of H, halogen, C1-C6alkyl, halo(C1-C6)alkyl, amino, C1-C-6alkylamino, or di(C1-C-6alkyl) amino; and $R^{26}$ and $R^{27}$ are independently selected form the group consisting of H, halogen, C1-C6alkyl, halo(C1-C6) alkyl, amino, C1-C-6alkylamino, or di(C1-C-6alkyl)amino, or $R^{26}$ and $R^{27}$, together with the carbon atoms they are attached to, form a 5-membered cyclyl.

In another embodiment of any aspect described herein, $R^{21}$, $R^{22}$, $R^{23}$ and $R^{24}$ are independently selected form the group consisting of H and halogen; $R^{25}$ is selected from the group consisting of H and amino; and $R^{26}$ and $R^{27}$ are independently selected form the group consisting of H and halogen, or $R^{26}$ and $R^{27}$, together with the carbon atoms they are attached to, form a 5-membered cyclyl.

In another embodiment of any aspect described herein, the compound is selected from the group consisting of:

R and R' are the same; $R^{21}$, $R^{22}$, $R^{23}$, and $R^{24}$ are H; $R^{25}$ is amino; $R^{26}$ and $R^{27}$, together with the carbon atoms they are attached to form a 5-membered cyclyl; and n is 4, 6, 8, 10;

R and R' are the same; $R^{21}$, $R^{22}$, $R^{23}$, $R^{24}$ and $R^{26}$ are H; $R^{25}$ is amino; $R^{27}$ is methyl; and n is 4, 6, 8, 10 or 12;

R and R' are the same; $R^{21}$, $R^{22}$, $R^{23}$, $R^{24}$, $R^{26}$, and R27 are H; $R^{25}$ is amino; and n is 4, 6, 8, 10;

R and R' are the same; $R^{21}$, $R^{23}$, $R^{24}$, $R^{26}$ and $R^{27}$ are H; $R^{22}$ is halogen, e.g., Cl; $R^{25}$ is amino; and n is 4, 6, 8, 10;

R and R' are the same; $R^{21}$, $R^{22}$; $R^{24}$, $R^{26}$ and $R^{27}$ are H; $R^{23}$ is halogen, e.g., Br; $R^{25}$ is amino; and n is 4, 6, 8, 10;

R and R' are the same; $R^{21}$, $R^{22}$, $R^{23}$, $R^{24}$, and $R^{27}$ are H; $R^{26}$ is halogen, e.g., Br; $R^{25}$ is amino; and n is 4, 6, 8, 10; and R and R' are the same; $R^{21}$, $R^{22}$; $R^{23}$, $R^{24}$, $R^{25}$, $R^{26}$ and $R^{27}$ are H; and n is 4, 6, 8, 10.

In another embodiment of any aspect described herein, the compound is selected from the group consisting of:

Compound S2C3, where R and R' are the same; $R^{21}$, $R^{22}$, $R^{23}$ and $R^{24}$ are H; $R^{25}$ is amino; $R^{26}$ and , $R^{27}$, together with the carbon form they are attached to form a 5-membered cyclyl; and n is 8;

Compound S1C1, where R and R' are the same; $R^{21}$, $R^{22}$, $R^{23}$, $R^{24}$ and $R^{26}$ are H; $R^{25}$ is amino; $R^{27}$is methyl; and n is 4;

Compound S1C4, where R and R' are the same; $R^{21}$, $R^{22}$, $R^{23}$, $R^{24}$ and $R^{26}$ are H; $R^{25}$ is amino; $R^{27}$ is methyl; and n is 10;

Compound S1C5, where R and R' are the same; $R^{21}$, $R^{22}$, $R^{23}$, $R^{24}$ and $R^{26}$ are H; $R^{25}$ is amino; is methyl; and n is 12;

Compound S2C1, where R and R' are the same; $R^{21}$, $R^{22}$, $R^{23}$, $R^{24}$, $R^{26}$ and $R^{27}$ are H; $R^{25}$ is amino; and n is 8;

Compound S2C6, where R and R' are the same; $R^{21}$, $R^{23}$, $R^{24}$, $R^{26}$ and $R^{27}$ are H; $R^{22}$ is Cl; $R^{25}$ is amino; and n is 8;

Compound S2C7, where R and R' are the same; $R^{21}$, $R^{22}$, $R^{24}$, $R^{26}$ and $R^{27}$ are H; $R^{23}$ is Br; $R^{25}$ is amino; and n is 8;

Compound S2C8, where R and R' are the same; $R^{21}$, $R^{22}$, $R^{23}$, $R^{24}$ and $R^{27}$ are H; $R^{26}$ is Br; $R^{25}$, is amino; and n is 8;

Compound S2C10, where R and R' are the same; $R^{21}$, $R^{22}$, $R^{23}$, $R^{24}$, $R^{25}$, $R^{26}$ and , $R^{27}$ are H; and n is 8;

Compound S1C2, where R and R' are the same; $R^{21}$, $R^{22}$, $R^{23}$, $R^{24}$ and $R^{26}$ are H; $R^{25}$ is amino, is methyl; and n is 6;

Compound S2C9, where R and R' are the same; $R^{31}$, $R^{32}$ and $R^{34}$ are H; $R^{33}$ is $NH_2$; and $R^{35}$ is methyl; and Compound S2C11, where R and R' are the same; $R^{41}$ is methyl; $R^{42}$ is ethyl; and $R^{43}$ is H.

Another aspect described herein provides a composition comprising any of the compounds describe herein.

In one embodiment of any aspect described herein, the composition further comprises a pharmaceutically acceptable carrier.

Another aspect described herein provides a pharmaceutical composition comprising any of the compounds described herein.

Yet another aspect described herein provides a method of treating or preventing a viral infection comprising administering to a subject in need thereof any of the compounds, any of the compositions, or the any of the pharmaceutical compositions described herein.

Another aspect described herein provides a method of treating or preventing a viral infection comprising administering to a subject in need thereof an agent that inhibits the membrane proximal external region (MPER) of a viral envelope (Env).

In one embodiment of this aspect or any other aspect, the subject is a mammal. In another embodiment of this aspect or any other aspect, the subject is a human.

In another embodiment of this aspect or any other aspect, the viral infection is a Human Immunodeficiency Virus (HIV-1) infection or HIV-2 infection. In another embodiment of this aspect or any other aspect, the viral infection results in acquired immune deficiency syndrome (AIDS).

In another embodiment of this aspect or any other aspect, the viral Env is HIV-1 Env or HIV-2 Env.

In another embodiment of this aspect or any other aspect, the HIV-1 infection is resistant to an inhibitor of HIV-1 fusion to a target cell. Exemplary target cells include, but are not limited to, a mammalian cell, a human cell, a leukocyte, a lymphocyte, a T cell, or a CD4+ T cell. Exemplary inhibitors of HIV fusion to a target cell include, but are not limited to Maravirox, Enfuvirtide, Sifuvirtide, or Albuvirtide.

In another embodiment of this aspect or any other aspect, the HIV-1 or HIV-2 infection is resistant to at least one HIV treatment. Exemplary HIV treatments include, but are not limited to those listed in Table 1.

In one embodiment of this aspect or any other aspect, the agent is any of the compounds described herein, or any of the composition or pharmaceutical compositions described herein.

In one embodiment of this aspect or any other aspect, the agent that inhibits the viral Env is selected from the group consisting of a small molecule, an antibody reagent, a peptide, a genome editing system, an antisense oligonucleotide, and an RNAi.

In another embodiment of this aspect or any other aspect, the small molecule is dequalinium.

In another embodiment of this aspect or any other aspect, the small molecule is a derivative of dequalinium. Exemplary derivatives of dequalinium include, but are not limited to, Analog 1, Analog 2, Analog 3, Analog 4, 4-aminoquinaldine, C800, S1C1, S1C2, S1C4, S1C5, S2C1, S2C3, S2C6, S2C8, S2C9, S2C10, and S2C11.

In another embodiment of this aspect or any other aspect, the small molecule is a derivative of S2C3.

In another embodiment of this aspect or any other aspect, the small molecule is a derivative of C800.

In another embodiment of this aspect or any other aspect, the RNAi is a microRNA, an siRNA, or a shRNA.

In another embodiment of this aspect or any other aspect, inhibiting MPER results in the inhibition of Env fusion to the target cell.

In another embodiment of this aspect or any other aspect, the fusion to the target cell is inhibited by at least 50%, at least 60%, at least 70%, at least 80%, at least 90%, or more as compared to an appropriate control.

Another aspect described herein provides a method of treating or preventing a human immunodeficiency virus (HIV) infection comprising administering to a subject in need a compound or agent as described herein, or a composition or pharmaceutical composition thereof as described herein that inhibits the membrane proximal external region (MPER) of a viral envelope (Env).

Another aspect described herein provides a method of inhibiting Env fusion to a target cell comprising contacting a target cell with a compound or agent as described herein, or a composition or pharmaceutical composition thereof as described herein that inhibits the membrane proximal external region (MPER) of a viral envelope (Env).

Another aspect described herein provides a method of treating a viral infection comprising (a) diagnosing a subject as having a viral infection, and (b) administering to the subject having a viral infection a compound or agent as described herein, or a composition or pharmaceutical composition thereof as described herein that inhibits the membrane proximal external region (MPER) of a viral envelope (Env).

Another aspect described herein provides a method of treating a viral infection comprising (a) receiving the results of an assay that diagnoses a subject as having a viral infection, and (b) administering to the subject having a viral infection a compound or agent as described herein, or a composition or pharmaceutical composition thereof as described herein that inhibits the membrane proximal external region (MPER) of a viral envelope (Env).

Another aspect described herein provides a method of preventing a viral infection comprising (a) diagnosing a subject as being at risk for having a viral infection, and (b) administering to the subject having a viral infection a compound or agent as described herein, or a composition or pharmaceutical composition thereof as described herein that inhibits the membrane proximal external region (MPER) of a viral envelope (Env).

Another aspect described herein provides a method of treating a viral infection comprising (a) receiving the results of an assay that diagnoses a subject as being at risk for having a viral infection; and (b) administering to the subject having a viral infection a compound or agent as described herein, or a composition or pharmaceutical composition thereof as described herein that inhibits the membrane proximal external region (MPER) of a viral envelope (Env).

Yet another aspect descibrd herein provides composition comprising any of the agents described herein.

Another described herein provides a method of identifying a test agent that modulates the activity of MPER of a viral envelope (Env), the method comprising: (a) contacting a glycoprotein 41 (gp41) or fragment thereof with a test agent; (b) contacting the gp41 or fragment thereof with an antibody or fragment thereof that specifically binds to the MPER; and (c) detecting a contact level between the antibody and the MPER; wherein a change in the contact level relative to a control or reference level indicates that the agent modulates the MPER.

In some embodiments of any aspect, the antibody is 2F5, 4E10, Z13e1 or 10E8.

In some embodiments of any aspect, the antibody further comprises a label. In some embodiments of any aspect, the label is a heterologous protein. In some embodiments of any aspect, the heterologous protein is a tag, such as a fluorescent protein.

In some embodiments of any aspect, the detecting comprises analyzing the gp41 contacted in steps (a) and (b) using a fluorescent polarization assay, and wherein a change in the fluorescent polarization signal relative to a control or reference level indicates that the agent modulates the activity of MPER.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

As used herein, the terms "treat," "treatment," or "treating," refer to therapeutic treatments, wherein the object is to reverse, alleviate, inhibit, slow down or stop the progression or severity of a condition associated with a viral infection, e.g., HIV-1 infection. The term "treating" includes reducing or alleviating at least one adverse effect or symptom of a viral infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). Symptoms and clinical markers of a viral infection are further described herein below.

As used herein, the term "prevent" or "preventing" refers to the prevention of at least one symptom associated with a viral infection, or complete prevention of a viral infection, or the lessening of the severity of a viral infection (e.g., preventing the progression of a viral infection) in a subject, and/or delaying one or more symptoms of a viral infection, and/or delaying the onset of a viral infection and/or symptoms following exposure to a virus.

As used herein, the term "administering" refers to the placement of a therapeutic (e.g., a compound or agent that inhibits the MPER, for example, of HIV-1 Env), or composition or pharmaceutical composition thereof as disclosed herein into a subject by a method or route which results in at least partial delivery of the agent to the subject. Compositions and pharmaceutical compositions comprising therapeutics (e.g., a compound or agent that inhibits the MPER, for example, of HIV-1 Env) as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., HIV-1 infection or AIDS model. A subject can be male or female.

A subject can be one who has been previously diagnosed with or identified as suffering from or having a disease or disorder in need of treatment (e.g., HIV infection) or one or more complications related to such a disease or disorder, and optionally, have already undergone treatment for the disease or disorder or the one or more complications related to the disease or disorder. A subject can be resistant to at least one treatment for the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, an "agent" refers to e.g., a molecule, protein, peptide, antibody, or nucleic acid, that inhibits activity of a polypeptide or polynucleotide, or binds to, partially or totally blocks stimulation, decreases, prevents, delays activation, inactivates, desensitizes, or down regulates the activity of the polypeptide or the polynucleotide. Agents that inhibit MPER, e.g., inhibit expression, e.g., translation, post-translational processing, stability, degradation, dissociation, or localization of a polypeptide, or transcription, post transcriptional processing, stability or degradation of a polynucleotide or bind to, partially or totally block stimulation, nucleotide binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans.

As used herein, an "inhibitor" refers to any agent, compound, or composition that reduces the levels or activity of MPER of a viral envelope.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% , or more. As used herein, "reduction" or "inhibition" does not encompass a complete inhibition or reduction as compared to a reference level. "Complete inhibition" is a 100% inhibition as compared to an appropriate control.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a viral infection or prior to receiving a given treatment, or a biological sample that has not been contacted with an agent disclosed herein).

As used herein, an "appropriate control" refers to an untreated, otherwise identical cell or population (e.g., a subject who was not administered an agent described herein, or was administered by only a subset of agents described herein, as compared to a non-control cell).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

BRIEF DESCRIPTION OF THE DRAWINGS

FIGS. 1A-1B show HIV-1 Env and viral entry. FIG. 1A shows a schematic representation of HIV-1 gp160. Segments of gp120 and gp41 are designated as follows: C1-05, conserved regions 1-5; V1-V5, variable regions 1-5; F, fusion peptide; HR1, heptad repeat 1; C-C loop, the immunodominant loop with a conserved disulfide bond; HR2, heptad repeat 2; MPER, membrane proximal external region; TM, transmembrane anchor; CT, cytoplasmic tail. Tree-like symbols represent glycans. FIG. 1B shows membrane fusion by HIV-1 Env likely proceeds stepwise as follows. 1) Binding of gp120 to the receptor CD4 and coreceptor CXCR4 or CCR5; 2) formation of the pre-hairpin intermediate; 3) gp41 folding back and bringing the two membranes together; 4) fusion pore formation.

FIGS. 2A-2C show the design of gp41-inter. FIG. 2A Designation of gp41 segments in various colors. HR1 heptad repeat 1; C-C loop, the immunodominant loop with a conserved disulfide bond; HR2 heptad repeat 2; Fd, foldon, is a trimerization tag. The linker is a short, flexible connector of serines and glycines. Segments of gp41 are designated as in FIG. 1A. FIG. 2B shows a schematic of 3D organization of gp41-inter showing HR2 peptide- and foldon tag-trapped gp41 in the prehairpin intermediate conformation. FIG. 2C shows the proposed prehairpin intermediate state during membrane fusion.

FIGS. 3A-3C show a fluorescence polarization assay for antibody binding to gp41-inter. FIG. 3A shows a diagram illustrating that fluorescent Fab fragment can bind to gp41-inter. F, FITC. FIG. 3B shows fluorescence anisotropy binding curve for the association of 2F5 Fab with gp41-inter. The fraction bound, f, is plotted as a function of gp41-inter concentration (in nM), at a constant concentration of 2F5 (50 nM). $K_D$ is 12 nM. FIG. 3C shows data for 4E10 Fab binding to gp41-inter. $K_D$ is 23 nM for this interaction.

FIG. 4 shows HIV-1 Env mediated cell-cell fusion detected by α-complementation of the β-galactosidase. The α fragment of β-galactosidase is co-expressed with Env and its ω fragment co-expressed as an inactive dimer with CD4 and $CCR^5$. After cell-cell fusion, the dimeric ω fragment assembles into a tetramer in the presence of the α fragment, regaining the activity, which is quantified with a chemiluminescent substrate.

FIGS. 5A-5E show that dequalinium specifically inhibits HIV-1 Env mediated cell-cell fusion. FIG. 5A shows Dequalinium was analyzed in the β-galactosidase-based cell-cell fusion assay using both HIV-1 and SIV Envs. Cytotoxicity was tested by the CELLTITER-GLO 2.0 ASSAY® (Promega). Relative lum, relative luminescence. FIG. 5B shows Dequalinium at 50 µM inhibited cell-cell fusion mediated by Envs from HIV-1 primary isolates of Glade A, B, C and AG. FIG. 5C shows SPR analysis of dequalinium binding to gp41-inter (left) and 2F5 Fab (right). FIG. 5D shows Dequalinium structure. FIG. 5E Inhibition of viral infectivity by dequalinium. X1254-3, BaL.26 and DJ263.8A are HIV-1 isolates; MuLV is a control.

FIG. 6 shows C800 inhibits HIV-1 Env mediated cell-cell fusion. C800 was analyzed in the cell-cell fusion assay using both HIV-1 and SIV Envs. Cytotoxicity measuring the amount of ATP is shown.

FIGS. 7A-7D show the preliminary structure of dequalinium in complex with the MPER-TMD. FIG. 7A (top) shows strips from the 3D 15N-edited NOESY-TROSY spectrum recorded using the 15N-, 2H-labeled MPER-TMD protein in the presence of 3 mM dequalinium. Bottom, 1D proton spectrum of 3 mM dequalinium in the same bicelles. FIG. 7B Strips from the 3D 15N-edited NOESY-TROSY spectrum recorded using the 15N-, 2H-labeled MPER-TMD protein. The acyl chains of the bicelles are also perdeuterated. The protein-dequalinium NOE peaks in the strips in A were identified in the 1D spectrum of dequalinium, as indicated by arrows. FIG. 7C-7D shows top and side views of a preliminary NMR structure of the dequalinium-MPER complex. The ensemble of the compound in complex with the MPER-TMD were generated by Xplor-NIH® software. Ten structures with the lowest energy were selected among 120 structures. FIG. 7D shows the lipid bilayer is indicated by gray lines schematically.

FIGS. 8A-8B show SAR studies of dequalinium and C800. FIG. 8A shows five dequalinium analogs were analyzed in the cell-cell fusion assay. Four compounds (analog 1-4) have different headgroups while 4-aminoquinaldine contains only the dequalinium headgroup. FIG. 8B shows C800 is shown with three representatives of inactive C800 analogs.

FIGS. 9A-9C shows a structure-activity relationship (SAR) study using custom-synthesized dequalinium analogs. FIG. 9A shows the design of five compounds with varying length of the linker of 6, 8, 10, 12, 14 carbons. The 10-carbon-linker compound is dequalinium. FIG. 9B shows the design of 11 dequalinium analogs with different head groups. FIG. 9C shows the first batch of compounds analyzed in the cell-cell fusion assay and the cytotoxicity assay. Cytotoxicity relative to dequalinium at 50 micromolar (µM) was indicated in parenthesis for each compound, with S1C5 being the most toxic and S1C1, S1C2 and S2C10 the least toxic. Membrane fusion activity was normalized by the cytotoxicity. DEQ, dequalinium. Labels on the right are in the order of the lines in graph, from top to bottom.

FIG. 11 shows a flow diagram of compound optimization.

Figure 12A:
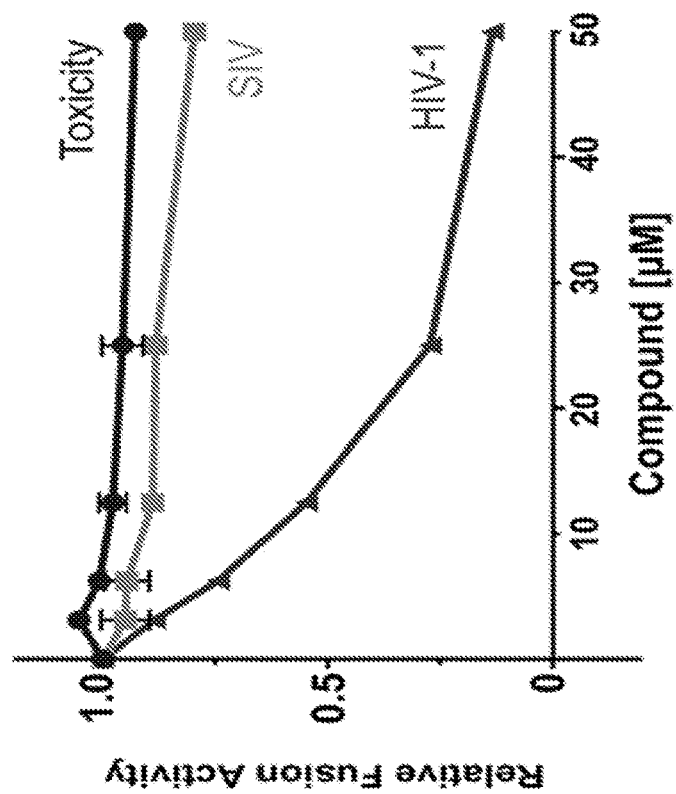
Figure 12B:
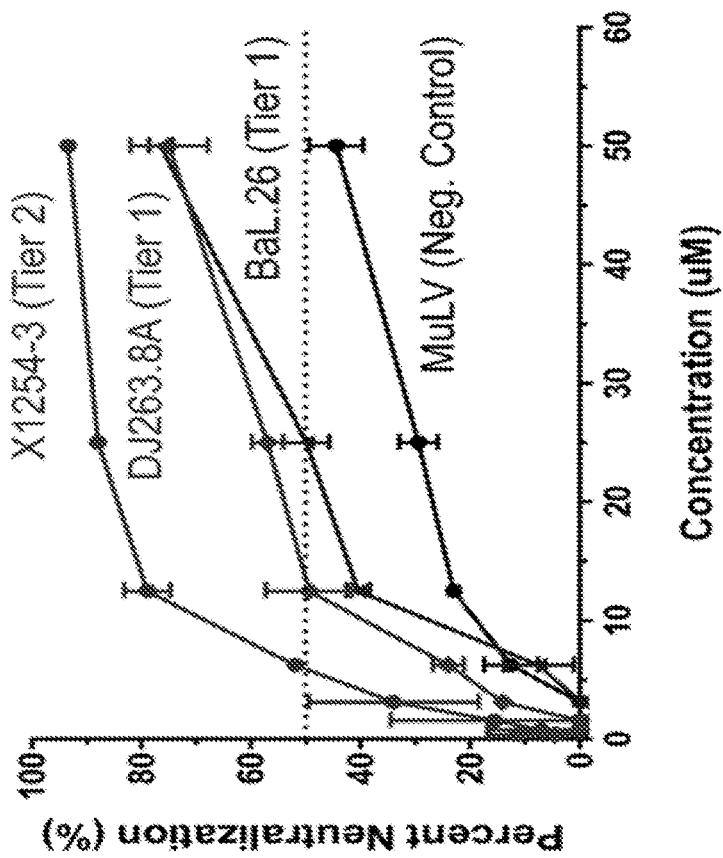

FIG. 12A-12B shows the identification of dequalinium as a small-molecule fusion inhibitor targeting the MPER of HIV-1 Env. FIG. 12A shows that dequalinium was analyzed in the β-galactosidase-based cell-cell fusion assay using both HIV-1 (bottom) and SIV (middle) Envs (ref). Cytotoxicity (top) was tested by the CellTiter-Glo 2.0 Assay (Promega). Relative lum, relative luminescence. FIG. 12B shows inhibition of viral infectivity by dequalinium. BaL.26 and DJ263.8A are HIV-1 tier 1 isolates and X1254-3 is a tier 2 isolate; MuLV is a control. See also FIG. 4 and FIGS. 5A-5E.

Figure 13:
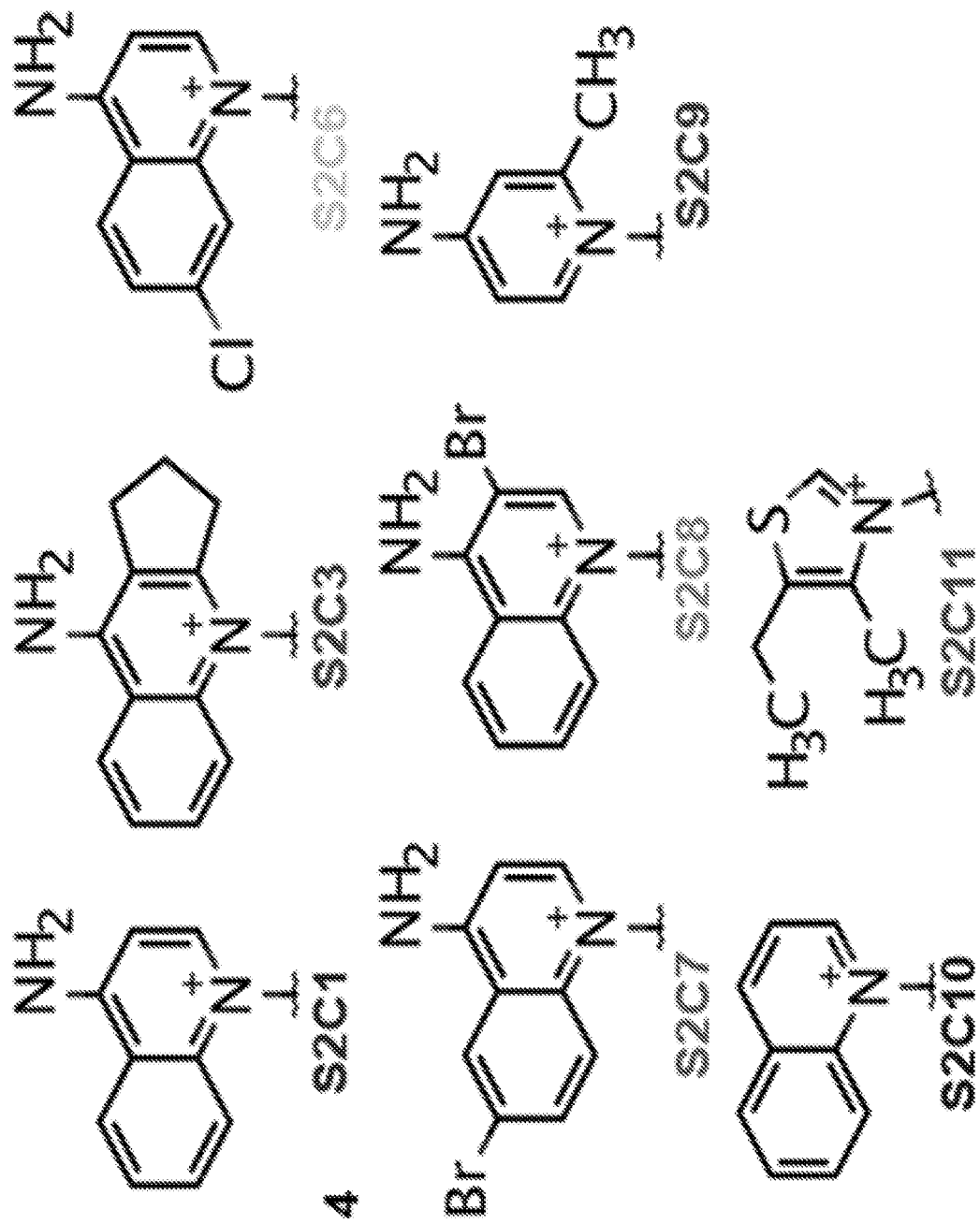

FIG. 13 shows the design of 8 dequalinium analogs with different head groups. See also FIGS. 9A-9C.

Figures 14A, 14B:
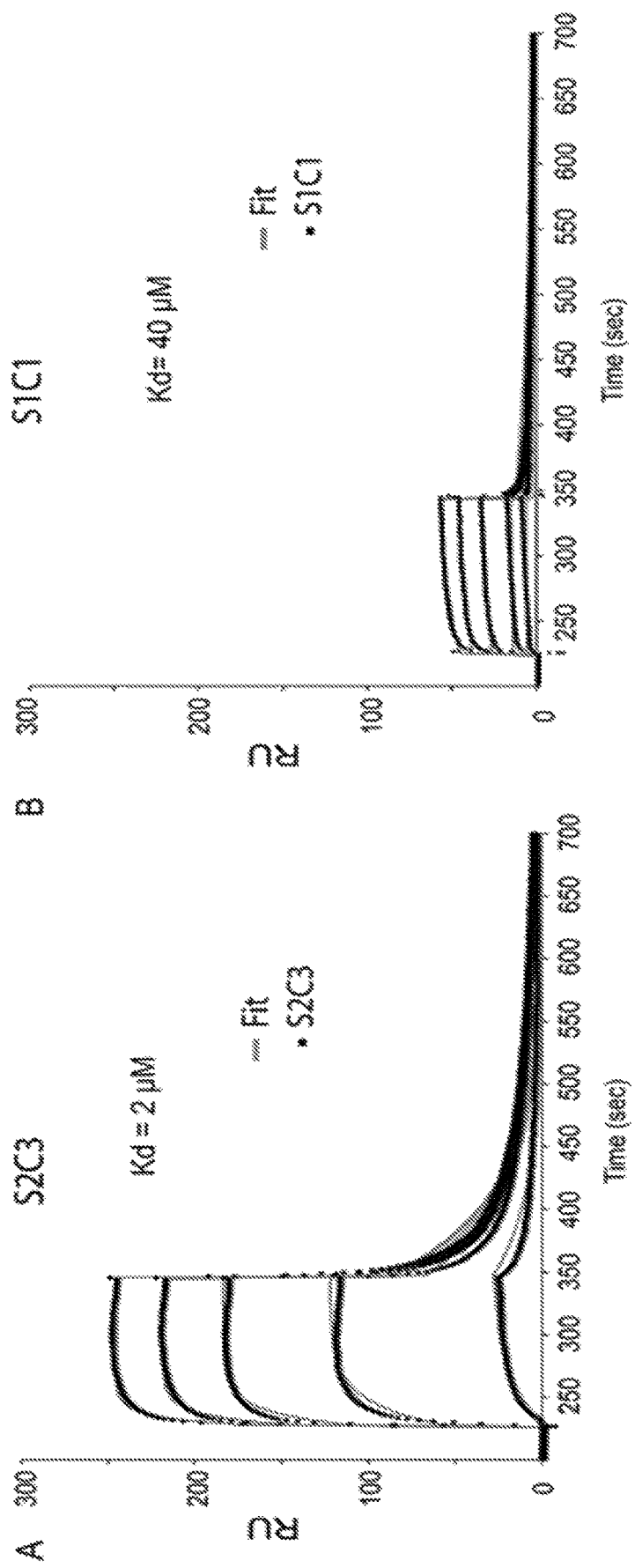
Figures 14C, 14D:
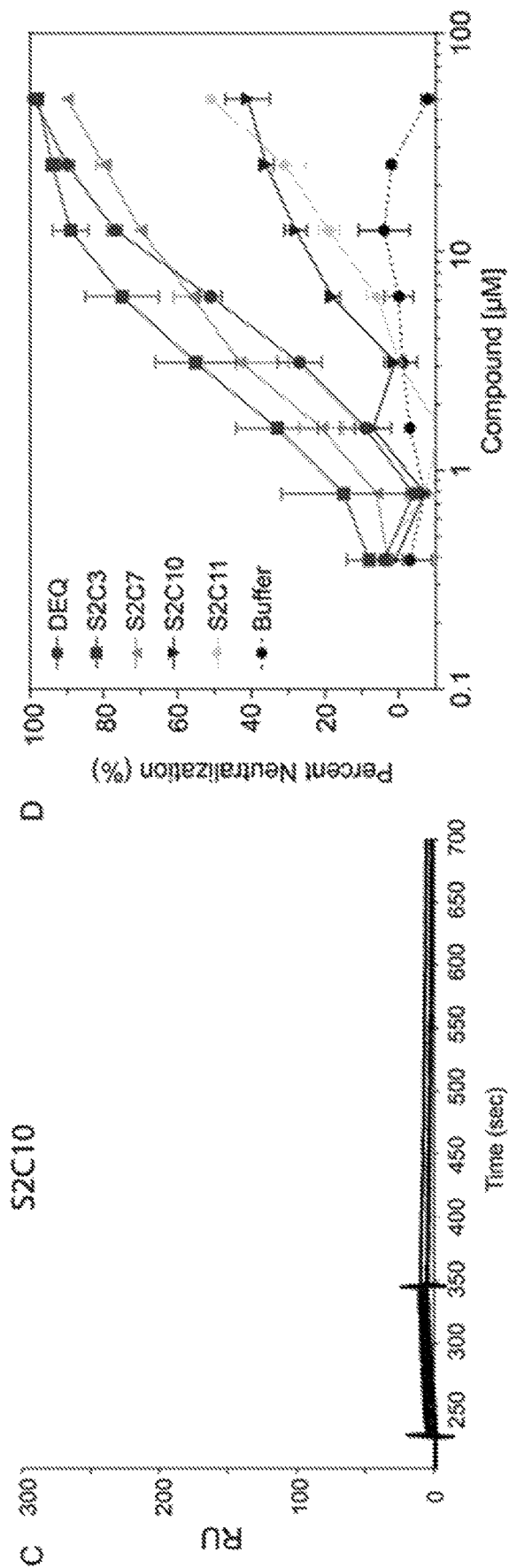

FIG. 14A-14D shows characterization of the most potent compound S2C3. FIG. 14A shows SPR analysis of S2C3 binding to gp41-inter. The protein was immobilized on a CM-5 chip and various concentrations (2-20 µM) of S2C3 were passed over the chip surface. Binding kinetics was evaluated using a 1:1 Langmuir binding model. The sensorgrams are shown in black and the fits in gray. FIG. 14B and FIG. 14C show similar to (FIG. 14A), two weak compounds S1C1 and S2C10 were tested for binding to gp41-inter by SPR. FIG. 14D shows comparison of inhibition of viral infectivity by dequalinium and S2C3. X1254-3 is an HIV-1 isolate; MuLV is a control.

Figure 15A:
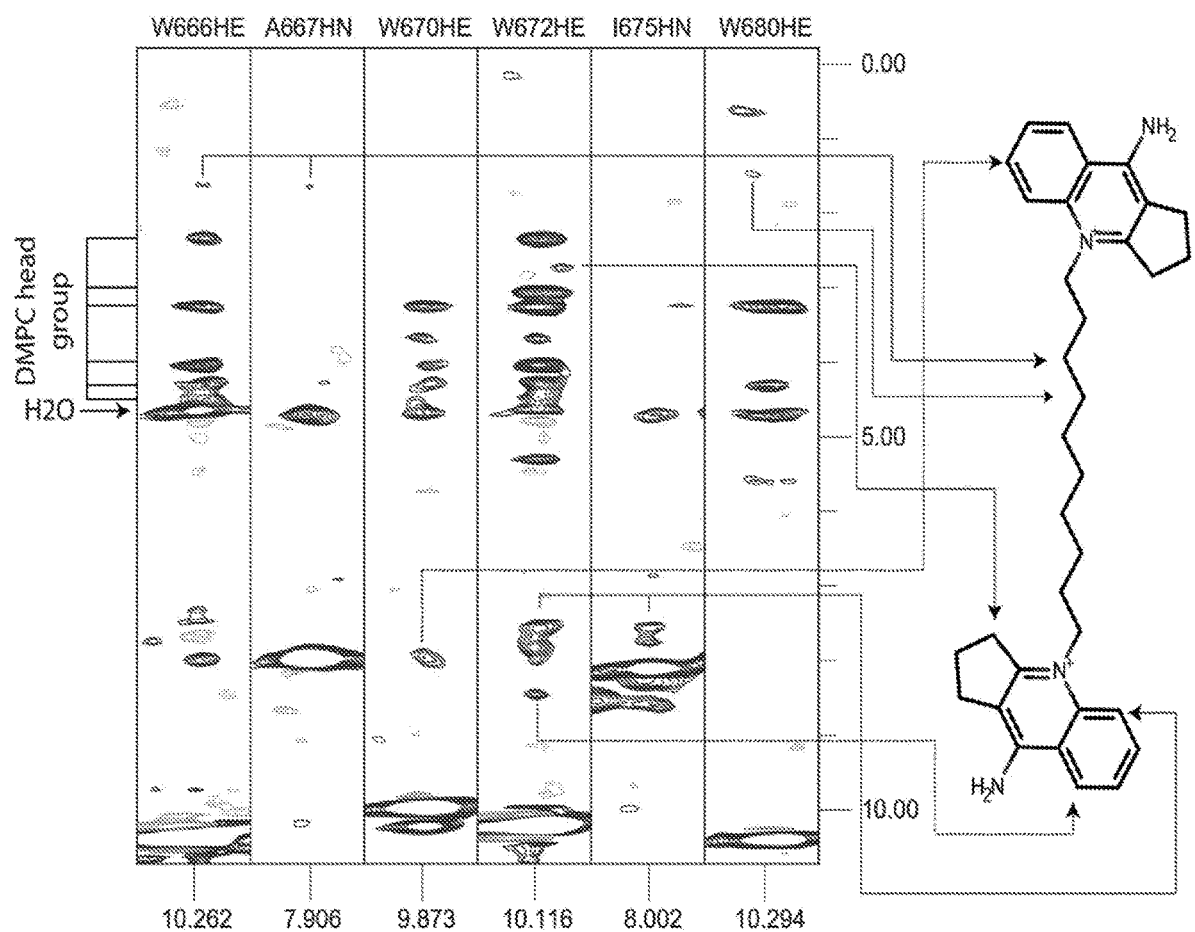
Figure 15B:
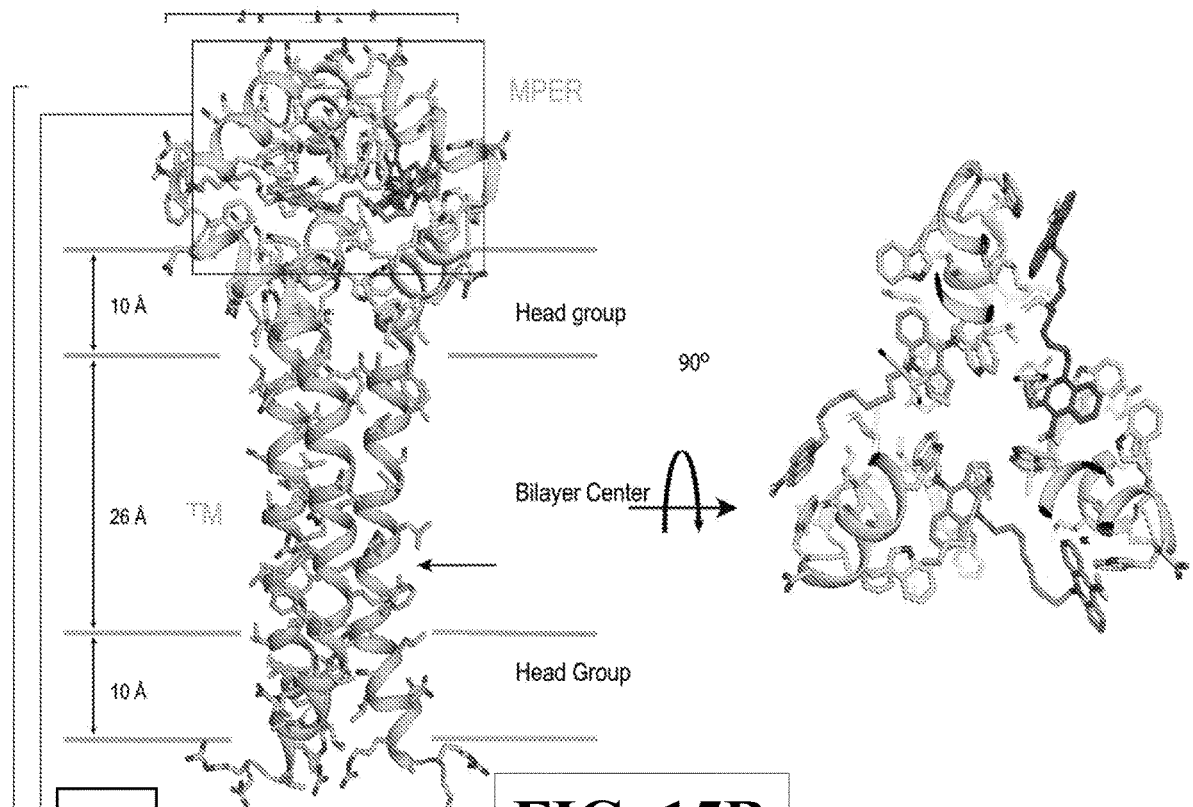
Figure 15C:
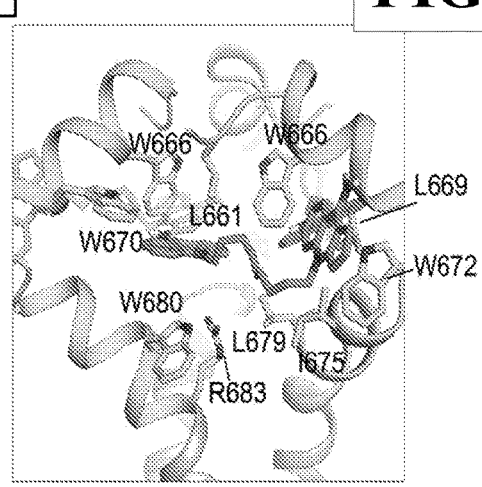
Figure 15D:
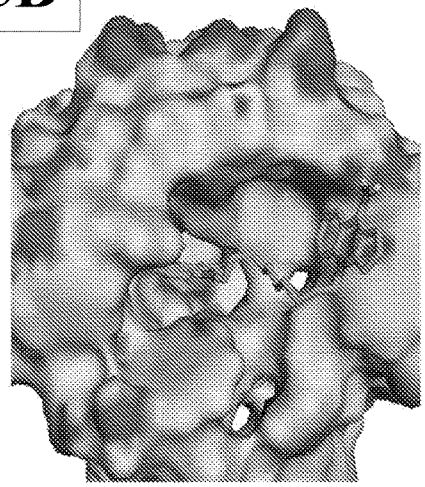

FIG. 15A-15D shows the structure of S2C3 in complex with the MPER-TMD. FIG. 15A shows strips from the 3D $^{15}$N-edited NOESY-TROSY spectrum recorded using the $^{15}$N-, $^2$H-labeled MPER-TMD protein. The acyl chains of the bicelles are also perdeuterated. The protein-S2C3 NOE peaks in the strips were identified in the 1D spectrum of dequalinium, as indicated by arrows. FIG. 15B shows Side and top views of the NMR structure of the S2C3-MPER complex. The ensemble of the compound in complex with the MPER-TMD were generated by Xplor-NIH software[46]. 10 structures with the lowest energy were selected among 120 structures. The lipid bilayer is indicated by gray lines schematically. FIG. 15C and FIG. 15D show a close-up view of the hydrophobic binding pocket of S2C3 formed by residues in the MPER in ribbon diagram and surface representation, respectively.

FIG. 16A-16D shows SPR analysis showing S2C3 interfering with gp41-inter binding with 2F5. FIG. 16A shows S2C3 over 2F5 Fab. FIG. 16B shows S2C1 over gp41-inter. FIG. 16C shows gp41-inter over 2F5 Fab in the presence of 0.1% DMSO, 5 µM S2C3, or 10 µM S2C3. FIG. 16D shows gp41-inter over 240D in the presence of 0.1% DMSO, 5 µM S2C3, or 10 µM S2C3.

Figure 17B:
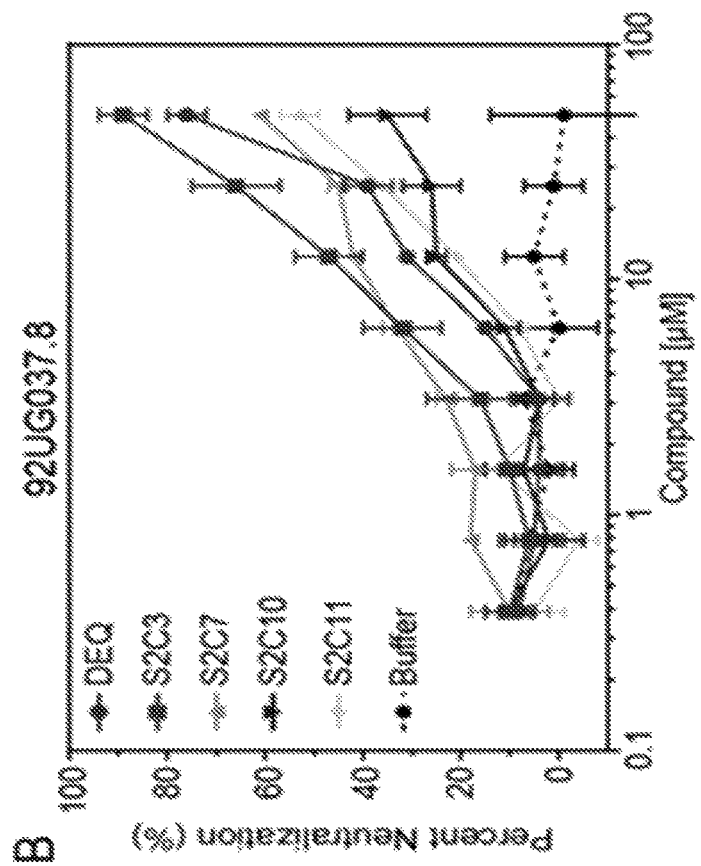
Figure 17A:
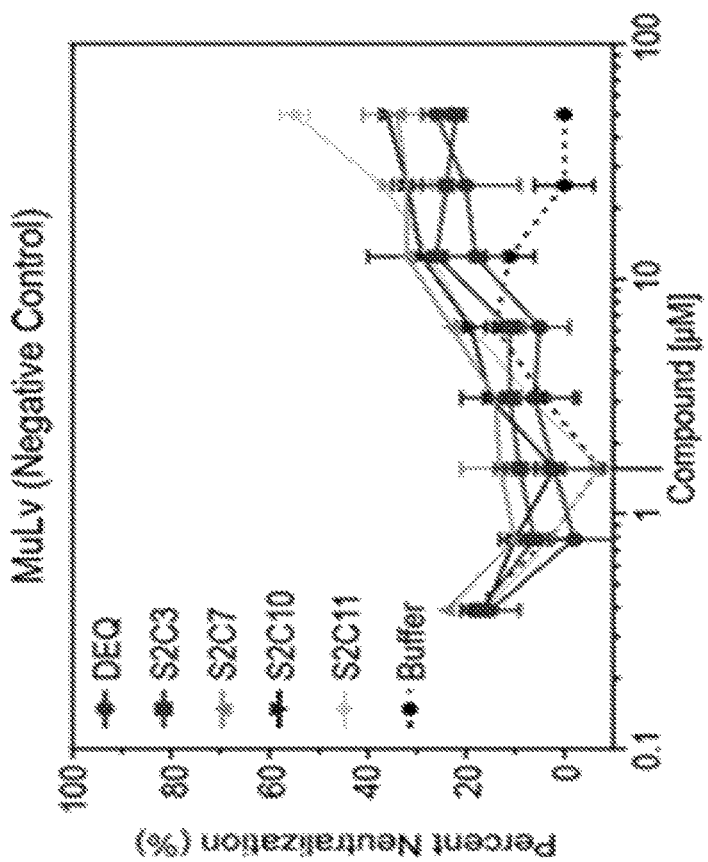
Figure 17D:
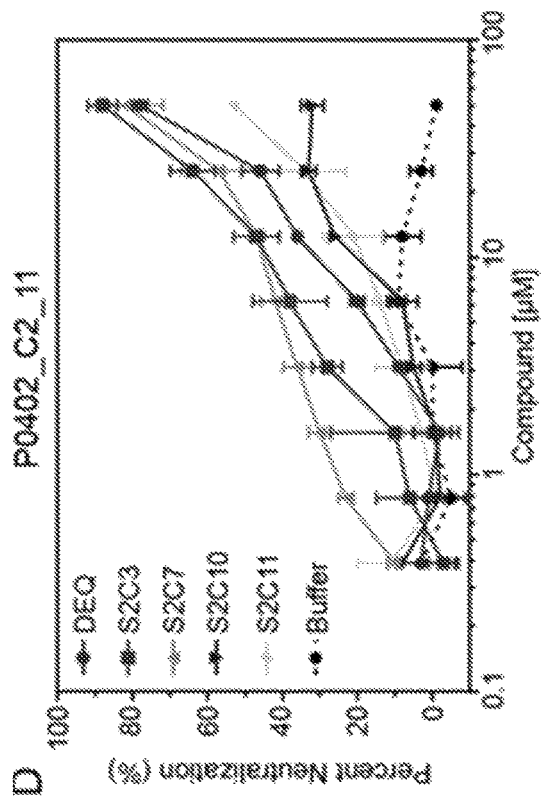
Figure 17E:
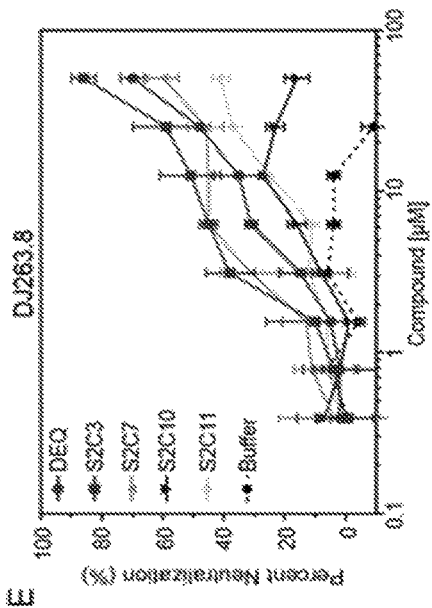
Figure 17C:
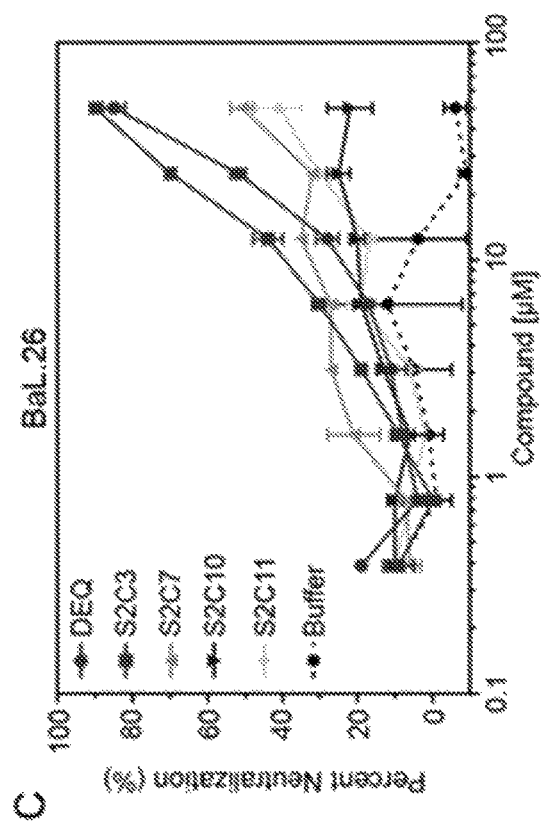

FIG. 17A-17E shows compound inhibition of viral infectivity against different HIV-1 isolates. Pseudoviruses containing HIV-1 Env of different strains-92UG037.8 (FIG. 17B), Bal.26 (FIG. 17C), P0402-C2-11 (FIG. 17D) and DJ263.8 (FIG. 17E) were tested for inhibition of viral infectivity by dequalinium, S2C3, S2C7, S2C10 and S2C11. Buffer, sodium acetate, 50 mM, pH 4.5. Murine leukemia virus (MuLV) was used as a negative control (FIG. 17A).

Figure 18A:
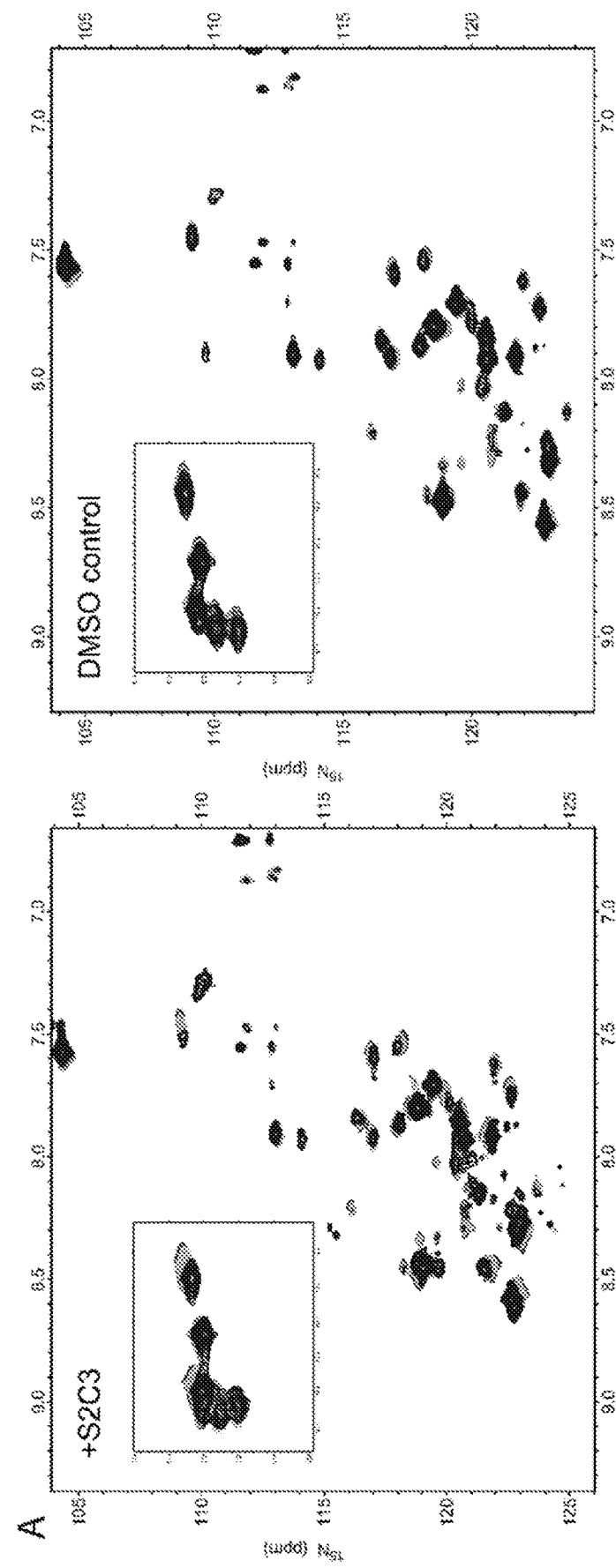
Figure 18B:
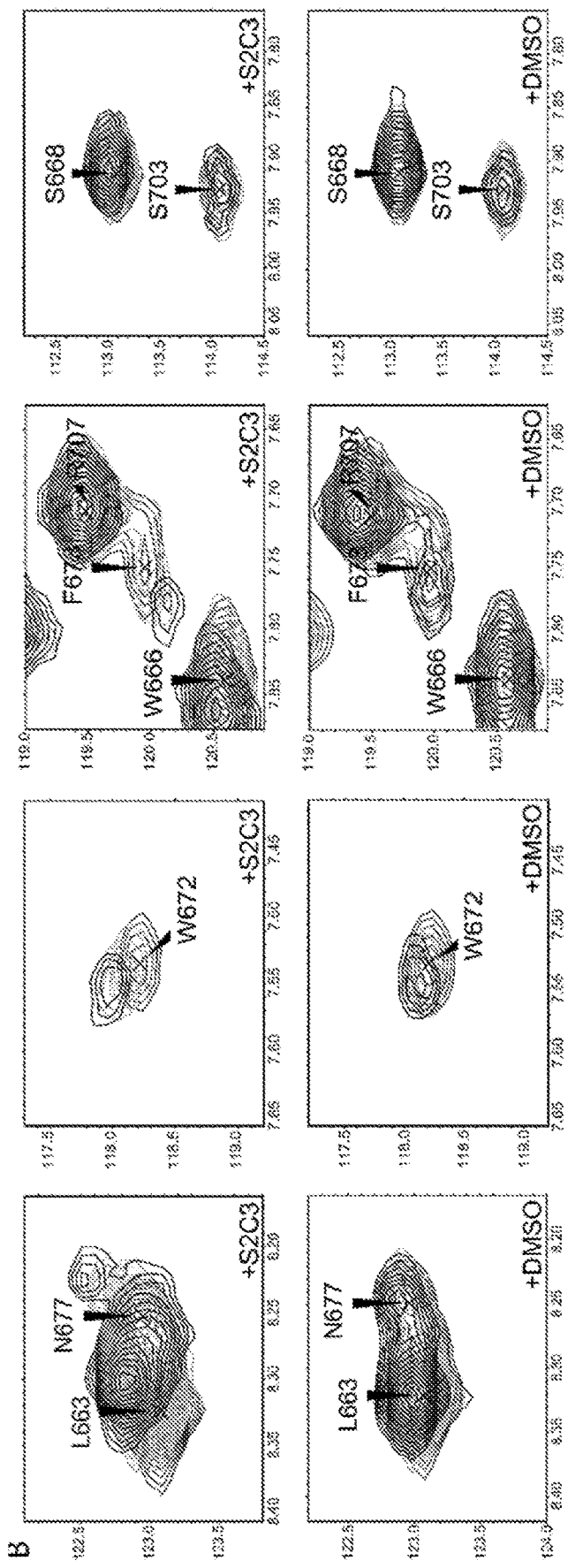
Figure 18C:
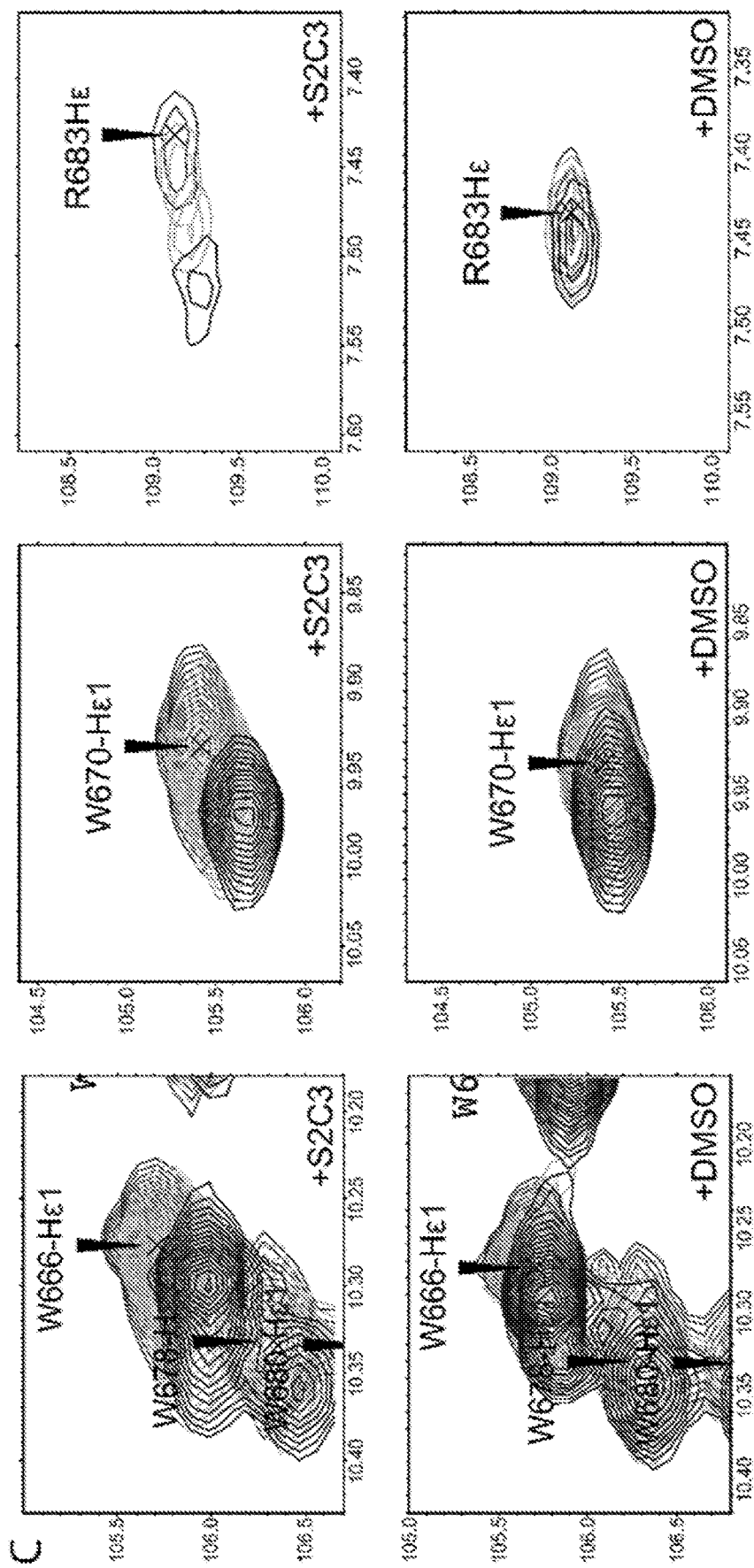

FIG. 18A-18C show chemical shift perturbation of the MPER-TMD caused by S2C3. The 15N-labeled MPER-TMD in bicelles was titrated with increasing concentrations of S2C3 and a series of 2D TROSY-HSQC spectra were recorded. FIG. 18A shows 2D TROSY-HSQC spectra of the MPER-TMD in the presence of S2C3 at various concentrations: red, no S2C3; green, 0.5 mM S2C3 (by adding 3.5 µL S2C3-DMSO solution); orange, 1.5 mM S2C3 (10.5 µl S2C3-DMSO solution); and blue, 2.5 mM S2C3 (17.5 µl S2C3-DMSO solution). Right, 2D TROSY-HSQC spectra of the MPER-TMD in the presence of various amount of DMSO as negative controls. Equal volume of DMSO was added to the MPER-TMD sample: red, no DMSO; green, 3.5 µl of DMSO; orange, 10.5 µl; blue, 17.5 µl. FIG. 18B shows a close-up view of selected residues in the spectrum with S2C3 (upper) or DMSO (lower) showing examples of backbone HNs of the residues exhibiting chemical shift changes. The HNs of residues S703 and S668 are displayed in the last column indicating minimal impact on their HN peaks by S2C3 addition. FIG. 18C shows a close-up view of selected residues in the spectrum with S2C3 (upper) or DMSO (lower) showing examples of side chain HNs of the residues exhibiting chemical shift changes.

Figure 19A:
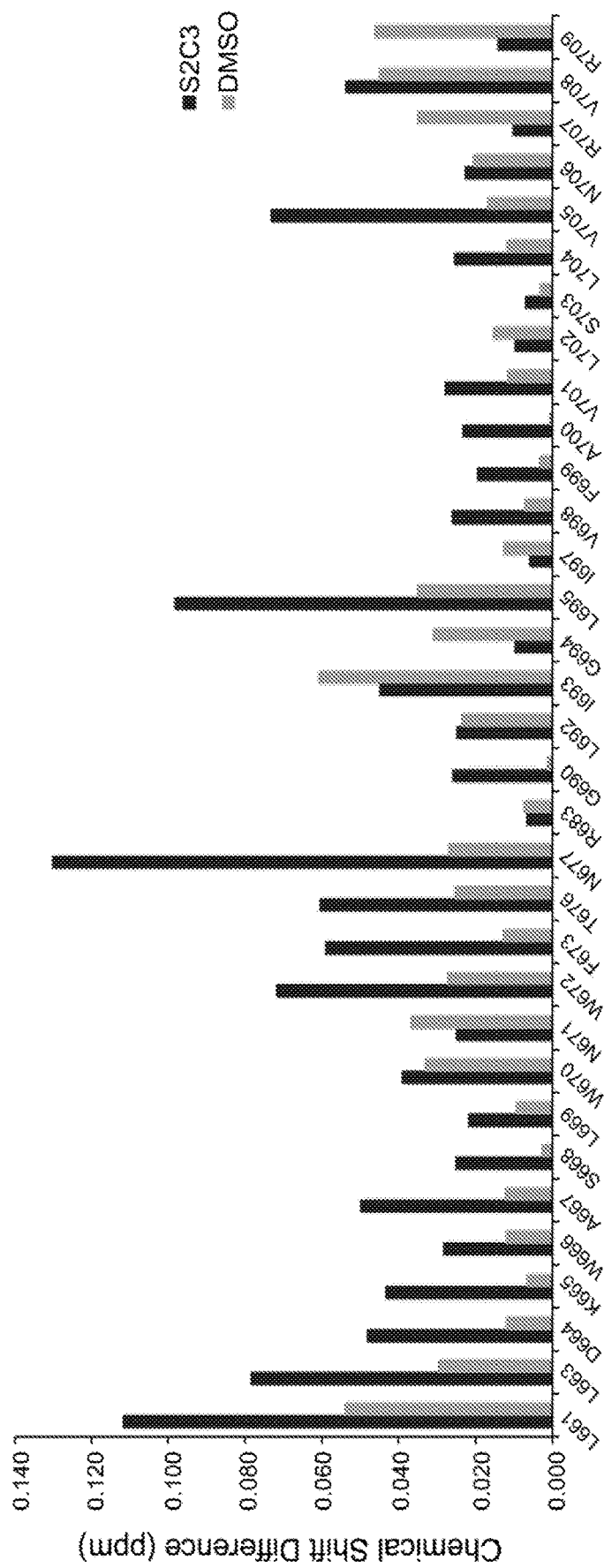
Figure 19B:

FIG. 19A-19B shows chemical shift differences and peak intensity changes of backbone amide protons upon S2C3 addition. Chemical shift and peak intensity differences observed in the titration experiment are summarized and plotted. FIG. 19A shows Averaged chemical shift differences of backbone HNs in the MPER-TMD after addition of 2.5 mM S2C3 or equal volume of DMSO. FIG. 19B shows the ratio between peak intensities of backbone HNs in the MPER-TMD from the TROSY-HSQC spectrum with 2.5 mM S2C3 normalized by those from the spectrum with no S2C3, and peak intensities of backbone HNs in the MPER-TMD from the spectrum with the equal volume DMSO (17.5 µl) normalized by those from the spectrum without DMSO. In (FIG. 19A) and (FIG. 19B), residues with very weak peaks and those with overlap peaks were excluded.

FIG. 20A-20C shows $^1$H NMR spectra of S2C3. FIG. 20A shows Left, zoom-in view of $^1$H spectrum acquired using 2.5 mM S2C3 mixed with 0.25 mM $^{15}$N-labeled MPER-TMD/bicelle. The peaks correspond to the protons of the head groups of S2C3. Right, zoom-in view of $^1$H spectrum acquired using 0.25 mM $^{15}$N-labeled MPER-TMD/bicelle without S2C3 as a control. Two $^1$H spectra are shown in the range of 6.0-9.0 ppm. FIG. 20B shows the zoomed-in views of $^1$H spectrum acquired using 2.5 mM S2C3 in the bicelles with perdeuterated acyl chains, showing peaks in the range of 6.0-9.0 ppm (left) and 0.0-3.0 ppm (right). Those corresponding to the protons of S2C3 are indicated by arrows. Some protons could have peaks in the range of 3.0-6.0 ppm, making it difficult to distinguish from peaks of water and head groups of DMPC and DHPC in the NOESY spectrum. Those peaks were not shown here or identified as NOE peaks between S2C3 and the MPER-TMD. The S2C3 peaks broadened in the presence of the MPER-TMD, as shown in (FIG. 20A), consistent with its interaction with the protein. FIG. 20C shows the Zoomed-in views of $^1$H spectrum acquired using the bicelles with deuterated acyl chain, showing peaks in the range of 6.0-9.0 ppm (left) and 0.0-3.0 ppm (right) as controls. FIG. 20D shows $^1$H spectrum of S2C3 predicted by a $^1$H prediction software available on the world wide web at http://<www.cheminfo.org/Spectra/NMR/Predictions/1H_Prediction/>.

Figure 21A:
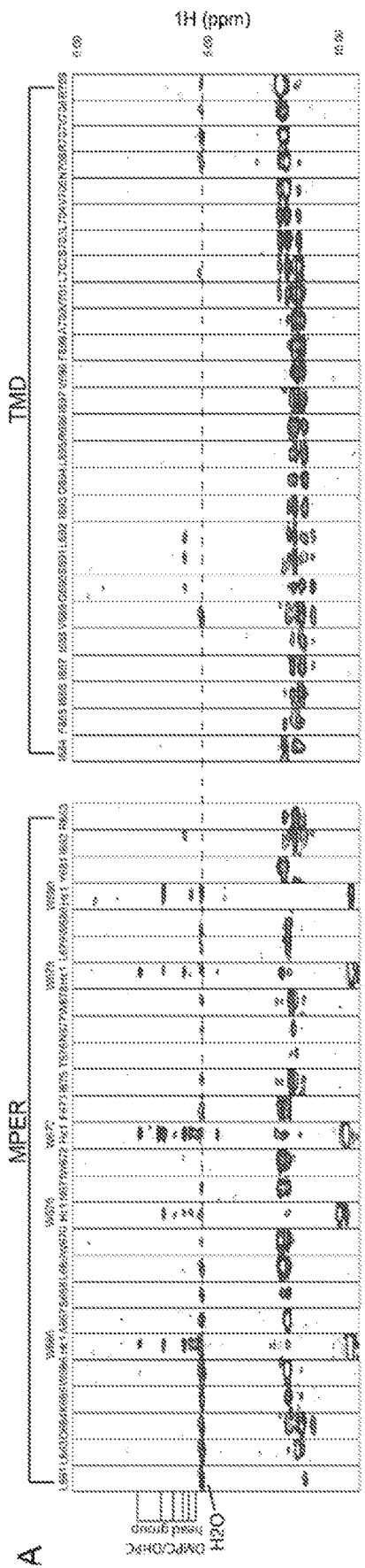
Figure 21B:
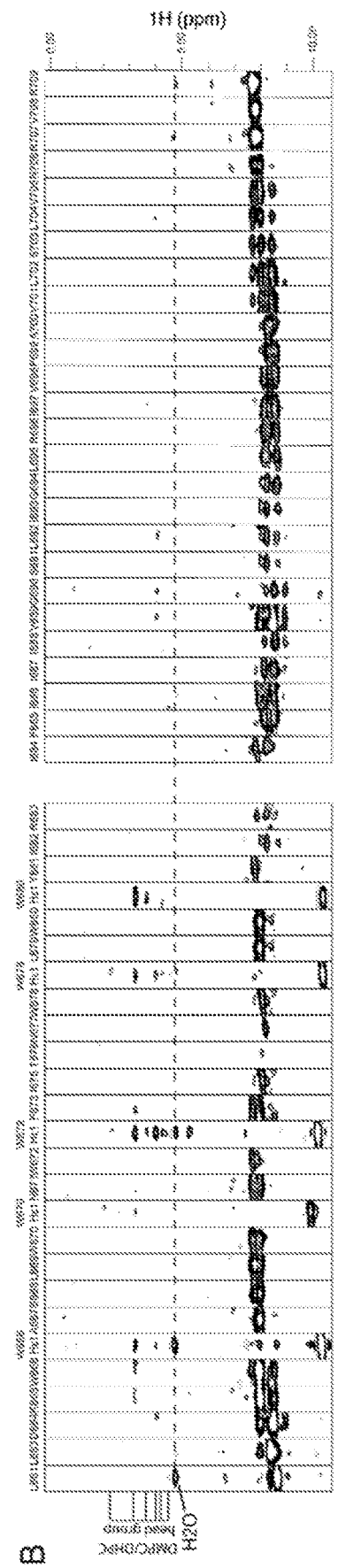
Figure 21C:
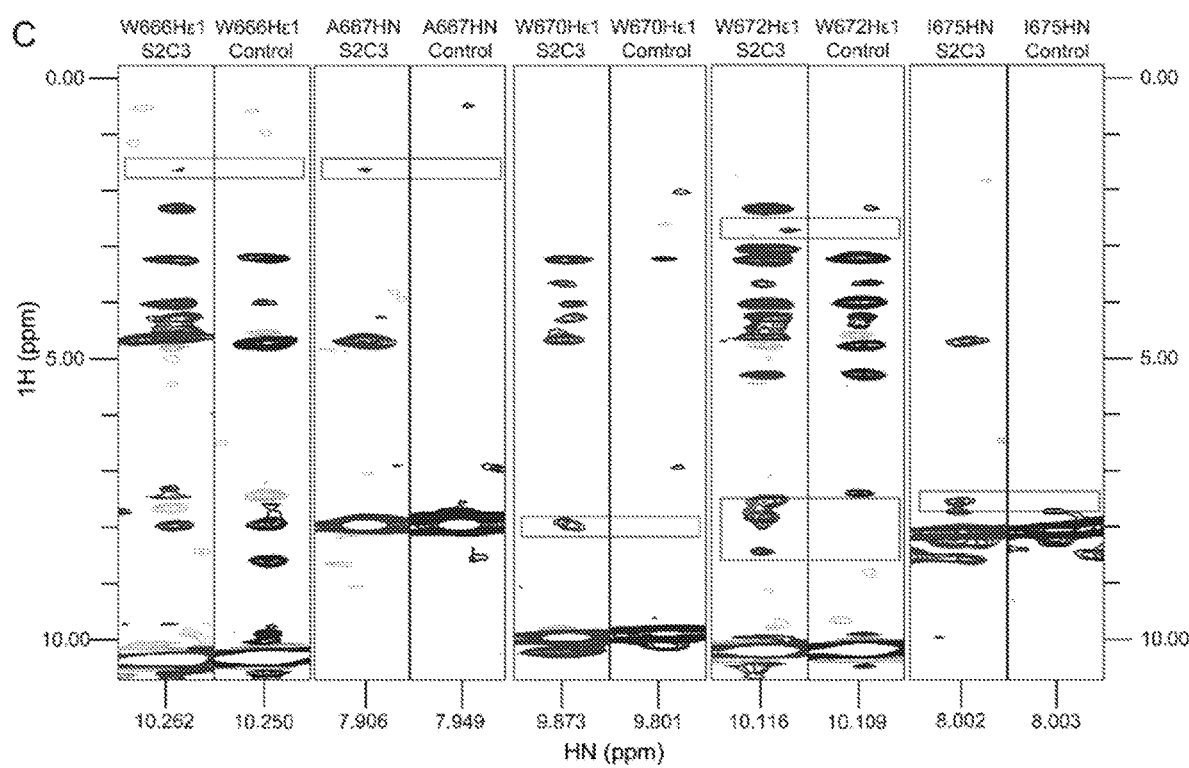

FIG. 21A-21C shows NOESY spectra of the MPER-TMD in the presence or absence of S2C3. FIG. 21A shows $^{15}$N-edited NOESY-TROSY-HSQC spectrum with J($^{13}$C-$^1$H) modulation[41] acquired using 0.6 mM $^{15}$N, $^{13}$C, $^2$H-labeled MPER-TMD reconstituted in perdeuterated bicelles in the presence of 2 mM S2C3. FIG. 21B shows $^{15}$N-edited NOESY-TROSY-HSQC spectrum with J($^{13}$C-$^1$H) modulation acquired using a control sample −0.6 mM $^{15}$N, $^{13}$C, $^2$H-labeled MPER-TMD reconstituted in perdeuterated bicelles without S2C3. In (FIG. 21A) and (FIG. 21B), left, NOESY strips of the residues 662-683 in the MPER; right, NOESY strips of the residues 684-709 in the TMD. Solvent water shows a peak with a $^1$H chemical shift at ~4.7 ppm; protons of the head groups of DMPC/DHPC bicelles give peaks with chemical shifts at 2.2-4.2 ppm. (FIG. 21C) Side-by-side comparison of the NOESY strips of amide protons W6661-1E, A667HN, W670HE, W672HE, I675HN and W680HE in the presence (S2C3) or absence (control) of S2C3. NOE peaks between protons of S2C3 and amide protons of these residues were observed and are highlighted by blue boxes.

Figure 22A:
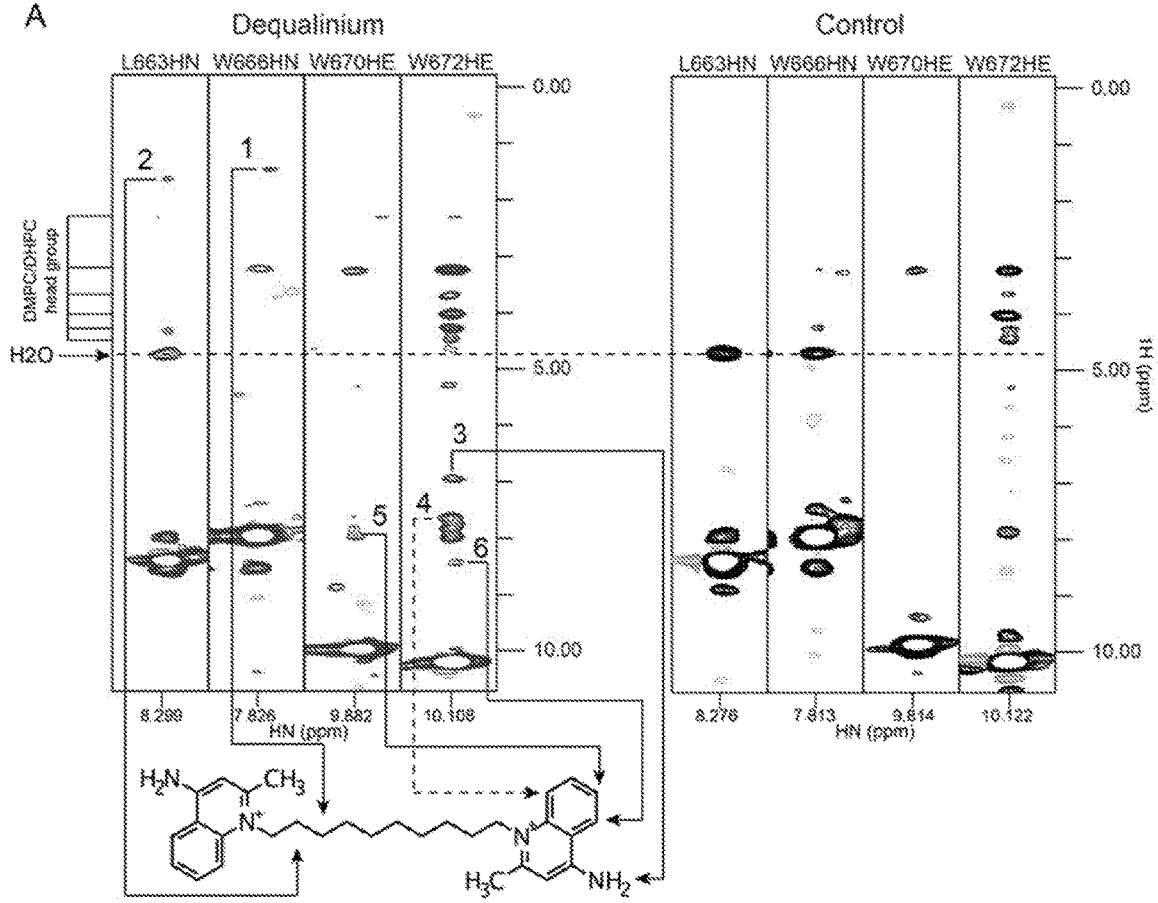
Figure 22B:
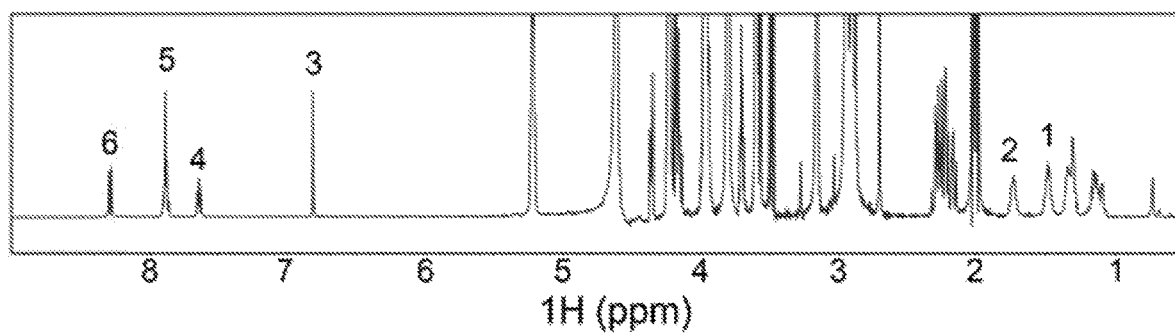

FIG. 22A-22B shows a preliminary NMR structure of dequalinium in complex with the MPER-TMD. FIG. 22A shows strips from the 3D $^{15}$N-edited NOESY-TROSY-HSQC spectrum recorded using the $^{15}$N-labeled perdeuterated MPER-TMD protein (0.6 mM) in the presence of 3 mM dequalinium (left). Right, strips from the 3D $^{15}$N-edited NOESY-TROSY spectrum recorded using the $^{15}$N-labeled perdeuterated MPER-TMD protein (0.6 mM) in absence of dequalinium (Control). The MPER-TMD was reconstituted in perdeuterated DMPC/DHPC bicelles, acyl chains of which were deuterated. Protein-dequalinium NOE peaks in the strips in (FIG. 22A) were mapped to the dequalinium molecule at the bottom, as indicated by arrows. Solvent water shows a peak with a $^1$H chemical shift at ~4.7 ppm; protons of head groups of DMPC/DHPC bicelles give peaks with chemical shifts at 2.2-4.2 ppm. FIG. 22B shows $^1$H NMR spectrum of 3 mM dequalinium dissolved in the perdeuterated bicelles. Peaks observed in the NOESY strips in (FIG. 22A) were indicated in the $^1$H spectrum by the corresponding numbers.

Figure 23:
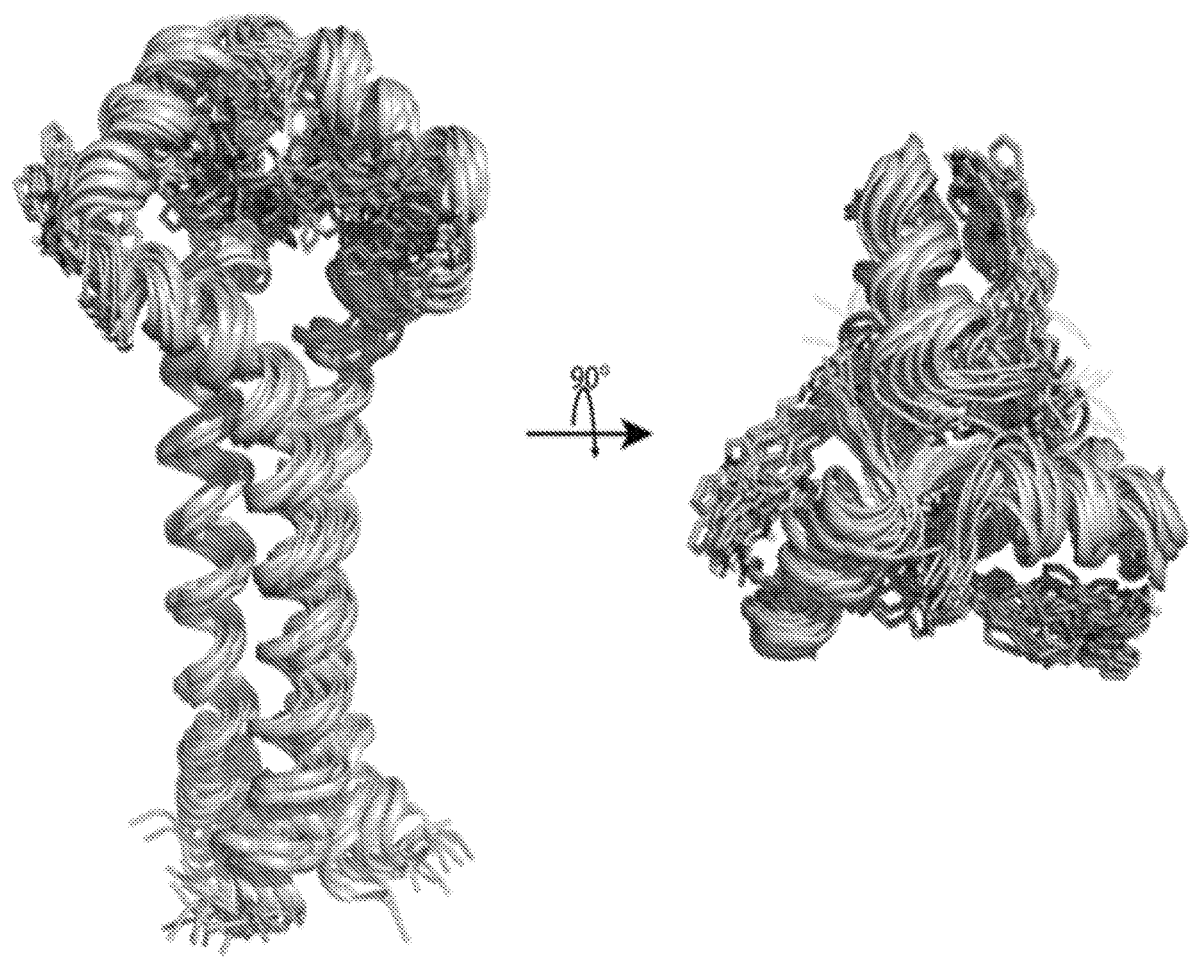

FIG. 23 shows the ensemble of 15 lowest energy structures of the S2C3-MPER complex generated using XPLOR-NIH. NOE restraints between S2C3 and the MPER-TMD extracted from the $^{15}$N-edited NOESY-TROSY-HSQC with J($^{13}$C-$^1$H) modulation together with NOE restraints from the previously published MPER-TMD structure[40] were used for structure calculation, as described in Methods. 15 structures with the lowest energies were selected from 100 calculated structures, and used for the final ensemble. Left, side views of the ensemble; right, top views. The protein backbone is shown in cartoon representation in beige. Three S2C3 molecules occupying three binding pockets of one MPER trimer are shown in the stick representation in magenta, cyan and green, respectively.

Figure 24A:
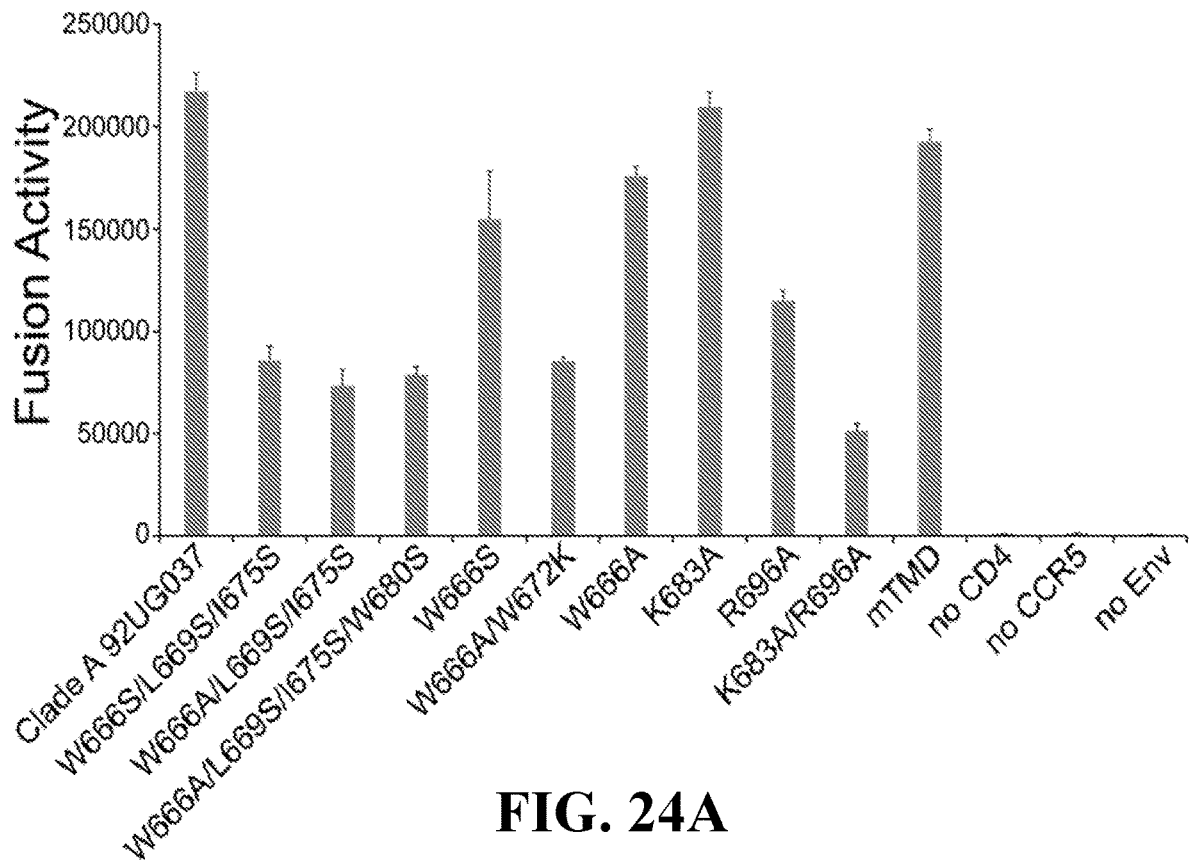
Figure 24B:
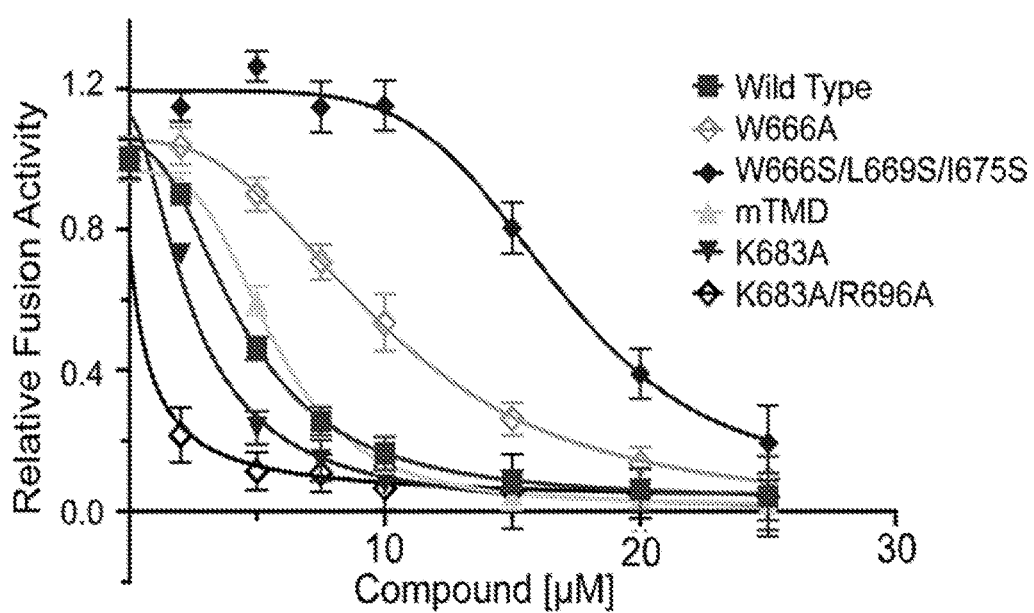

FIG. 24A-24B shows Env sensitivity to S2C3 modulated by mutations in the MPER. FIG. 24A shows fusion activities of 92UG037.8 HIV-1 gp160 and its mutants measured in the cell-cell fusion assay. 293T cells transfected with 1 µg of the 92UG037.8 Env expression plasmid or each of its mutants were mixed with CD4- and CCR5-expressing cells. Cell-cell fusion led to reconstitution of active β-galactosidase; fusion activity was quantified by a chemiluminescent assay. No Env, no CD4 and no CCR5 were negative controls. The experiment was carried out in triplicate and repeated twice with similar results. Error bars indicate the standard deviation calculated by the Excel STDEV function. FIG. 24B shows S2C3 inhibition of the cell-cell fusion mediated by wildtype Env and its mutants was compared. For all experiments, equal volume of DMSO was used as a no-inhibition reference. Fusion activities in the presence of S2C3 at various concentrations were normalized by the DMSO references.

DETAILED DESCRIPTION

Viral infections such as HIV and AIDS are a global pandemic affecting approximately 36.7 million people worldwide. HIV infection leads to devastating symptoms, such as vulnerability to opportunistic secondary infections which can be fatal. HIV takes over the subject's immune cells (e.g., CD4+ T cells) to replicate and prevent the subject's immune system from eliciting an immune response to the virus. Combination therapies that prevent HIV from infiltrating and replicating in the host cells can slow down disease progression and reduce the severity of the symptoms. However, HIV can be resistant to these treatments and the current therapies have several unwanted side effects such as nausea, vomiting, and extreme fatigue, among others.

Retroviruses, such as the HIV virus, are RNA viruses that have the enzyme, reverse transcriptase, which enables retroviruses to make a DNA copy of the viral RNA. Some viruses have an outer envelope and a dense cylindrical core containing RNA or DNA genome. The envelope consists of a lipid membrane with protruding spikes which are coated with glycoproteins. The glycoproteins contain different sugar molecules, some of which appear to be constant, but some may be variable. The variability of these sugar molecules that allow retroviruses such as HIV to elude the host subject's immune system to prevent detection of the viral particles. In particular, the glycoproteins on the envelope can form heterodimers that act as spikes that mediate attachment and entry into the host cell.

Aspects of this invention are related, in part, to the discovery of small-molecule fusion inhibitors that target the membrane proximal external region (MPER) of HIV-1 envelope (Env) spikes and prevent the virus's fusion to a host cell. The MPER, a hydrophobic region of ~25 residues, adjacent to the viral membrane, is one of the most conserved regions in gp41 and is required for viral infectivity[26-28]. It is an extensively studied vaccine target recognized by a number of anti-gp41 bnAbs, including 2F5, 4E10, Z13e1 and 10E8[29-31]. These antibodies appear to block HIV-1 infection by a common mechanism—binding the prehairpin intermediate state of gp41 via their lipid binding activity[23-25]. Despite their remarkable neutralization potencies against a wide spectrum of HIV-1 isolates in vitro, studies involving passive transfer of 2F5 and 4E10 in HIV-1 infected patients suggest that the antibodies may not be effective in blocking HIV-1 propagation in vivo[32]. Data presented herein show small-molecule compounds that can mimic these bnAbs to bind the MPER and specifically block HIV-1 Env-mediated membrane fusion. These data highlight a surprising role for MPER mediating viral fusion.

Virus-Cell Fusion

Pathogenic viruses can comprise viral envelopes that cover the viral protective protein capsids. These envelopes can be derived from, e.g., portions of the host cell membranes (phospholipids and proteins), but can include some viral glycoproteins (e.g. gp41). Envelope glycoproteins (Env) mediate fusion of viral and target cell membranes to initiate infection. Glycoproteins can be specific to a given viral envelope (e.g., HIV-1 Env) and comprise oligosaccharide chains (glycans) covalently attached to amino acid side-chains. The carbohydrate is attached to the protein in a co-translational or post-translational modification and this process is known as glycosylation. Viral glycoproteins are expressed on the viral envelope. Non-limiting examples of viral glycoproteins include HIV glycoproteins-gp41, gp160, gp120.

In a viral infection (e.g., an HIV infection), an Env polypeptide chain is produced as a precursor, gp160, which trimerizes and then undergoes cleavage by a furin-like protease into two non-covalently associated fragments: the receptor-binding fragment gp120 and the fusion fragment gp41. Three copies of each fragment constitute the mature viral spike (gp120/gp41). Sequential binding of gp120 to primary receptor CD4 and a coreceptor can induce a cascade of refolding events in gp41. Gp41, with its C-terminal transmembrane segment inserted in the viral membrane, folds into a pre-fusion conformation within the precursor gp160. Cleavage between gp120 and gp41 makes the protein metastable with respect to the post-fusion conformation. When triggered, the N-terminal fusion peptide of gp41 translocates and inserts into the target cell membrane. The extended conformation of gp41, with the fusion peptide inserted into the target cell membrane and the transmembrane anchor in the viral membrane, is referred to as the prehairpin intermediate. Subsequent rearrangements involve refolding of gp41 into a hairpin conformation, creating a six-helix bundle known as the post-fusion conformation, which brings the two membranes together and leads to membrane fusion. This process is shown herein in FIG. IA-1B.

```
The nucleic acid sequence of the envelope surface glycoprotein, gp160, is
known in the art (e.g., NCBI Reference Gene ID: 155971; NC_001802.1):
                                                           (SEQ ID NO: 1)
ATGAGAGTGAAGGAGAAATATCAGCACTTGTGGAGATGGGGGTGGAGATGGGGCACCATGCTCCTTGGGA

TGTTGATGATCTGTAGTGCTACAGAAAAATTGTGGGTCACAGTCTATTATGGGGTACCTGTGTGGAAGGA

AGCAACCACCACTCTATTTTGTGCATCAGATGCTAAAGCATATGATACAGAGGTACATAATGTTTGGGCC

ACACATGCCTGTGTACCCACAGACCCCAACCCACAAGAAGTAGTATTGGTAAATGTGACAGAAAATTTTA

ACATGTGGAAAAATGACATGGTAGAACAGATGCATGAGGATATAATCAGTTTATGGGATCAAAGCCTAAA

GCCATGTGTAAAATTAACCCCACTCTGTGTTAGTTTAAAGTGCACTGATTTGAAGAATGATACTAATACC

AATAGTAGTAGCGGGAGAATGATAATGGAGAAAGGAGAGATAAAAAACTGCTCTTTCAATATCAGCACAA

GCATAAGAGGTAAGGTGCAGAAAGAATATGCATTTTTTTATAAACTTGATATAATACCAATAGATAATGA

TACTACCAGCTATAAGTTGACAAGTTGTAACACCTCAGTCATTACACAGGCCTGTCCAAAGGTATCCTTT

GAGCCAATTCCCATACATTATTGTGCCCCGGCTGGTTTTGCGATTCTAAAATGTAATAATAAGACGTTCA

ATGGAACAGGACCATGTACAAATGTCAGCACAGTACAATGTACACATGGAATTAGGCCAGTAGTATCAAC

TCAACTGCTGTTAAATGGCAGTCTAGCAGAAGAAGAGGTAGTAATTAGATCTGTCAATTTCACGGACAAT

GCTAAAACCATAATAGTACAGCTGAACACATCTGTAGAAATTAATTGTACAAGACCCAACAACAATACAA

GAAAAGAATCCGTATCCAGAGAGGACCAGGGAGAGCATTTGTTACAATAGGAAAAATAGGAAATATGAG
```

-continued

```
ACAAGCACATTGTAACATTAGTAGAGCAAAATGGAATAACACTTTAAAACAGATAGCTAGCAAATTAAGA
GAACAATTTGGAAATAATAAAACAATAATCTTTAAGCAATCCTCAGGAGGGGACCCAGAAATTGTAACGC
ACAGTTTTAATTGTGGAGGGGAATTTTTCTACTGTAATTCAACACAACTGTTTAATAGTACTTGGTTTAA
TAGTACTTGGAGTACTGAAGGGTCAAATAACACTGAAGGAAGTGACACAATCACCCTCCCATGCAGAATA
AAACAAATTATAAACATGTGGCAGAAAGTAGGAAAAGCAATGTATGCCCCTCCCATCAGTGGACAAATTA
GATGTTCATCAAATATTACAGGGCTGCTATTAACAAGAGATGGTGGTAATAGCAACAATGAGTCCGAGAT
CTTCAGACCTGGAGGAGGAGATATGAGGGACAATTGGAGAAGTGAATTATATAAATATAAAGTAGTAAAA
ATTGAACCATTAGGAGTAGCACCCACCAAGGCAAAGAGAAGAGTGGTGCAGAGAGAAAAAAGAGCAGTGG
GAATAGGAGCTTTGTTCCTTGGGTTCTTGGGAGCAGCAGGAAGCACTATGGGCGCAGCCTCAATGACGCT
GACGGTACAGGCCAGACAATTATTGTCTGGTATAGTGCAGCAGCAGAACAATTTGCTGAGGGCTATTGAG
GCGCAACAGCATCTGTTGCAACTCACAGTCTGGGGCATCAAGCAGCTCCAGGCAAGAATCCTGGCTGTGG
AAAGATACCTAAAGGATCAACAGCTCCTGGGGATTTGGGGTTGCTCTGGAAAACTCATTTGCACCACTGC
TGTGCCTTGGAATGCTAGTTGGAGTAATAAATCTCTGGAACAGATTTGGAATCACACGACCTGGATGGAG
TGGGACAGAGAAATTAACAATTACACAAGCTTAATACACTCCTTAATTGAAGAATCGCAAAACCAGCAAG
AAAAGAATGAACAAGAATTATTGGAATTAGATAAATGGGCAAGTTTGTGGAATTGGTTTAACATAACAAA
TTGGCTGTGGTATATAAAATTATTCATAATGATAGTAGGAGGCTTGGTAGGTTTAAGAATAGTTTTTGCT
GTACTTTCTATAGTGAATAGAGTTAGGCAGGGATATTCACCATTATCGTTTCAGACCCACCTCCCAACCC
CGAGGGGACCCGACAGGCCCGAAGGAATAGAAGAAGAAGGTGGAGAGAGAGACAGAGACAGATCCATTCG
ATTAGTGAACGGATCCTTGGCACTTATCTGGGACGATCTGCGGAGCCTGTGCCTCTTCAGCTACCACCGC
TTGAGAGACTTACTCTTGATTGTAACGAGGATTGTGGAACTTCTGGGACGCAGGGGGTGGGAAGCCCTCA
AATATTGGTGGAATCTCCTACAGTATTGGAGTCAGGAACTAAAGAATAGTGCTGTTAGCTTGCTCAATGC
CACAGCCATAGCAGTAGCTGAGGGGACAGATAGGGTTATAGAAGTAGTACAAGGAGCTTGTAGAGCTATT
CGCCACATACCTAGAAGAATAAGACAGGGCTTGGAAAGGATTTTGCTATAA.
```

The amino acid sequence of the envelope surface glycoprotein, gp160, is the following (NCBI Reference Sequence NP_057856.1):

(SEQ ID NO: 2)

```
  1 mrvkekyqhl wrwgwrwgtm llgmlmicsa teklwvtvyy gvpvwkeatt tlfcasdaka
 61 ydtevhnvwa thacvptdpn pqevvlvnvt enfnmwkndm veqmhediis lwdqslkpcv
121 kltplcvslk ctdlkndtnt nsssgrmime kgeikncsfn istsirgkvq keyaffykld
181 iipidndtts ykltscntsv itqacpkvsf epipihycap agfailkcnn ktfngtgpct
241 nvstvqcthg irpvvstqll lngslaeeev virsvnftdn aktiivqlnt sveinctrpn
301 nntrkririq rgpgrafvti gkignmrqah cnisrakwnn tlkqiasklr eqfgnnktii
361 fkqssggdpe ivthsfncgg effycnstql fnstwfnstw stegsnnteg sdtitlpcri
421 kqiinmwqkv gkamyappis gqircssnit gllltrdggn snneseifrp gggdmrdnwr
481 selykykvvk ieplgvaptk akrrvvqrek ravgigalfl gflgaagstm gaasmtltvq
541 arqllsgivq qqnnllraie aqqhllqltv wgikqlqari laverylkdq qllgiwgcsg
601 klicttavpw naswsnksle qiwnhttwme wdreinnyts lihslieesq nqqekneqel
661 leldkwaslw nwfnitnwlw yiklfimivg glvglrivfa vlsivnrvrq gysplsfqth
721 lptprgpdrp egieeegger drdrsirlvn gslaliwddl rslclfsyhr lrdlllivtr
781 ivellgrrgw ealkywwnll qywsqelkns avsllnatai avaegtdrvi evvqgacrai
841 rhiprrirqg lerill.
```

-continued

The amino acid sequence of gp120 is the following (NCBI Reference Sequence NP_579894.2):

(SEQ ID NO: 3)

```
  1 sateklwvtv yygvpvwkea tttlfcasda kaydtevhnv wathacvptd pnpqevvlvn 61 vtenfnmwkn dmveqmhedi islwdqslkp cvkltplcvs lkctdlkndt ntnsssgrmi 121 mekgeikncs fnistsirgk vqkeyaffyk ldiipidndt tsykltscnt svitqacpkv 181 sfepipihyc apagfailkc nnktfngtgp ctnvstvqct hgirpvvstq lllngslaee 241 evvirsvnft dnaktiivql ntsveinctr pnnntrkrir iqrgpgrafv tigkignmrq 301 ahcnisrakw nntlkqiask lreqfgnnkt iifkqssggd peivthsfnc ggeffycnst 361 qlfnstwfns twstegsnnt egsdtitlpc rikqiinmwq kvgkamyapp isgqircssn 421 itglllltrdg gnsnneseif rpgggdmrdn wrselykykv vkieplgvap tkakrrvvqr 481 ekr
```

The amino acid sequence of gp41is the following (NCBI Reference Sequence NP_579895.1):

(SEQ ID NO: 4)

```
  1 avgigalflg flgaagstmg aasmtltvqa rqllsgivqq qnnllraiea qqhllqltvw 61 gikqlqaril averylkdqq llgiwgcsgk licttavpwn aswsnksleq iwnhttwmew 121 dreinnytsl ihslieesqn qqekneqell eldkwaslwn wfnitnwlwy iklfimivgg 181 lvglrivfav lsivnrvrqg ysplsfqthl ptprgpdrpe gieeeggerd rdrsirlvng 241 slaliwddlr slclfsyhrl rdllllivtri vellgrrgwe alkywwnllq ywsgelknsa 301 vsllnataia vaegtdrvie vvqgacrair hiprrirqgl erill.
```

The membrane proximal external region (MPER) is a hydrophobic region of about 25 residues within gp41. The MPER is one of the most conserved regions in gp41 and allows for viral infectivity. An example of the MPER region is shown herein in FIG. 2A-2C. The conserved amino acid sequence of MPER across various HIV-1 strains is the following (see Zhang et al. *PLOS One* (2015), FIG. 1): LDJWJJJWJWJJIJJWLWYIK (SEQ ID NO: 5); wherein "J" is any amino acid found within SEQ ID NO: 5.

The MPER used for structural studies as described in the working examples is derived from or expressed by Clade D HIV-1 isolate 92UG024.2. The amino acid sequence for the Clade D HIV-1 isolate 92UG024.2 MPER is the following: DLLELDKWASLWNWFDITNWLWYIR (SEQ ID NO: 6).

The MPER described herein is specifically targeted to prevent fusion of the viral Env to a target cell. One aspect herein is a method for inhibiting Env fusion to a target cell comprising contacting a target cell with a compound or agent, or composition or pharmaceutical composition thereof, described herein that inhibits the MPER of a viral envelope (Env). In one embodiment, Env fusion to a target cell is inhibited by at least 5%, 10%, 15%, 20%, 25%, 30%, 35%, 40%, 45%, 50%, 55%, 60%, 65%, 70%, 75%, 80%, 85%, 90%, 95%, 99%, or more as compared to an appropriate control (e.g., a substantial similar population that is not contacted by an agent described herein). One skilled in the art can assess whether Env fusion to a target cell has been inhibited via a cell-cell fusion assay (e.g., fluorescent assays, rhodamine energy transfer, lipid mixing assays, pyrene excimer fluorescence assays, and the like).

In one embodiment, the compound or agent, or composition or pharmaceutical composition thereof, described herein result in inhibition of the levels and/or activity of the MPER of gp41 on the viral Env. In one embodiment, levels and/or activity of the MPER of gp41 on the viral Env inhibited by at least 5%, 10%, 15%, 20%, 25%, 30%, 35%, 40%, 45%, 50%, 55%, 60%, 65%, 70%, 75%, 80%, 85%, 90%, 95%, 99%, or more as compared to an appropriate control (e.g., a substantial similar population that is not contacted by an agent described herein). One skilled in the art can assess whether levels of the MPER of gp41 on the viral Env are inhibited via PCR-based assays or western blotting to assess MPER of gp41 mRNA or protein levels, respectively. As used herein, "activity" of MPER of gp41 refers to the stabilization and anchoring of the gp41 protein to the host or target cell membrane. One skilled in the art can assess whether activity of the MPER of gp41 on the viral Env are inhibited via cell-cell fusion assays (e.g., fluorescent assays, rhodamine energy transfer, lipid mixing assays, pyrene excimer fluorescence assays, and the like), viral infectivity assays, and surface plasmon resonance (SPR).

Figure 1A:
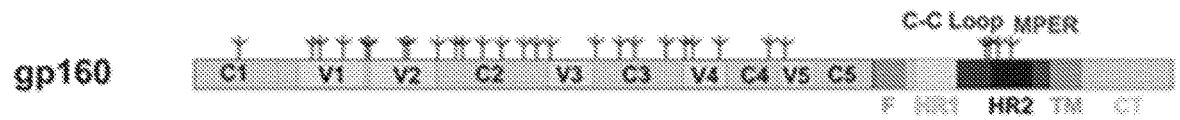
Figure 1B:
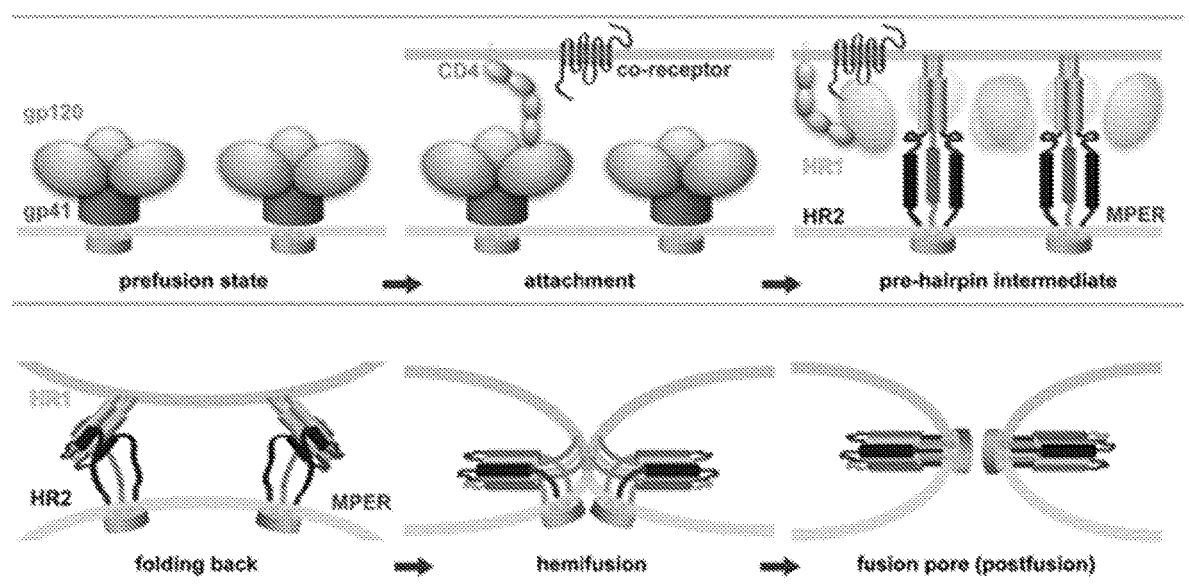

As used herein, the terms "fusion to a target cell" refer to the event when a virus contacts a portion or fragment of a cell membrane (e.g., a target cell) and merges the viral envelope (e.g., HIV-1 Env) with the cell membrane permitting formation of a fusion pore. The formation of the fusion pore allows for exchange between the viral capsid and the target or host cell cytosol. Following fusion to a target cell, a virus can begin to replicate using the proteins already within the host cell. By way of example only, FIG. 1B shows one example of fusion between a viral envelope and a target cell (e.g., HIV-1 Env and a CD4+ T cell). Specifically, FIG. 1B shows the binding of HIV-1 gp120 to the receptor CD4 and coreceptor CXCR4 or CCR$^5$ on the T cell followed by the formation of the prehairpin intermediate. Following the intermediate stage, gp41 can fold back and bringing the two membranes together allowing for the fusion pore formation.

Figure 4:
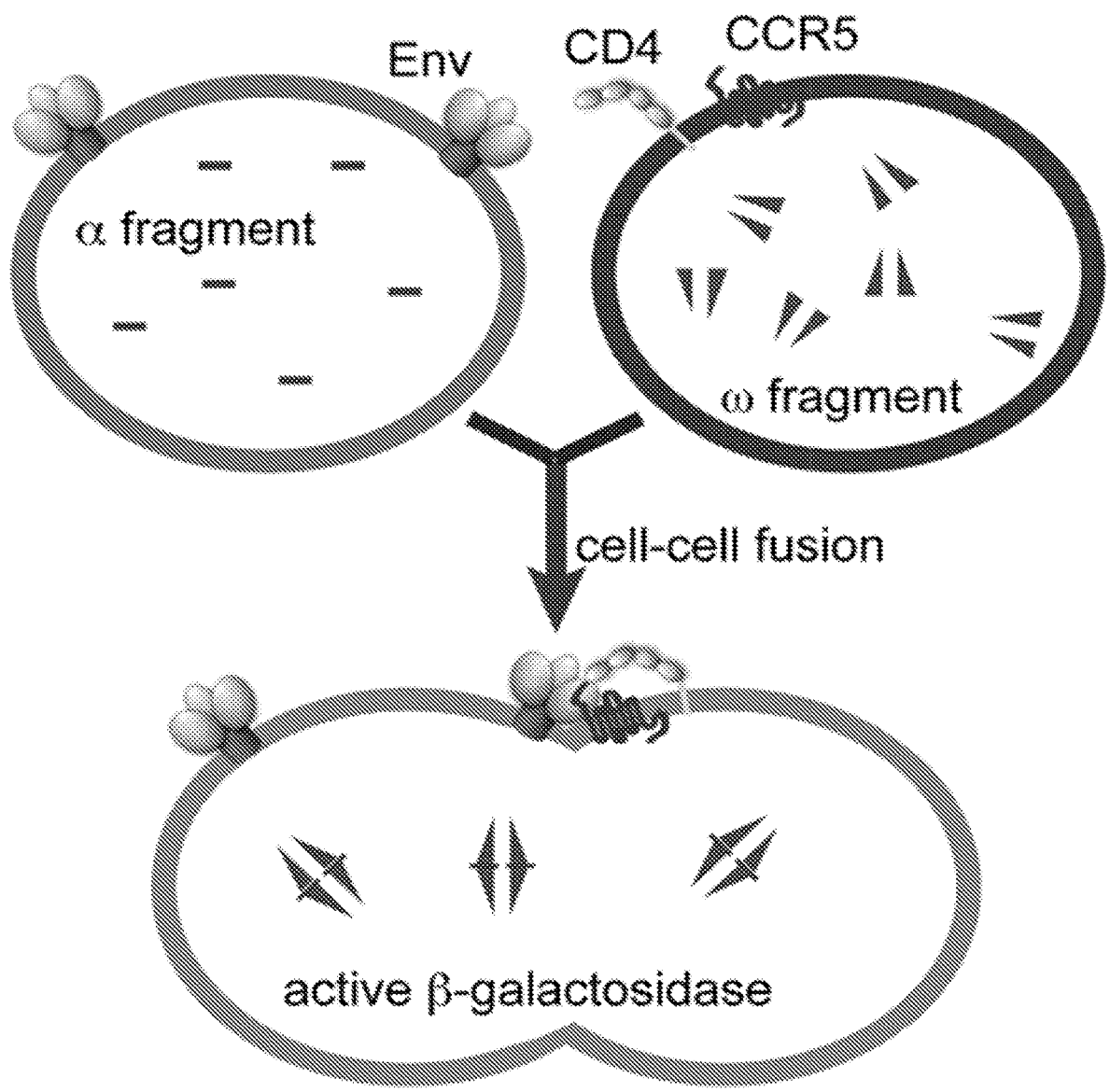

Described herein is a method of identifying and screening for a compound or agent the inhibits HIV-1 Env fusion to a target cell. Fusion can be determined by any assay known in the art. Described herein is a cell-cell fusion assay that has been adapted based on the α-complementation of *E. coli* β-galactosidase. As depicted in FIG. 4, the function of an inactive mutant β-galactosidase with N-terminal residues 11-41 deleted (ω fragment) is rescued by its N-terminal fragment (α fragment; residues 3-90), upon Env-mediated cell-cell fusion. This α-complementation-based method is simple, robust and independent of new transcription, protein synthesis, and trafficking in the fused cells.

Methods of Identifying a Test Agent that Modulates the Activity of MPER.

Described herein are methods of identifying a test agent that modulates the activity of MPER of a viral envelope (Env) comprising (a) contacting a glycoprotein 41 (gp41) or fragment thereof with a test agent; (b) contacting the gp41 or fragment thereof with an antibody or fragment thereof that specifically binds to the MPER; and (c) detecting a contact level between the antibody and the MPER; wherein a change in the contact level relative to a control or reference level indicates that the agent modulates the MPER. Exemplary antibodies that bind MPER include but are not limited to 2F5, 4E10, Z13e1 or 10E8.

In one embodiment, the anti-MPER antibody and test agent contact the MPER at substantially the same time. In an alternative embodiment, the anti-MPER antibody and test agent contact the MPER at different times; e.g., the anti-gp41 contacts the MPER first, and the test agent contacts the MPER after the anti-gp41 antibody is bound.

After the MPER (e.g., gp41) is contacted with the test agent and/or the antibody described herein, a distance or contact level (e.g., binding) between the antibody and the gp41 is measured or determined. The distance or contact level is compared to a reference or distance or contact level. The reference or control can be a distance or contact level measured by contacting the gp41 with the antibody that is not contacted by the test agent. Thus, the test agent competes with the antibody for contact with the gp41 (e.g., at the MPER). A change in distance or contact level relative to the control or reference level indicates the agent modulates the activity of the MPER. Any method known to one of skill in the art could be used for measuring or detecting the distance or contact level (e.g., binding to the MPER).

In some embodiments, the antibody further comprises a label. In some embodiments, the label is a heterologous protein. In some embodiments, the heterologous protein is a tag, such as a fluorescent protein. Such labels can further facilitate tracking and/or visualization of the antibody or gp41.

In some embodiments, the detecting comprises analyzing the gp41 contacted in steps (a) and (b) using a fluorescent polarization assay, and wherein a change in the fluorescent polarization signal relative to a control or reference level indicates that the agent modulates the activity of MPER. Means of detecting such labels are well known to those of skill in the art. Thus, for example, radiolabels can be detected, e.g., using photographic film or scintillation counters, fluorescent markers can be detected using a photodetector to detect emitted light. Enzymatic labels are typically detected, e.g., by providing the enzyme with an enzyme substrate and detecting the reaction product produced by the action of the enzyme, e.g., on the enzyme substrate, and calorimetric labels can be detected by visualizing the colored label.

The fluorescent polarization signal can be determined by, e.g., a plate reader, confocal microscope, or any other detection method known in the art.

It is specifically contemplated herein that other methods of detecting a modulation in MPER activity can be used. Additional assays that can be used include but are not limited to enzyme-linked immunosorbent assay (ELISA), Western Blot, immunohistochemistry, protein-conjugated quantum dots, proteomics, mass spectrometry, FRET, Edman degradation, Matrix Assisted Laser Desorption/Ionization (MALDI), scanning electron microscopy, super resolution microscopy, transmission electron microscopy, or any other assay that identifies proteins, protein structure, composition, interactions, or localization known in the art.

The MPER used for screening and identifying an agent that modulates the activity of the MPER as described in the working examples is derived from or expressed by Glade A HIV-1 isolate 92UG037.8. The amino acid sequence for the Glade A HIV-1 isolate 92UG037.8 MPER is the following: ELLELDKWANLWNWFDISNWLWYIK (SEQ ID NO: 7). However, this sequence is non-limiting and any sequence for the MPER known in the art can be used to identify a test agent.

As used herein, the term "test agent" refers to agents, compounds, and/or compositions that are to be screened for their ability to modulate MPER activity and/or prevent cell-cell fusion by the Env. Test agents may include a wide variety of different compounds, including chemical compounds, mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, viruses, or animal cells; animal tissues; naturally occurring or synthetic compositions; and any combinations thereof. In some embodiments, the test agent is a small molecule.

The number of possible test agents runs into millions. Methods for developing small molecule, polymeric and genome based libraries are described, for example, in Ding, et al. *J Am. Chem. Soc.* 124: 1594-1596 (2002) and Lynn, et al., *J Am. Chem. Soc.* 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods provided herein. Chemical compound libraries such as those from NIH Roadmap, Molecular Libraries Screening Centers Network (MLSCN) can also be used.

Comprehensive list of compound libraries can be found on the web, for example, at <www.broad.harvard.edu/chembio/platform/screening/compound_libraries/index.htm>.

A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test agents may be provided free in solution, or may be attached to a carrier, or a solid support, e.g., beads. A number of suitable solid supports may be employed for immobilization of the test agents. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods provided herein, test agents may be screened individually, or in groups. Group screening is particularly useful where hit rates for effective test agents are expected to be low such that one would not expect more than one positive result for a given group.

Generally, compounds can be tested at any concentration that can inhibit and/or decrease activity of MPER. In some embodiments, compounds are tested at a concentration in the range of from about 0.1 nM to about 1000 mM. Preferably the compound is tested in the range of from about 0.1 μM to about 10 μM.

In some embodiments, screening assay further comprises selecting the compound that inhibits or reduces MPER activity. The test agent can inhibit or reduce MPER activity by at least 10%, 20%, 30%, 40%, 50%, 50%, 70%, 80%, 90%, 95% or more relative to a control.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U. S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds. The key labware or testing vessel of HTS is the microtiter plate: a small container, usually disposable and made of plastic, that features a grid of small, open divots called wells. Modern microplates for HTS generally have either 384, 1536, or 3456 wells. These are all multiples of 96, reflecting the original 96 well microplate with 8×12 9mm spaced wells.

To prepare for an assay, the researcher fills each well of the plate with the appropriate reagents that he or she wishes to conduct the experiment with. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as fluorescent, colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound selected by the screening assay provided herein. It is to be understood that analogs, derivatives, and isomers of the compounds selected by the screening assays provided herein are also claimed herein.

Methods of Treating Viral Infections

The compounds and agents, or compositions and pharmaceutical compositions described herein can be used to treat a subject having a viral infection, or prevent a subject from having a viral infection. Thus, provided herein are methods for treating and/or preventing a viral infection in a subject. Methods include administering to a subject in need thereof (e.g., a subject having or at risk of having a viral infection) an agent that inhibits the MPER of an Env.

One aspect herein is a method of treating or preventing a viral infection comprising administering to a subject having or at risk of having a viral infection any compound, composition thereof, or pharmaceutical composition thereof that inhibits the MPER of a viral Env. Another aspect herein is a method of treating or preventing a viral infection comprising administering to a subject having or at risk of having a viral infection an agent that inhibits the MPER of a viral Env.

In one embodiment, the subject has not been previously diagnosed as having a viral infection.

One aspect herein is a method of treating a viral infection comprising (a) diagnosing a subject as having a viral infection, and (b) administering to a subject having a viral infection a compound or agent, or composition or pharmaceutical composition thereof, that inhibits the MPER of a viral Env.

One aspect herein is a method of treating a viral infection comprising (a) receiving the results of an assay that diagnoses a subject as having a viral infection, and (b) administering to a subject having a viral infection a compound or agent, or composition or pharmaceutical composition thereof, that inhibits the MPER of a viral Env.

A skilled clinician can diagnose a subject as having a viral infection via detection of symptoms of a viral infection, such as, fatigue, loss of immune function, vomiting, diarrhea, headaches, gastrointestinal upset, nausea, weight loss, etc. However, some subjects can remain asymptomatic and/or carry the virus or the disease. Further, viral infections can further be diagnosed via clinical tests of a biological sample from a subject, e.g., blood, saliva, spinal fluid, or tissue biopsy. Clinical tests are known in the art and include, but are not limited to, antibody tests, viral antigen detection tests, viral culture, and viral DNA/RNA detection tests. Clinical tests useful in diagnosing a viral infection are further reviewed in, e.g., U.S. Pat. Nos 6,432,633; and 5,173,399, the contents of which are incorporated herein by reference in their entireties.

One aspect herein is a method of preventing a viral infection comprising (a) diagnosing a subject as being at risk for having a viral infection and (b) administering to a subject at risk of having a viral infection a compound or agent, or composition or pharmaceutical composition thereof, that inhibits the MPER of a viral Env.

One aspect herein is a method of treating a viral infection comprising (a) receiving the results of an assay that diagnoses a subject as being at risk for having a viral infection, and (b) administering to a subject diagnosed as being at risk of having a viral infection a compound or agent, or composition or pharmaceutical composition thereof, that inhibits the MPER of a viral Env.

Risks factors for having or developing a viral infection include exposure to the virus, exposure or contact with a subject infected with a virus, exposure to contaminated surfaces contacted with a virus, contact with a biological sample or bodily fluid from a subject infected by a virus, sexual intercourse with a subject infected by a virus, needle sharing, blood transfusions, drug use, and any other risk factor known in the art to transmit a virus from one subject to another. Risk factors for a subject can be evaluated, e.g., by a skilled clinician or by the subject.

Exemplary viral infections include, but are not limited to, retroviruses such as human immunodeficiency virus-1 (HIV-1), HIV-2; herpesviruses, poxviruses, hepadnaviruses, flavivirus, coronavirus, hepatitis D, orthomyxovirus, paramyxovirus, rhabdovirus, Rabies virus, bunyavirus, filovirus, or any other viral infection known in the art. Preferably, the viral infection is an infection caused by enveloped viruses. That is, viruses that comprise viral envelopes covering their protective protein capsids. In one embodiment, the viral infection is a retroviral infection caused by a retrovirus. As used herein, "a retrovirus" refers to is a single-stranded positive-sense RNA virus with a DNA intermediate and as an obligate parasite, that targets a host cell in a subject. Retroviruses are generally characterized by their structure which comprises an envelope (Env), RNA (e.g., dimer RNA), and proteins (e.g., group-specific antigen (gag) proteins, protease, pol proteins, and Env proteins). Non-limiting example of retroviruses include human immunodeficiency virus (HIV) and human T cell leukemia virus (HTLV). Retroviruses such as HIV can be lethal, due to the immunosuppression of the host subject.

Methods of Treating HIV Infection

In one aspect, the compounds, agents, or compositions or pharmaceutical compositions thereof described herein can be used to treat or prevent an HIV infection. Accordingly, one aspect is a method of treating or preventing an HIV infection comprising administering to a subject having or at risk of having a viral infection an agent that inhibits the MPER of a viral Env. In some embodiments, the HIV infection is a HIV-1 infection or an HIV-2 infection. In some embodiments, the viral infection results in acquired immune deficiency syndrome (AIDS).

There are two types of HIV, HIV-1 and HIV-2. HIV-1 is the most common form of infection because it is more virulent and infective than HIV-2. HIV-2 is generally confined to areas of West Africa due to its poor capacity for transmission. It is to be understood that "HIV" refers to all strains and/or groups of HIV, and types and subtypes of HIV, e.g., HIV-1 and HIV-2. There are two types of HIV, HIV-1 and HIV-2. HIV-1 is the most common form of infection because it is more virulent and infective than HIV-2. HW-2 is generally confined to areas of West Africa due to its poor capacity for transmission. It is to be understood that "HIV" refers to all strains and/or groups of HIV, and types and subtypes of HIV, e.g., HIV-1 and HIV-2.

HIV infection can be transmitted from one subject to another by sexual contact, blood transfusions, blood-borne transmission (e.g., needle sharing, IV drug use), and mother to child transmission (e.g., during pregnancy, birth, or breast-feeding). Individuals infected with HIV develop specific antibodies (e.g., seroconvert) within three to twelve weeks after the initial infection. HIV is generally diagnosed by a skilled clinician, for example, via a clinical test for HIV-RNA or p24 antigen in the serum, saliva, or urine from a subject suspected of having an HIV infection.

In some embodiments, the viral envelope is the HIV-1 or HIV-2 Env.

HIV infects components of the subject's immune system such as CD4+ T cells, macrophages, and dendritic cells by destroying the immune cells of the host subject. The virus fuses to the target cell (e.g., a host cell) and begins replicating via a reverse transcriptase enzyme to converts the single stranded, positive-sense RNA of the viral genome to double stranded DNA. The resulting viral DNA is then imported into the host cell nucleus and integrated into the cellular DNA by a virally encoded integrase and host co-factors. Once integrated, the virus may become latent or transcribed to produce new RNA genomes and viral proteins that are released from the host cell as new viral particles.

The HIV infection has several clinical stages described by the World Health Organization (WHO) and US Center for Disease Control and Prevention. Stage I of the HIV infection is characterized by lymph node enlargement and an increase in CD4+ T cell count (e.g., greater than 500 per microliter). Stage II is characterized by increased or recurrent upper respiratory tract infections. Stage III is characterized by chronic diarrhea for longer than one month, secondary infections (e.g., tuberculosis), and loss of CD4+ T cells (e.g., CD4+ T cell count less than 350 per microliter). Stage IV is when the subject has developed AIDS. AIDS is characterized by toxoplasmosis of the brain, candidiasis of the esophagus, trachea, bronchi, lungs, Kaposi's sarcoma, and a CD4+ T cell count less than 200 per microliter. AIDS is considered a terminal disease. A subject at risk for having an HIV infection is a subject that has been exposed to another subject with HIV through the commonly known modes of viral transmission for HIV, as described herein.

Current treatment for HIV and AIDS include combination antiretroviral therapy (cART) Non-limiting examples of cART include nucleoside/nucleotide reverse transcriptase inhibitors (NRTIs), non-nucleoside reverse transcriptase inhibitors (NNRTIs), protease inhibitors (PIs), fusion inhibitors (FIs), coreceptor inhibitors (CRIs) and integrase inhibitors (INIs). All of which target the replication or integration of HIV.

In some circumstances, HIV is resistant to treatment or treatment currently available in the clinical setting is not effective in preventing and treating the symptoms of HIV infection or AIDS. In one embodiment, the viral infection is an HIV infection and is resistant to at least one HIV treatment. Resistance to a treatment by a virus, e.g., the capacity of the virus to evade the treatment and the virus and viral infection to persist, can be assessed by a skilled clinician, for example, by assessing the development or regression of symptoms associated with the infection.

In some embodiments, the HIV-1 infection is resistant to an inhibitor of HIV-1 fusion to a target cell. Exemplary inhibitors of HIV-1 fusion include but are not limited to is Maravirox, Enfuvirtide, Sifuvirtide, Albuvirtide. Enfuvirtide, is a 36-residue peptide derived from HIV-1 gp41, is the first and still the only fusion inhibitor approved by FDA. It is now rarely used by HIV-1 infected patients, however, because of its numerous disadvantages and drug-resistance. See for example, Poveda et al. *J Clin Vivol* (2005).

Target Cells

Various aspects described herein are directed to inhibiting Env fusion to a target cell. As used herein, "a target cell" refers to a cell within the host subject that is contacted by a virus, or becomes physically attached to a virus via viral fusion (e.g., the merging of viral membrane and the target cell membrane), as described herein. Viral fusion is mediated via transmembrane proteins on the target cell and the virus, and allows for the passage of genetic material from the virus to the target cell. Thus, a target cell is a cell that can be physically attached (e.g., fused) to e.g., a glycoprotein, glycoprotein fragment, or glycoprotein envelope spike (e.g., gp120 and gp41 heterodimers) of a virus. The target cell express cells surface proteins or receeptors that facilitate the fusion of a viral envelope protein to its extracellular surface. Exemplary cell surface proteins and receptors expressed on a target cell that can bind and attach to a viral envelope include, but are not limited, to cluster of differentiation 4 (CD4), CC chemokine receptor 4 (CC4), CC chemokine receptor 5, C-X-C chemokine receptor type 4 (CXCR4), CC chemokine receptor 3 (CC3), nicotinic acetylcholine receptor (nAChR), the neuronal cell adhesion molecule (NCAM), and the p75 neurotrophin receptor (p75NTR), phosphate transporter 2 (Pit2), malonyl CoA-acyl carrier protein transacylase (MCAT), feline leukemia virus subgroup C receptor-related proteins (FLVCRs), xenotropic and polytropic retrovirus receptor 1 (XPR1), TVA, TVB, biliverdin reductase (BLVR), hyaluronidase-2 (HYAL2). One skilled in the art can identify a target cell by determining is a cell expresses any of the cell surface proteins or receptors via, e.g., fluorescent microscopy to visualize the cell surface protein or receptors, or via sorting for cells expressing these cell surface proteins or receptors via fluorescence activated cell sorting (FACS) using standard protocols for sorting by cell surface proteins. One can additionally, e.g., perform viral fusion assays as described herein to determine if a virus can attach and fuse a cell, thus identifying a target cell.

Exemplary target cells include, but are not limited to, an epithelial cell, leukocyte, a lymphocyte, a T cell, or a CD4+ T cell. A target cell can be human cell or mammal cell, for example, a canine, avian, feline, equine, bovine, porcine, primate, rodent, or bat cell.

Compounds and Agents

Described herein are compounds and agents that target the MPER of a glycoprotein (e.g., gp41) on a viral envelope (Env), e.g., HIV-1 Env. The compounds and agents described herein can inhibit the levels or activity of the viral Env to prevent a viral infection, in part, by inhibiting fusion of the viral Env to a target cell.

In one aspect of any of the embodiments, described herein are compounds of Formula (I):

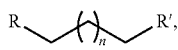

FORMULA (I)

and pharmaceutically acceptable salts thereof,
wherein:
n is an integer from 3 to 14;
R and R' are independently selected from the group consisting of:
(i) Formula (II):

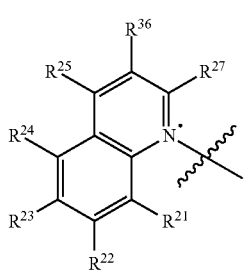

FORMULA (II)

wherein:
$R^{11}$, $R^{12}$, $R^{13}$, $R^{14}$ and $R^{15}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and $R^{16}$ and $R^{17}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{26}$ and $R^{27}$, together with the carbon atoms they are attached to, form a 5-8 membered cyclyl, heterocyclyl, aryl or heteryaryl, each of which can be optionally substituted with 1, 2, 3, or more independently selected substituents;

(ii) Formula (III):

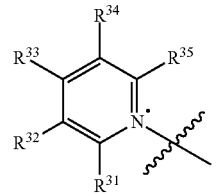

FORMULA (III)

wherein:
$R^{31}$, $R^{32}$ and $R^{33}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and $R^{34}$ and $R^{135}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{34}$ and $R^{35}$, together with the carbon atoms they are attached to, form a 5-8 membered cyclyl, heterocyclyl, aryl or heteryaryl, each of which can be optionally substituted with 1, 2, 3, or more independently selected substituents; and pharmaceutically acceptable salts thereof; and (iii) Formula (IV):

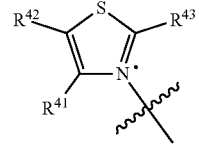

FORMULA (IV)

wherein:
$R^{41}$, $R^{42}$, and $R^{43}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl.

In some embodiments of the various aspects disclosed herein, the compound of Formula (I) is not dequalinium.

In some embodiments, a compound of Formula (I), further comprises an anion. For example, an anion for forming a pharmaceutically acceptable salt. Exemplary anions include, but are not limited to, acetate, aspartate, benzenesulfonate, benzoate, besylate, bicarbonate, bitartrate, bromide, camsylate, carbonate, chloride, citrate, decanoate, edetate, estolate, esylate, fumarate, gluceptate, gluconate, glutamate, glycolate, glycollylarsanilate, hexanoate, hexylresorcinate, hydrabamine, hydroxynaphthoate, iodide, isethionate, isethionate, lactate, lactobionate, malate, maleate, mandelate, mesylate, methylbromide, methylnitrate, methylsulfate, mucate, napsylate, nitrate, octanoate, oleate, pamoate, pantothenate, phosphate, polygalacturonate, propionate, salicylate, stearate, subacetate, succinate, sulfate, tartrate, teoclate, tosylate, and triethiodide. In some embodiments, the anion is halogen, e.g., Cl$^-$, Br$^-$, F$^-$ or and I$^-$.

In compounds of Formula (I), n can be any integer from 3 to 14. For example, n can be 4, 5, 6, 7, 8, 9, 10, 11, 12 or 13. In some embodiments, n is 5, 6, 7, 8, 9, 11, 11 or 12, for example, n is 6, 7, 8, 9, 10 or 11. Preferably n is 7, 8, 9 or 10.

In compounds of Formula (I), R and R' can be same or different. In some embodiments, R and R' are of Formula (II). Preferably R and R' are same.

In some compounds of Formula (I), $R^{21}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{21}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{21}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{21}$ is H or halogen, e.g., Cl, Br, F, or I. Preferably, $R^{21}$ is H.

In some compounds of Formula (I), $R^{22}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{22}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{22}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{22}$ is H or halogen, e.g., Cl, Br, F, or I. Preferably, $R^{22}$ is H or Cl.

In some compounds of Formula (I), $R^{23}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{23}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{23}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{23}$ is H or halogen, e.g., Cl, Br, F, or I. Preferably, $R^{23}$ is H or Br.

In some embodiments, at least one of, e.g., one or both, $R^{22}$ and $R^{23}$ are not H. For example, one of $R^{22}$ and $R^{23}$ is H and other is not H. In some embodiments, one of $R^{22}$ and $R^{23}$ ais halogen and the other is H. For example, $R^{22}$ is halogen, e.g., Br, Cl, F or I, and $R^{23}$ is H. Preferably $R^{22}$ is Cl and $R^{23}$ is H. In another non-limiting example, $R^{23}$ is halogen, e.g., Br, Cl, F or I, and $R^{22}$ is H. Preferably $R^{23}$ is Br and $R^{22}$ is H.

In some compounds of Formula (I), $R^{24}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{24}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{24}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{24}$ is H or halogen, e.g., Cl, Br, F, or I. Preferably, $R^{24}$ is H.

In some compounds of Formula (I), $R^{25}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{25}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{25}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{25}$ is H, amino, alkyl amino or dialkylamino. Preferably $R^{25}$ is an amino, e.g., $NH_2$.

In some compounds of Formula (I), $R^{26}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{26}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{26}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{26}$ is H or halogen, e.g., Cl, Br, F, or I. Preferably, $R^{26}$ is H or Br.

In some compounds of Formula (I), $R^{27}$ can be selected from the group consisting of —H, alkyl, haloalkyl, hydroxyl, alkoxy, amino, alkylamino, dialkylamino, carboxyl, halogen, nitro, cyano, thiol, and thiolalkoxy. In some embodiments, $R^{27}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{27}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{27}$ is H or alkyl, e.g., $C_1$-$C_6$alkyl, such as methyl, ethyl, propyl, isopropyl, butyl, pentyl or hexyl. Preferably, $R^{27}$ is H or methyl.

In some embodiments of the various aspects disclosed herein, $R^{26}$ and $R^{27}$, together with the carbon atoms they are attached to, form a 4-8 membered cyclyl, heterocyclyl, aryl or heteryaryl, each of which can be optionally substituted with 1, 2, 3, or more independently selected substituents. For example, $R^{26}$ and $R^{27}$, together with the carbon atoms they are attached to, form a 4-8 membered cyclyl, optionally substituted with 1, 2, 3, 4 or more independently selected substituents. In some embodiments, $R^{26}$ and $R^{27}$, together with the carbon atoms they are attached to, form a 5-membered cyclyl, optionally substituted with 1, 2 or 3 independently selected substituents.

In some compounds of Formula (I), $R^{31}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{31}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{31}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{31}$ is H or halogen, e.g., Cl, Br, F, or I. Preferably, $R^{31}$ is H.

In some compounds of Formula (I), $R^{32}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{32}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{32}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{32}$ is H or halogen, e.g., Cl, Br, F, or I. Preferably, $R^{32}$ is H.

In some compounds of Formula (I), $R^{33}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{33}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{33}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{33}$ is H, amino, alkyl amino or dialkylamino. Preferably $R^{33}$ is an amino, e.g., $NH_2$.

In some compounds of Formula (I), $R^{34}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{34}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{34}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{34}$ is H or halogen, e.g., Cl, Br, F, or I. Preferably, $R^{34}$ is H or Br.

In some compounds of Formula (I), $R^{35}$ can be selected from the group consisting of —H, alkyl, haloalkyl, hydroxyl, alkoxy, amino, alkylamino, dialkylamino, carboxyl, halogen, nitro, cyano, thiol, and thiolalkoxy. In some embodiments, $R^{35}$ is H, halogen, $C_1$-$C_6$alkyl, halo($C_1$-$C_6$) alkyl, amino, $C_1$-$C_6$alkylamino, or di($C_1$-$C_6$alkyl)amino. For example, $R^{35}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{35}$ is H or alkyl, e.g., $C_1$-$C_6$alkyl, such as methyl, ethyl, propyl, isopropyl, butyl, pentyl or hexyl. Preferably, $R^{35}$ is H or methyl.

In some embodiments of the various aspects disclosed herein, $R^{34}$ and $R^{35}$, together with the carbon atoms they are attached to, form a 4-8 membered cyclyl, heterocyclyl, aryl or heteryaryl, each of which can be optionally substituted with 1, 2, 3, or more independently selected substituents. For example, $R^{34}$ and $R^{35}$, together with the carbon atoms they are attached to, form a 4-8 membered cyclyl, optionally substituted with 1, 2, 3, 4 or more independently selected substituents. In some embodiments, $R^{26}$ and $R^{27}$, together with the carbon atoms they are attached to, form a 5-membered cyclyl, optionally substituted with 1, 2 or 3 independently selected substituents.

In some compounds of Formula (I), $R^{41}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{41}$ is H, halogen, C1-C6alkyl, halo(C1-C6)alkyl, amino, $C_1$-$C_6$alkylamino, or di(C1-C6alkyl)amino. For example, $R^{41}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{41}$ is $C_1$-$C_6$alkyl, for example, methyl, ethyl, n-propyl, isopropyl, n-butyl, isobutyl, sec-butyl, tert-butyl, pentyl, hexyl, and the like. Preferably, $R^{41}$ is methyl.

In some compounds of Formula (I), $R^{42}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{41}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{42}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{42}$ is $C_1$-$C_6$alkyl, for example, methyl, ethyl, n-propyl, isopropyl, n-butyl, isobutyl, sec-butyl, tert-butyl, pentyl, hexyl, and the like. Preferably, $R^{42}$ is ethyl.

In some compounds of Formula (I), $R^{43}$ can be selected from the group consisting of H, alkyl, haloalkyl, hydroxyl, alkoxy, amino, alkylamino, dialkylamino, carboxyl, halogen, nitro, cyano, thiol, and thiolalkoxy. In some embodiments, $R^{32}$ is H, halogen, $C_1$-$C_6$alkyl, halo($C_1$-$C_6$)alkyl, amino, $C_1$-$C_6$alkylamino, or di($C_1$-$C_6$alkyl)amino. For example, $R^{32}$ can be H, halogen, methyl, ethyl, propyl, isopropyl, butyl, pentyl, hexyl, $CF_3$, $NH_2$, $CH_3NH$, $CH_3CH_2NH$, $CH_3CH_2CH_2NH$, $(CH_3)_2CHNH$, $(CH_3)_2N$, or $(CH_3CH_2)_2N$. In some embodiments, $R^{32}$ is H, $C_1$-$C_6$alkyl, or halogen, e.g., Cl, Br, F, or I. Preferably, $R^{43}$ is H Some exemplary compounds of Formula (I) include, but are not limited to, the following:
(i) R and R' are the same; $R^{21}$, $R^{22}$, $R^{23}$, and $R^{24}$ are H; $R^{25}$ is amino; $R^{26}$ and $K^{27}$ together with the carbon atoms they are attached to form a 5-membered cyclyl; and n is 4, 6, 8, 10;
(ii) R and R' are the same; $R^{21}$, $R^{22}$, $R^{23}$, $R^{24}$ and $R^{26}$ are H; $R^{25}$ is amino; $R^{27}$ is methyl; and n is 4, 6, 8, 10 or 12;
(iii) R and R' are the same; $R^{21}$, $R^{22}$, $R^{23}$, $R^{24}$, $R^{26}$ and $R^{27}$ are H; $R^{25}$ is amino; and n is 4, 6, 8, 1 0;
(iv) R and R' are the same; $R^{21}$, $R^{23}$, $R^{24}$, $R^{26}$ and $R^{27}$ are H; $R^{22}$ is halogen, e.g., Cl; $R^{25}$ is amino; and n is 4, 6, 8, 10;
(v) R and R' are the same; $R^{21}$, $R^{22}$, $R^{24}$, $R^{26}$ and $R^{27}$ are H; $R^{23}$ is halogen, e.g., Br; $R^{25}$ is amino; and n is 4, 6, 8, 10;
(vi) R and R' are the same; $R^{21}$, $R^{22}$, $R^{23}$, $R^{24}$, and $R^{27}$ are H; $R^{26}$ is halogen, e.g., Br; $R^{25}$ is amino; and n is 4, 6, 8, 10; and
(vii) R and R' are the same; $R^{21}$, $R^{22}$, $R^{23}$, $R^{24}$, $R^{25}$, $R^{26}$ and $R^{27}$ are H; and n is 4, 6, 8, 10.

In some embodiments of the various aspects disclosed herein, the compound of Formula (I) is S2C3, where R and R' are the same; $R^{21}$, $R^{22}$, $R^{23}$, and $R^{24}$ are H; $R^{25}$ is amino; $R^{26}$ and $R^{27}$, together with the carbon atoms they are attached to form a 5-membered cyclyl; and n is.

In some embodiments of the various aspects disclosed herein, the compound of Formula (I) is S 1 C1, where R and R' are the same; $R^{21}$, $R^{22}$, $R^{23}$, $R^{24}$ and $R^{26}$ are H; $R^{25}$ is amino; $R^{27}$ is methyl; and n is 4.

In some embodiments of the various aspects disclosed herein, the compound of Formula (I) is S 1 C2, where R and R' are the same; $R^{21}$, $R^{22}$, $R^{23}$, $R^{24}$, and $R^{26}$ are H; $R^{25}$ is amino; $R^{27}$ is methyl; and n is 6.

In some embodiments of the various aspects disclosed herein, the compound of Formula (I) is S 1 C4, where R and R' are the same; $R^{21}$, $R^{22}$, $R^{23}$, $R^{24}$ and $R^{26}$ are H; $R^{25}$ is amino; $R^{27}$, is methyl; and n is 10.

In some embodiments of the various aspects disclosed herein, the compound of Formula (I) is S 1 C5, where R and R' are the same; $R^{21}$, $R^{22}$, $R^{23}$, $R^{24}$ and $R^{26}$ are H; $R^{25}$ is amino; $R^{27}$ is methyl; and n is 12.

In some embodiments of the various aspects disclosed herein, the compound of Formula (I) is S2C1, where R and R' are the same; $R^{21}$, $R^{22}$, $R^{23}$, $R^{24}$, $R^{26}$ and $R^{27}$ are H; $R^{25}$ is amino; and n is 8.

In some embodiments of the various aspects disclosed herein, the compound of Formula (I) is S2C6, where R and R' are the same; $R^{21}$, $R^{22}$, $R^{23}$, $R^{24}$, $R^{26}$ and $R^{27}$ are H; $R^{25}$ is amino; and n is 8.

In some embodiments of the various aspects disclosed herein, the compound of Formula (I) is 52C7, where R and R' are the same; $R^{21}$, $R^{22}$, $R^{24}$, $R^{26}$ and $R^{27}$ are H; $R^{23}$ is Br; $R^{25}$ is amino; and n is 8.

In some embodiments of the various aspects disclosed herein, the compound of Formula (I) is S2C8, where R and R' are the same; $R^{21}$, $R^{22}$, $R^{23}$, $R^{24}$, and $R^{27}$ are H; $R^{26}$ is Br; $R^{25}$ is amino; and n is 8.

In some embodiments of the various aspects disclosed herein, the compound of Formula (I) is S2C1 0, where R and R' are the same; $R^{21}$, $R^{22}$, $R^{23}$, $R^{24}$, $R^{25}$, $R^{26}$ and $R^{27}$ are H; and n is 8.

In some embodiments of the various aspects disclosed herein, the compound of Formula (I) is S2C9, where R and R' are the same; $R^{31}$, $R^{32}$ and $R^{34}$ are H; $R^{33}$ is $NH_2$; and $R^{35}$ is methyl.

In some embodiments of the various aspects disclosed herein, the compound of Formula (I) is S2C1 1, where R and R' are the same; $R^{41}$ is methyl; $R^{42}$ is ethyl; and $R^{43}$ is H.

The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e. g. , —$CH_2O$— is equivalent to —$OCH_2$—.

The term "alkyl" as used herein refers to a linear, branched, or cyclic saturated hydrocarbon group typically although not necessarily containing 1 to about 24 carbon atoms, preferably 1 to about 12 carbon atoms, more preferably 1 to about 6 carbon atoms or a lower alkyl, such as methyl, ethyl, n-propyl, isopropyl, n-butyl, isobutyl, sec-butyl, tert-butyl, pentyl, hexyl, and the like, as well as cycloalkyl groups such as cyclopropyl, cyclobutryl, cyclopentyl, cyclohexyl, cycloheptyl, cyclooctyl and the like. The term "cycloalkyl" intends a cyclic alkyl group, typically having 3 to 10, preferably 3 to 8, carbon atoms. The term "substituted alkyl" refers to alkyl substituted with one or more substituent groups, and the terms "heteroalkyl" and "heteroatom-containing alkyl" refer to alkyl in which at least one carbon atom is replaced with a heteroatom. The term "haloalkyl" as used herein refers to an alkyl structure with at least one substituent of fluorine, chorine, bromine or iodine, or with combinations thereof. If not otherwise indicated, the term "alkyl" includes linear, branched, cyclic, unsubstituted, substituted, and/or heteroatom-containing alkyl, respectively.

The term "alkenyl" as used herein refers to a linear, branched, or cyclic hydrocarbon group of 2 to about 16 carbon atoms containing at least one double bond, such as ethenyl, n-propenyl, isopropenyl, n-butenyl, isobutenyl, n-pentenyl, iso-pentenyl, hexenyl, heptenyl, octenyl, decenyl, tetradecenyl, hexadecenyl, eicosenyl, tetracosenyl, and the like. Preferred alkenyl groups herein contain 2 to about 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl, respectively.

The term "alkynyl" as used herein refers to a linear or branched-chain hydrocarbon group having one or more carbon-carbon triple-bonds and having from 2 to about 8 carbon atoms. Examples of alkynyl groups include ethynyl, propynyl, butynyl, pentynyl and the like.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to an alkyl structure with at least one substituent of fluorine, chorine, bromine or iodine, or with combinations thereof. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkyl)(alkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

Exemplary alkylamino includes, but is not limited to, NH($C_1$-$C_{10}$alkyl), such as —$NHCH_3$, —$NHCH_2CH_3$, —$NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N(CH($CH_3$)$_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxy" and "hydroxyl" mean the radical —OH.

The terms "alkoxyl" or "alkoxy" as used herein refers to an alkyl group, as defined above, having an oxygen radical attached thereto, and can be represented by one of —O- alkyl, —O-alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term "nitro" means the radical —NO$_2$.

The term "aryl" refers to monocyclic, bicyclic, or tricyclic fused aromatic ring system. Preferred aryl groups contain 5 to 24 carbon atoms, and particularly preferred aryl groups contain 5 to 14 carbon atoms. "Substituted aryl" refers to an aryl moiety substituted with one or more, (e.g., one, two, three, four or more) substituent groups. The terms "heteroatom-containing aryl" and "heteroaryl" refer to aryl substituents in which at least one carbon atom is replaced with a heteroatom such as oxygen, nitrogen and sulfur. The term "heteroaryl" includes ring systems such as pyridine, quinoline, furan, thiophene, pyrrole, imidazole and pyrazole and the like. Exemplary aryl and/or heteroaryl groups include, but are not limited to phenyl, 1-naphthyl, 2-naphthyl, biphenyl, pyridine, quinoline, furan, thiophene, pyrrole, imidazole, pyrazole, diphenylether, diphenylamine, benzophenone, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "cyclyl" or "cycloalkyl" refers to saturated or partially unsaturated cyclic hydrocarbon groups having 3 to 12 carbons, for example, 3 to 8 carbons, and for example, 3 to 6 carbons. The cycloalkyl can be monocyclic, bicyclic, or polycyclic. The terms "bicyclic" and "tricyclic" refers to fused, bridged, or joined by a single bond polycyclic ring assemblies. The cycloalkyl group additionally can be optionally substituted, e.g., with 1, 2, 3, or 4 substituents. Exemplary C3-C$_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo [2.2.1]hept-1-yl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S—(O)$_2$—, —OS(O)$_2$—, and —SS—, wherein R$^N$ is H or a further substituent.

The terms "alkylthio" and "thioalkoxy" refer to an alkoxy group, as defined above, where the oxygen atom is replaced with a sulfur. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, dialkylamino, alkylcarbanoyl, alkylene, alkylidene, alkylthio, alkynyl, amide, amido, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, heteroaryl, heterocyclyl, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which can optionally also be substituted or unsubstituted. In some cases, two substituents, together with the carbon(s) to which they are attached to, can form a ring.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention. In addition to the chemical compounds and structures described herein, the agents that inhibit MPER include but are not limited to a small molecule, an antibody reagent, a peptide, a genome editing system, an antisense oligonucleotide, or an RNAi.

An "agent" as used herein is a chemical molecule of synthetic or biological origin. In the context of the present invention, an agent is generally a molecule that can be used in a pharmaceutical composition.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The agents described herein can be antibody reagents. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., *Eur J. Immunol.* 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include broadly neutralizing antibodies, midibodies, nanobodies, humanized antibodies, chimeric antibodies, and the like. The antibody reagent described herein can specifically bind to any one of the glycoproteins or fragments thereof as described herein. Accordingly, the antibody reagent can specifically bind to the MPER of gp41 on the HIV-1 Env. The antibody reagent can specifically bind to any one of the amino acid sequences of SEQ ID NO: 2-SEQ ID NO: 5.

In some embodiments, the agent is a humanized, monoclonal antibody or antigen-binding fragment thereof, or an antibody reagent. As used herein, "humanized" refers to antibodies from non-human species (e.g., mouse, rat, sheep, etc.) whose protein sequence has been modified such that it increases the similarities to antibody variants produce naturally in humans. In some embodiments, the humanized antibody is a humanized monoclonal antibody. In some embodiments, the humanized antibody is a humanized polyclonal antibody. In some embodiments, the humanized antibody is for therapeutic use.

Non-limiting examples of antibodies that disrupt viral Env fusion include broadly neutralizing antibodies (bnAbs) such as 2F5, 4E10, Z13e1, and 10E8. Antibodies or antibody fragments that target gp41 of a viral Env can also be used. Broadly neutralizing antibodies of HIV are further discussed in, e.g., U.S. Pat. No. 7,342,090 which is incorporated herein by reference in its entirety.

The agents described herein can also be polypeptides that block viral Env fusion to a target cell. As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

In some embodiments, cell fusion of a cell (e.g., a target cell) and the viral envelope (e.g., HIV-1 Env) is decreased in a cell's genome using any genome editing system including, but not limited to, zinc finger nucleases, TALENS, meganucleases, and CRISPR/Cas systems that prevent the fusion of the Env. In one embodiment of any of the aspects, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference.

The agent described herein can further be an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides as described herein are complementary nucleic acid sequences designed to hybridize under cellular conditions to a gene. Thus, oligonucleotides are chosen that are sufficiently complementary to the target, i.e., that hybridize sufficiently well and with sufficient specificity in the context of the cellular environment, to give the desired effect.

In addition to antisense oligonucleotides, RNAi can be used to prevent Env fusion. The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA.

In some embodiments, the agent is dequalinium. Dequalinium has previously been used to treat malarial and anti-microbial diseases in subjects for many years (see for example, Maker et al., U.S. Pat. No. 4,946,849, which is incorporated herein by reference in its entirety). Generally, dequalinium possesses anti-microbial properties with broad activity.

Dequalinium contains two aminoquinolone head groups connected by a 10 carbon linker. The structure of dequalinium is as follows (See also FIG. 5D):

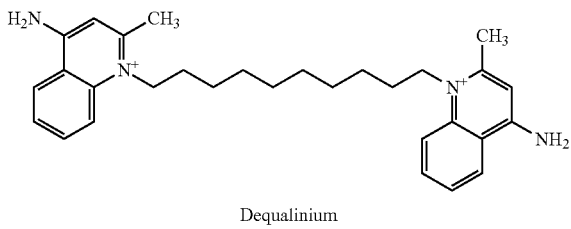 [SMILES: Cc1cc(N)c2ccccc2[n+]1CCCCCCCCCC[n+]1c(C)cc(N)c2ccccc21]

Dequalinium

Dequalinium possesses specificity for the glycoprotein 41 (gp41) of a viral Env (e.g., HIV-1 Env) and allows for the inhibition of Env cell-cell mediated fusion while minimizing cytotoxicity. Data shown herein in the Examples, dequalinium also targeted Env from multiple primary HIV-1 isolates of different clades, that supports that the small molecules described herein recognize a conserved binding site on the viral envelope gp41.

Structure-activity relationships described herein revealed that dequalinium analogs can also target gp41 of HIV-1 Env. Non-limiting examples of dequalinium analogs are described herein and shown, for example, in FIG. 9A, FIG. 9B, and FIG. 13.

Derivatives of the agents and compounds described herein can be used to inhibit Env fusion to a target cell. The term "derivative" as used herein means any chemical, conservative substitution, or structural modification of an agent. The derivative can improve characteristics of the agent or small molecule such as pharmacodynamics, pharmacokinetics, absorption, distribution, delivery, targeting to a specific protein (e.g., gp41 MPER), or efficacy. For example, for a small molecule, the derivative can consist essentially of at least one chemical modification to about ten modifications. The derivative can also be the corresponding salt of the agent. The derivative can be the pro-drug of the small molecule as provided herein.

In some embodiments, the derivative is selected from a group consisting of: Analog 1, Analog 2, Analog 3, Analog 4, 4-aminoquinaldine, C800, S1C1, S1C2, S1C4, S1C5, S2C1, S2C3, S2C6, S2C8, S2C9, S2C10, and S2C11. In some embodiments, the small molecule is a derivative of S2C3. In some embodiments, the small molecule is a derivative of C800.

One aspect provided herein is a composition or pharmaceutical composition comprising any of the agents described herein. In one embodiment, the composition further comprises a pharmaceutically acceptable carrier.

Pharmaceutical Salts

Compounds of Formula (I)-Formula (IV), agents described herein, or derivatives thereof can also include pharmaceutically acceptable salts thereof. As used herein, the term "pharmaceutically-acceptable salts" refers to the conventional nontoxic salts or quaternary ammonium salts of small molecules as disclosed herein, e.g., from non-toxic organic or inorganic acids. These salts can be prepared in situ in the administration vehicle or the dosage form manufacturing process, or by separately reacting a small molecule in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like Prodrugs In some embodiments, prodrugs of compounds of Formula (I) also fall within the scope of the invention. As used herein, a "prodrug" refers to a compound that can be converted via some chemical or physiological process (e.g., enzymatic processes and metabolic hydrolysis) to a compound of Formula (I). Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. I. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), contents of all of which are herein incorporated by reference in their entireties.

Compositions

One aspect herein provides a composition comprising any of the compounds described herein. Another aspect herein provides a composition comprising any of the agents described herein. In one embodiment, the composition further comprises a pharmaceutically acceptable carrier.

Another aspect herein provides a pharmaceutical composition comprising any of the compounds described herein. Yet another aspect herein provides a pharmaceutical composition comprising any of the agents described herein.

For administering to a subject, compounds of Formula (I) can be incorporated into pharmaceutical composition. As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Amount of the compound of Formula (I) in the pharmaceutical composition can be based on weight, moles, or volume. In some embodiments, the pharmaceutical composition comprises at least 0.0001% of the compound of Formula (I). In some embodiments, the pharmaceutical composition comprises at least 0.1% of the compound of Formula (I). In some embodiments, the pharmaceutical composition comprises at least 0.5% of the compound of Formula (I). In some embodiments, the pharmaceutical composition comprises at least 1% of the compound of Formula (I). In some embodiments, the pharmaceutical composition comprises at least 2% of the compound of Formula (I). In some embodiments, the pharmaceutical composition comprises at least 3% of the compound of Formula (I). In some embodiments, the pharmaceutical composition comprises at least 4% of the compound of Formula (I). In some embodiments, the pharmaceutical composition comprises at least 5% of the compound of Formula (I). In some embodiments, the pharmaceutical composition comprises at least 10% of the compound of Formula (I). In some embodiments, the pharmaceutical composition comprises 0.01%-99% of the compound of Formula (I). In some embodiments, the pharmaceutical composition comprises 0.05%-90% of the compound of Formula (I). In some embodiments, the pharmaceutical composition comprises 0.1%-85% of the compound of Formula (I). In some embodiments, the pharmaceutical composition comprises 0.5%-80% of the compound of Formula (I). In some embodiments, the pharmaceutical composition comprises 1%-75% of the compound of Formula (I). In some embodiments, the pharmaceutical composition comprises 2%-70% of the compound of Formula (I). In some embodiments, the pharmaceutical composition comprises 3%-65% of the compound of Formula (I). In some embodiments, the pharmaceutical composition comprises 4%-60% of the compound of Formula (I). In some embodiments, the pharmaceutical composition comprises 5%-50% of the compound of Formula (I).

Generally, a pharmaceutical composition of the invention comprises a therapeutically effective amount of a compound of Formula (I). In some embodiments, the pharmaceutical composition comprises a compound of Formula (I) at a concentration of about 0.0104 to 300 µM, or about 0.1 µM to 150 µM, or about 1 µM to 50 µM, or about 1 µM to 25 µM. The dosage can vary within this range depending upon the dosage form employed and the route of administration utilized.

It will also be appreciated that certain of the compound of Formula (I) can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of Formula (I) which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. The terms "physiologically tolerable carriers" and "biocompatible delivery vehicles" are used interchangeably. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the compound of Formula (I) together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the compound of Formula (I), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compound of Formula (I) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The compound of Formula (I) can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compound of Formula (I) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable formulations.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compound of Formula (I) with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or non-aqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Administration and Dosing

As used herein, the term "administering" refers to the placement of a therapeutic (e.g., a compound, composition, pharmaceutical composition, or an agent described herein) into a subject by a method or route which results in at least partial localization of the composition at a desired site such that desired effect is produced. A therapeutic (e.g., a compound, composition, pharmaceutical composition, or an agent described herein) described herein can be administered by any appropriate route known in the art including, but not limited to, oral or parenteral routes, including intravenous, intramuscular, parenteral, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrastemal injection and infusion. In preferred embodiments, the compositions are orally administered. Without limitations, oral administration can be in the form of solutions, suspensions, tablets pills, capsules, sustained-release formulations, oral rinses, powders and the like.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

In jurisdictions that forbid the patenting of methods that are practiced on the human body, the meaning of "administering" of a therapeutic to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of therapeutic includes both methods practiced on the human body and also the foregoing activities.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The term "effective amount" is used interchangeably with the term "therapeutically effective amount" or "amount sufficient" and refers to the amount of at least one therapeutic (e.g., a compound, composition, pharmaceutical composition, or an agent described herein) at dosages and for periods of time necessary to achieve the desired therapeutic result, for example, to "attenuate", reduce or stop at least one symptom of a viral infection, e.g., an HIV infection. For example, an effective amount using the methods as disclosed herein would be considered as the amount sufficient to reduce one or more symptoms of an HIV infection by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from HIV infection. Accordingly, the term "effective amount" or "therapeutically effective amount" as used herein refers to the amount of therapeutic (e.g., Formulas (I)-(IV)) of a pharmaceutical composition to alleviate at least one symptom of a disease. Stated another way, "therapeutically effective amount" of a therapeutic as disclosed herein is the amount of the therapeutic which exerts a beneficial effect on, for example, the symptoms of the disease (e.g., HIV infection). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of a HIV infection or at one related symptom thereof.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

As used herein, the term ED denotes "effective dose" and is used in connection with animal models. The term EC denotes "effective concentration" and is used in connection with in vitro models.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage of a therapeutic (e.g., a compound, composition, pharmaceutical composition, or an agent described herein) may be determined by a physician and adjusted, as necessary, to suit observed effects of the treatment. Generally, the compositions are administered so that the compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2mg/kg to 10mg/kg, 3mg/kg to 10mg/kg, 4mg/kg to 10mg/kg, 5mg/kg to 10mg/kg, 6mg/kg to 10mg/kg, 7mg/kg to 10 mg/kg, 8mg/kg to 10mg/kg, 9mg/kg to 10mg/kg, and the like. It is to be further understood that the ranges intermediate to the given above are also within the scope of this invention, for example, in the range 1 mg/kg to 10 mg/kg, dose ranges such as 2mg/kg to 8 mg/kg, 3mg/kg to 7 mg/kg, 4mg/kg to 6mg/kg, and the like.

In some embodiments, the compositions are administered at a dosage so that therapeutic (e.g., a compound, composition, pharmaceutical composition, or an agent described herein) or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the compound. The desired dose can be administered every day or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the agent or composition is administered continuously (e.g., at constant levels over a period of time). Continuous administration of an agent can be achieved, e.g., by epidermal patches, continuous release formulations, or on-body injectors.

The compound can be administered as a single bolus or multiple boluses, as a continuous infusion, or a combination thereof. For example, the compound can be administered as a single bolus initially, and then administered as a continuous infusion following the bolus. The rate of the infusion can be any desired rate. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another embodiment of any of the aspects, more than one-unit dosage form can be administered simultaneously.

The dosage of the therapeutic as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Efficacy

The efficacy of a therapeutic described herein, e.g., for the treatment of a viral infection, can be determined by the skilled practitioner. However, a treatment is considered "effective treatment," as the term is used herein, if one or more of the signs or symptoms of viral infection (e.g., HIV infection) are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., immune function. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of a viral infection, e.g., an HIV infection, as the case may be. When using an experimental animal model, efficacy of treatment is evidenced when a statistically significant change in a marker is observed, e.g., reduced viral infection.

Anti-Viral Therapies

In some embodiments, the agent or compositions described herein are used as a monotherapy. In another embodiment, the therapeutics described herein can be used in combination with other known agents and therapies for HIV infection. Administered "in combination," as used herein, means that two (or more) different treatments are delivered to the subject during the course of the subject's affliction with the disorder, e.g., the two or more treatments are delivered after the subject has been diagnosed with the disorder (e.g. HIV infection) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery."

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The compounds and agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

Therapeutics currently used to treat or prevent viral infections include but are not limited to: Acyclovir, Adefovir, Amantadine, Cidofovir, Combivir, Dolutegravir, Delavirdine, Didanosine, Emtricitabine, Entecavir, Famicolovir, Fosamprenavir, Imunovir, Indinavir, Inosine, Lopinavir, Lovaride, Maravirox, Nevirapine, Nucleoside analogues, Oseltamivir, Penciclovir, Rimantidine, Pyrimidine, Saquinavir, Stavudine, Tenofovir, Trizivir, Tromantadine, Truvada, Valaciclovir, Ciramidine, Zanamivir, Zidovudine, and any other antiviral drug known in the art.

Non-limiting examples of therapeutics that treat HIV infections are listed in Table 1 below.

TABLE 1

HIV anti-viral therapies.

| Class | Non-limiting examples of HIV antiviral therapeutics |
|---|---|
| Entry inhibitors/fusion inhibitors | Maravirox |
| | Enfuvirtide |
| | Sifuvirtide |
| | Albuvirtide |
| Nucleoside/nucleotide reverse-transcriptase inhibitors (NRTI) | Zidovudine (AZT, ZDV, and azidothymidine) |
| | Didanosine (ddI) |
| | Zalcitabine (ddC and dideoxycytidine) |
| | Stavudine (d4T) |
| | Abacavir |
| | Emtricitabine |
| | Emtriva (formerly Coviracil) |

TABLE 1-continued

HIV anti-viral therapies.

| Class | Non-limiting examples of HIV antiviral therapeutics |
|---|---|
| | Entecavir |
| | Truvada (emtricitabine and tenofovir disoproxil fumarate) |
| | Tenofovir |
| | Tenofovir alafenamide |
| | Tenofovir disoproxil |
| | Lamivudine |
| | Adefovir |
| Non-nucleoside reverse-transcriptase inhibitors (NNRTI) | Efavirenz |
| | Nevirapine |
| | Delavirdine |
| | Doravirine |
| | Etravirine |
| | Rilpivirine |
| Integrase inhibitors | Dolutegavir |
| | Elvitegravir |
| | Raltegravir |
| | Bictegravir |
| | BI 224436 |
| | Cabotegravir |
| | MK-2048 |
| Protease inhibitors | Amprenavir |
| | Atazanavir |
| | Darunavir |
| | Fosamprenavir |
| | Indinavir |
| | Lopinavir |
| | Nelfinavir |
| | Ritonavir |
| | Saquinavir |
| | Tipranavir |
| Cytochrome P450 inhibitor (to inhibit liver enzymes that metabolize antiretrovirals) | Cobicistat |

When administered in combination, the agent or compound described herein and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of diabetes) is lower (e.g., at least 20%, at least 30%, at least 40%, or at least 50% lower) than the amount or dosage of each agent individually required to achieve the same therapeutic effect.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the various aspects described herein can be described as in the following numbered paragraphs:

1. A compound of Formula (I):

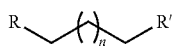

FORMULA (I)

and pharmaceutically acceptable salts thereof,
wherein:
n is an integer from 3 to 14;
R and R' are independently selected from the group consisting of:
(i) Formula (II):

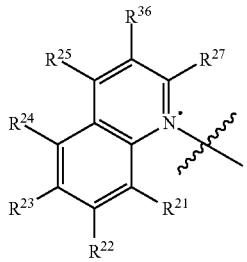

FORMULA (II)

wherein:
$R^{11}$, $R^{12}$, $R^{13}$, $R^{14}$ and $R^{15}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and $R^{16}$ and $R^{17'}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{26}$ and $R^{27}$, together with the carbon atoms they are attached to, form a 5-8 membered cyclyl, heterocyclyl, aryl or heteryaryl, each of which can be optionally substituted with 1, 2, 3, or more independently selected substituents;
(ii) Formula (III):

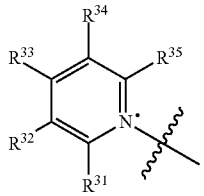

FORMULA (III)

wherein:
$R^{31}$, $R^{32}$ and $R^{33}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl; and $R^{34}$ and $R^{135}$ are independently selected from the group consisting of H, alkyl, haloalkyl, alkenyl, alkynyl, hydroxyl, alkoxy, amino, alkylamino, dialkylamino, carboxyl, acyl, halogen, nitro, cyano thiol, thioalkoxy, thiocarbonyl, sulfinyl, sulfonyl, thiocarbonyl, cyclyl, heterocylcyl, aryl and heteroaryl, or $R^{34}$ and $R^{35}$, together with the carbon atoms they are attached to, form a 5-8 membered cyclyl, heterocyclyl, aryl or heteryaryl, each of which can be optionally substituted with 1, 2, 3, or more independently selected substituents;
and pharmaceutically acceptable salts thereof; and
(iii) Formula (IV):

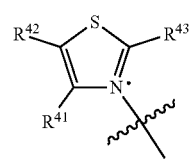

FORMULA (IV)

wherein:
$R^{41}$, $R^{42}$, and $R^{43}$ are independently selected from the group consisting of H, alkyl, haloalkyl, alkenyl, alkynyl, hydroxyl, alkoxy, amino, alkylamino, dialkylamino, carbonyl, carboxy, halogen, nitro, azido, cyano thiol, thioalkoxy, thiocarbonyl, sulfinyl, sulfonyl, thiocarbonyl, cyclyl, heterocylcyl, aryl and heteroaryl, and
provided that compound is not dequalinium.

2. The compound of paragraph 1, wherein n is 6, 8 or 10.
3. The compound of paragraph 1, wherein R and R' are independently of Formula (III).
4. The compound of paragraph 1, wherein R and R' are the same.
5. The compound of paragraph 1, wherein $R^{21}$, $R^{22}$, $R^{23}$, $R^{24}$, and $R^{25}$ are independently selected form the group consisting of H, alkyl, haloalkyl, hydroxyl, alkoxy, amino, alkylamino, dialkylamino, carboxyl, halogen, nitro, cyano, thiol, and thiolalkoxy; and $R^{26}$ and $R^{27}$ are independently selected form the group consisting of H, alkyl, haloalkyl, hydroxyl, alkoxy, amino, alkylamino, dialkylamino, carboxyl, halogen, nitro, cyano, thiol, and thiolalkoxy, or $R^{26}$ and $R^{27}$, together with the carbon atoms they are attached to, form a 4-8 membered cyclyl.
6. The compound of paragraph 5, wherein $R^{21}$, $R^{22}$, $R^{23}$, $R^{24}$, and $R^{25}$ are independently selected form the group consisting of H, halogen, $C_1$-$C_6$alkyl, halo($C_1$-$C_6$)alkyl, amino, $C_1$-$C_6$alkylamino, or di($C_1$-C-$_6$alkyl)amino; and $R^{26}$ and $R^{27}$ are independently selected form the group consisting of H, halogen, C1-$C_6$alkyl, halo($C_1$-$C_6$)alkyl, amino, $C_1$-$C_6$alkylamino, or di($C_1$-$C_6$alkyl)amino, or $R^{26}$ and $R^{27}$, together with the carbon atoms they are attached to, form a 5-membered cyclyl.
7. The compound of paragraph 6, wherein $R^{21}$, $R^{22}$, $R^{23}$ and $R^{24}$ are independently selected form the group consisting of H and halogen; $R^{25}$ is selected from the group consisting of H and amino; and $R^{26}$ and $R^{27}$ are independently selected form the group consisting of H and halogen, or $R^{26}$ and $R^{27}$, together with the carbon atoms they are attached to, form a 5-membered cyclyl.
8. The compound of paragraph 1, wherein the compound is selected from the group consisting of:
(i) R and R' are the same; $R^{21}$, $R^{22}$, $R^{23}$, and $R^{24}$ are H; $R^{25}$ is amino; $R^{26}$ and $R^{27}$, together with the carbon atoms they are attached to form a 5-membered cyclyl; and n is 4, 6, 8, 10;

(ii) R and R' are the same; $R^{21}$, $R^{22}$, $R^{23}$, $R^{24}$ and $R^{26}$ are H; $R^{25}$ is amino; $R^{27}$ is methyl; and n is 4, 6, 8, 10 or 12;

(iii) R and R' are the same; $R^{21}$, $R^{22}$, $R^{23}$, $R^{24}$, $R^{26}$ and $R^{27}$ are H; $R^{25}$ is amino; and n is 4, 6, 8, 10;

(iv) R and R' are the same; $R^{21}$, $R^{23}$, $R^{24}$, $R^{26}$ and $R^{27}$ are H; $R^{22}$ is halogen, e.g., Cl; $R^{25}$ is amino; and n is 4, 6, 8, 10;

(v) R and R' are the same; $R^{21}$, $R^{22}$, $R^{24}$, $R^{26}$ and $R^{27}$ are H; $R^{23}$ is halogen, e.g., Br; $R^{25}$ is amino; and n is 4, 6, 8, 10;

(vi) R and R' are the same; $R^{21}$, $R^{22}$, $R^{23}$, $R^{24}$, and $R^{27}$ are H; $R^{26}$ is halogen, e.g., Br; $R^{25}$ is amino; and n is 4, 6, 8, 10; and (vii) R and R' are the same; $R^{21}$, $R^{22}$, $R^{23}$, $R^{24}$, $R^{25}$, $R^{26}$ and $R^{27}$ are H; and n is 4, 6, 8, 10.

9. The compound of paragraph 1, wherein the compound is selected from the group consisting of:

(i) Compound S2C3, where R and R' are the same; $R^{21}$, $R^{22}$, $R^{23}$, and $R^{24}$ are H; $R^{25}$ is amino; $R^{26}$ and $R^{27}$, together with the carbon atoms they are attached to form a 5-membered cyclyl; and n is 8;

(ii) Compound S1C1, where R and R' are the same; $R^{21}$, $R^{22}$, $R^{23}$, $R^{24}$ and $R^{26}$ are H; $R^{25}$ is amino; $R^{27}$ is methyl; and n is 4;

(iii) Compound S1C4, where R and R' are the same; $R^{21}$, $R^{22}$, $R^{23}$, $R^{24}$ and $R^{26}$ are H; $R^{25}$ is amino; $R^{27}$ is methyl; and n is 10;

(iv) Compound S1C5, where R and R' are the same; $R^{21}$, $R^{22}$, $R^{23}$, $R^{24}$ and $R^{26}$ are H; $R^{25}$ is amino; $R^{27}$ is methyl; and n is 12;

(v) Compound S2C1, where R and R' are the same; $R^{21}$, $R^{22}$, $R^{23}$, $R^{24}$, $R^{26}$ and $R^{27}$ are H; $R^{25}$ is amino; and n is 8;

(vi) Compound S2C6, where R and R' are the same; $R^{21}$, $R^{23}$, $R^{24}$, $R^{26}$ and $R^{27}$ are H; $R^{22}$ is Cl; $R^{25}$ is amino; and n is 8;

(vii) Compound S2C7, where R and R' are the same; $R^{21}$, $R^{22}$, $R^{24}$, $R^{26}$ and $R^{27}$ are H; $R^{23}$ is Br; $R^{25}$ is amino; and n is 8;

(viii) Compound S2C8, where R and R' are the same; $R^{21}$, $R^{22}$, $R^{23}$, $R^{24}$ and $R^{27}$ are H; $R^{26}$ is Br; $R^{25}$ is amino; and n is 8;

(ix) Compound S2C10, where R and R' are the same; $R^{21}$, $R^{22}$, $R^{23}$, $R^{24}$, $R^{25}$, $R^{26}$ and $R^{27}$ are H; and n is 8;

(x) Compound S1C2, where R and R' are the same; $R^{21}$, $R^{22}$, $R^{23}$, $R^{24}$ and $R^{26}$ are H; $R^{25}$ is amino; $R^{27}$ is methyl; and n is 6;

(xi) Compound S2C9, where R and R' are the same; $R^{31}$, $R^{32}$ and $R^{34}$ are H; $R^{33}$ is $NH_2$; and $R^{35}$ is methyl; and (xii) Compound S2C11, where R and R' are the same; $R^{41}$ is methyl; $R^{42}$ is ethyl; and $R^{43}$ is H.

10. A composition comprising the compound of any one of paragraphs 1-9.

11. The composition of paragraph 10, further comprising a pharmaceutically acceptable carrier.

12. A pharmaceutical composition comprising a compound of any one of paragraphs 1-9.

13. A method of treating or preventing a viral infection, the method comprising: administering to a subject in need thereof a compound of any of paragraphs 1-9, a composition of paragraphs 10 and 11, or a pharmaceutical composition of paragraph 12.

14. The method of paragraph 13, wherein the subject is a human.

15. The method of paragraph 13, wherein the viral infection results in acquired immune deficiency syndrome (AIDS).

16. The method of paragraph 13, wherein the viral infection is a human immunodeficiency virus-1 (HIV-1) infection or an HIV-2 infection.

17. The method of paragraph 16, wherein the HIV-1 or HIV-2 infection is resistant to at least one HIV treatment.

18. The method of paragraph 17, wherein the HIV-1 infection is resistant to an inhibitor of HIV-1 fusion to a target cell.

19. The method of paragraph 18, wherein the inhibitor of HIV-1 fusion is Maravirox, Enfuvirtide, Sifuvirtide, or Albuvirtide.

20. The method of paragraph 18, wherein the target cell is a mammalian cell.

21. The method of paragraph 18, wherein the target cell is a human cell.

22. The method of any one of paragraphs 18-21, wherein the target cell is a leukocyte, a lymphocyte, a T cell, or a CD4+ T cell.

23. A method of treating or preventing a viral infection, the method comprising: administering to a subject in need thereof an agent that inhibits the membrane proximal external region (MPER) of a viral envelope (Env).

24. The method of paragraph 23, wherein the subject is a human.

25. The method of paragraph 23, wherein the viral infection results in acquired immune deficiency syndrome (AIDS).

26. The method of paragraph 23, wherein the viral infection is a human immunodeficiency virus-1 (HIV-1) infection or an HIV-2 infection.

27. The method of paragraph 23, wherein the viral envelope is the HIV-1 or HIV-2 Env.

28. The method of paragraph 26, wherein the HIV-1 or HIV-2 infection is resistant to at least one HIV treatment.

29. The method of paragraph 27, wherein the HIV-1 infection is resistant to an inhibitor of HIV-1 fusion to a target cell.

30. The method of paragraph 29, wherein the inhibitor of HIV-1 fusion is Maravirox, Enfuvirtide, Sifuvirtide, or Albuvirtide.

31. The method of paragraph 29, wherein the target cell is a mammalian cell.

32. The method of paragraph 29, wherein the target cell is a human cell.

33. The method of any one of paragraphs 29-32, wherein the target cell is a leukocyte, a lymphocyte, a T cell, or a CD4+ T cell.

34. The method of paragraph 23, wherein the agent is a compound of any one of paragraphs 1-9.

35. The method of paragraph 23, wherein the agent is the composition of paragraphs 10 and 11, or the pharmaceutical composition of paragraph 12.

36. The method of any one of paragraphs 23-33, wherein the agent that inhibits the viral Env is selected from the group consisting of: a small molecule, an antibody reagent, a peptide, a genome editing system, an antisense oligonucleotide, and an RNAi.

37. The method of paragraph 36, wherein the small molecule is dequalinium.

38. The method of paragraph 36, wherein the small molecule is a derivative of dequalinium selected from a group consisting of: Analog 1, Analog 2, Analog 3, Analog 4, 4-aminoquinaldine, C800, S1C1, S1C2, S1C4, S1C5, S2C1, S2C3, S2C6, S2C8, S2C9, S2C10, and S2C11.

39. The method of paragraph 38, wherein, the small molecule is a derivative of S2C3.

40. The method of paragraph 38, wherein the small molecule is a derivative of C800.

41. The method of paragraph 36, wherein the RNAi is a microRNA, an siRNA, or a shRNA.
42. The method of paragraph 23, wherein inhibiting MPER results in the inhibition of Env fusion to the target cell.
43. The method of paragraph 42, wherein the fusion to the target cell is inhibited by at least 50%, at least 60%, at least 70%, at least 80%, at least 90%, or more as compared to an appropriate control.
44. A method of treating or preventing a human immunodeficiency virus (HIV) infection, the method comprising: administering to a subject in need thereof a compound of any of paragraphs 1-9, a composition of paragraphs 10 and 11, a pharmaceutical composition of paragraph 12, or an agent that inhibits the membrane proximal external region (MPER) of a viral envelope (Env).
45. A method of inhibiting Env fusion to a target cell, the method comprising: administering to a target cell a compound of any of paragraphs 1-9, a composition of paragraphs 10 and 11, a pharmaceutical composition of paragraph 12, or an agent that inhibits the membrane proximal external region (MPER) of a viral envelope (Env).
46. The method of paragraph 45, wherein the target cell is a mammalian cell.
47. The method of paragraph 45, wherein the target cell is a human cell.
48. The method of any one of paragraphs 45-47, wherein the target cell is a leukocyte, a lymphocyte, a T cell, or a CD4+ T cell.
49. The method of paragraph 45, wherein the viral envelope is the HIV-1 or HIV-2 Env.
50. The method of any one of paragraphs 45-49, wherein the agent is the compound of any one of paragraphs 1-9.
51. The method of any one of paragraphs 45-49, wherein the agent is the composition of any one of paragraphs 10-11, or the pharmaceutical composition of paragraph 12.
52. The method of any one of paragraphs 45-49, wherein the agent that inhibits the viral Env is selected from the group consisting of: a small molecule, an antibody reagent, a peptide, a genome editing system, an antisense oligonucleotide, and an RNAi.
53. The method of paragraph 52, wherein the small molecule is dequalinium.
54. The method of paragraph 52, wherein the RNAi is a microRNA, an siRNA, or a shRNA.
55. The method of any one of paragraphs 45-54, wherein the Env fusion to the target cell is inhibited by at least 50%, at least 60%, at least 70%, at least 80%, at least 90%, or more as compared to an appropriate control.
56. A method of treating a viral infection, the method comprising:
    a. diagnosing a subject as having a viral infection; and
    b. administering to the subject having a viral infection a compound of any of paragraphs 1-9, a composition of paragraphs 10 and 11, a pharmaceutical composition of paragraph 12, or an agent that inhibits the membrane proximal external region (MPER) of a viral envelope (Env).
57. A method of treating a viral infection, the method comprising:
    a. receiving the results of an assay that diagnoses a subject as having a viral infection; and
    b. administering to the subject having a viral infection a compound of any of paragraphs 1-9, a composition of paragraphs 10 and 11, a pharmaceutical composition of paragraph 12, or an agent that inhibits the membrane proximal external region (MPER) of a viral envelope (Env).
58. A method of preventing a viral infection, the method comprising:
    a. diagnosing a subject as being at risk for having a viral infection; and
    b. administering to the subject at risk of having a viral infection a compound of any of paragraphs 1-9, a composition of paragraphs 10 and 11, a pharmaceutical composition of paragraph 12, or an agent that inhibits the membrane proximal external region (MPER) of a viral envelope (Env).
59. A method of treating a viral infection, the method comprising:
    a. receiving the results of an assay that diagnoses a subject as being at risk for having a viral infection; and
    b. administering to the subject diagnosed as being at risk of having a viral infection a compound of any of paragraphs 1-9, a composition of paragraphs 10 and 11, a pharmaceutical composition of paragraph 12, or an agent that inhibits the membrane proximal external region (MPER) of a viral envelope (Env).
60. The method of any of paragraphs 56-59, wherein the viral infection is a human immunodeficiency virus (HIV) infection.
61. A composition comprising any of the agents of paragraphs 23-43.
62. A method for identifying a test agent that modulates the activity of MPER of a viral envelope (Env), the method comprising:
    a. contacting a glycoprotein 41 (gp41) or fragment thereof with a test agent;
    b. contacting the gp41 or fragment thereof with an antibody or fragment thereof that specifically binds to the MPER; and
    c. detecting a contact level between the antibody and the MPER; wherein a change in the contact level relative to a control or reference level indicates that the agent modulates the MPER.
63. The method of paragraph 62, wherein the antibody is 2F5 Fab.
64. The method of paragraph 62, wherein the detecting comprises analyzing the gp41 contacted in steps (a) and (b) using a fluorescent polarization assay, and wherein a change in the fluorescent polarization signal relative to a control or reference level indicates that the agent modulates the activity of MPER.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Targeting the MPER

HIV Infection

The HIV virus is an RNA virus and it has the enzyme reverse transcriptase which enables it to make a DNA copy of the viral RNA. The virus has an outer envelope and a dense cylindrical core containing RNA genome. The envelope consists of a lipid membrane with protruding spikes which are coated with glycoproteins. The glycoproteins contain different sugar molecules, some of which appear to be constant, but some may be variable. It is the variability of these sugar molecules that eludes the body's immune system in detecting the virus particles. Genes that code for structural components of HIV include the gag gene which codes for core, the env gene which codes for envelope proteins, and the pol gene which encodes viral reverse transcriptase. The gag, pol, and env genes are common to all retroviruses. The diameter of the virus is 100-120 um and it is produced in high numbers from infected cells by budding from the cell membrane in culture.

The virus exists in the blood circulation of the patient in two forms: as cell-free virus or mature virion having a lipid envelope, and as cell-associated virus or replicating virus in the infected cells (T-4 lymphocytes, monocyte, macrophages). The virus is essentially an intracellular parasite and in order to survive and perpetuate itself it has to penetrate and infect the host cells. The lipid envelope with its glycoprotein spikes provide the means for penetrating and infecting the white cells. The virus will replicate inside the infected cells and will produce mature virions with lipid envelope and glycoprotein spikes, budding from the membrane of the infected cell. These mature virions in turn will penetrate and infect the new and healthy cells as they are released from the hematopoietic system, and the vicious cycle will go on.

The first step of HIV-1 infection is fusion of viral and target cell membranes mediated by Env. The mature Env spikes [trimeric (gp160), cleaved to (gp120/gp41)] are the sole antigens on the virion surface. Conformational changes in gp120 when triggered by binding to receptor (CD4) and co-receptor (e.g., $CCR^5$ or CXCR4) lead to a cascade of refolding events in gp41, in which its N-terminal fusion peptide translocates and inserts into the host cell membrane. A transient, extended conformation of gp41, with the fusion peptide in the host cell membrane and the transmembrane anchor still in the viral membrane, has been called the "prehairpin intermediate." This conformational state of gp41 exposes highly conserved regions, including the binding site of Enfuvirtide, and the epitopes of several broadly neutralizing antibodies (bnAbs), including 2F5, 4E10 and 10E8, in the MPER. The MPER is an attractive target for fusion inhibitors because it is one of the most conserved and functionally critical regions of the entire HIV-1 Env. Specifically, the MPER is required for viral infectivity. Antibodies such as 2F5, 4E10, Z13e1 and 10E8 can block HIV-1 infection by a common mechanism that involves binding the prehairpin intermediate state of gp41 with the help of their lipid binding activity. NMR studies suggest that the MPER is well-structured and indeed contains a small-molecule binding site as described herein.

Combination antiretroviral therapy (cART) has transformed HIV-1 infection, once a fatal illness, to a manageable chronic condition[1-3]. The latest cART regimen uses several classes of antiviral therapeutics and a typical therapy requires a combination of three or more drugs from at least two classes. Drug resistance, severe side effects and difficulties in treatment compliance have brought challenges to the implementation of the cART in clinical settings and indicate the need for additional molecular targets. Enfuvirtide, a 36-residue peptide derived from HIV-1 gp41, is the first and still the only fusion inhibitor approved by FDA[4,5]. It is now rarely used by HIV-1 infected patients, however, because of its numerous disadvantages[6-8].

The MPER of HIV-1 Env can be a target for developing small-molecule inhibitors of viral membrane fusion. In particular, recent studies indicate that the MPER adopts a well-defined structure that is not buried in membrane and indeed contains a small-molecule binding pocket. Moreover, several MPER-directed hit compounds are described herein, that can specifically inhibit membrane fusion mediated by HIV-1 Env, but not SIV Env. The ultimate goal of high-throughput screening described herein was to discover lead therapeutic candidates for preclinical testing and to provide novel reagents that prevent HIV-1 entry. In a high throughput screen (HTS) designed to search for small-molecule fusion inhibitors that mimic the bnAb 2F5, two hit compounds that can specifically inhibit membrane fusion mediated by HIV-1 Env, but not by SIV Env have been tested. These data indicate the therapeutic potential of the MPER. The repertoire of the MPER-directed compounds can be expanded by screening additional libraries and by similar HTS assays using other bnAbs, such as, 4E10 and their mutants.

A completed NMR structure of a gp41 construct containing the transmembrane domain (TMD) and the MPER in the context of lipid bilayer has been identified. In this structure, the MPER forms a well-structured trimer that is not buried in membrane.

HIV Fusion Inhibitors

HIV-1 Env mediates fusion of viral and target cell membranes to initiate infection. The protein is synthesized as a precursor, gp160, which trimerizes and undergoes cleavage into two non-covalently associated fragments: the receptor-binding fragment gp120 and the fusion fragment gp41 (FIG. 1A). Three copies of each fragment constitute the mature viral spike (gp120/gp41). Sequential binding of gp120 to receptor CD4 and coreceptor CXCR4 or CCR5 induces possible dissociation of gp120 and a cascade of refolding events in gp41 (FIG. 1B)[19,20]. Gp41, with its C-terminal transmembrane segment inserted in the viral membrane, folds into a pre-fusion conformation within the precursor gp160. Cleavage between gp120 and gp41 makes the protein metastable with respect to a rearranged, post-fusion conformation. When triggered, the N-terminal fusion peptide of gp41 translocates and inserts into the target cell membrane. The extended conformation of gp41, with the fusion peptide inserted into the target cell membrane and the transmembrane anchor in the viral membrane, is referred to as the prehairpin intermediate[10]. This state is targeted by Enfuvirtide4, as well as by certain broadly neutralizing antibodies (bnAbs), including 2F5, 4E10 and 10E8. Subsequent rearrangements involve folding back of the C-terminal region (heptad repeat 2) of gp41 into a hairpin conformation, thereby creating a six-helix bundle known as the post-fusion conformation, which brings the two membranes together, ultimately leading to HIV-1 entry.

Gp41 is the core machinery for HIV-1 entry and contains the most conserved regions within the entire Env, which are critical for membrane fusion. The fusion-promoting conformational changes expose some of these regions, exemplified by the Enfuvirtide binding site, and provide attractive targets for developing broad fusion inhibitors. Although Env has greater diversity than HIV-1 reverse transcriptase or protease, fusion inhibitors do not need to cross cell membrane to reach their target. In addition, unlike those enzymes, gp41 has no obvious cellular homologs; it is therefore a more likely target for inhibitors with high specificity but minimal side effects.

Targeting the MPER

Figures 7A, 7B:
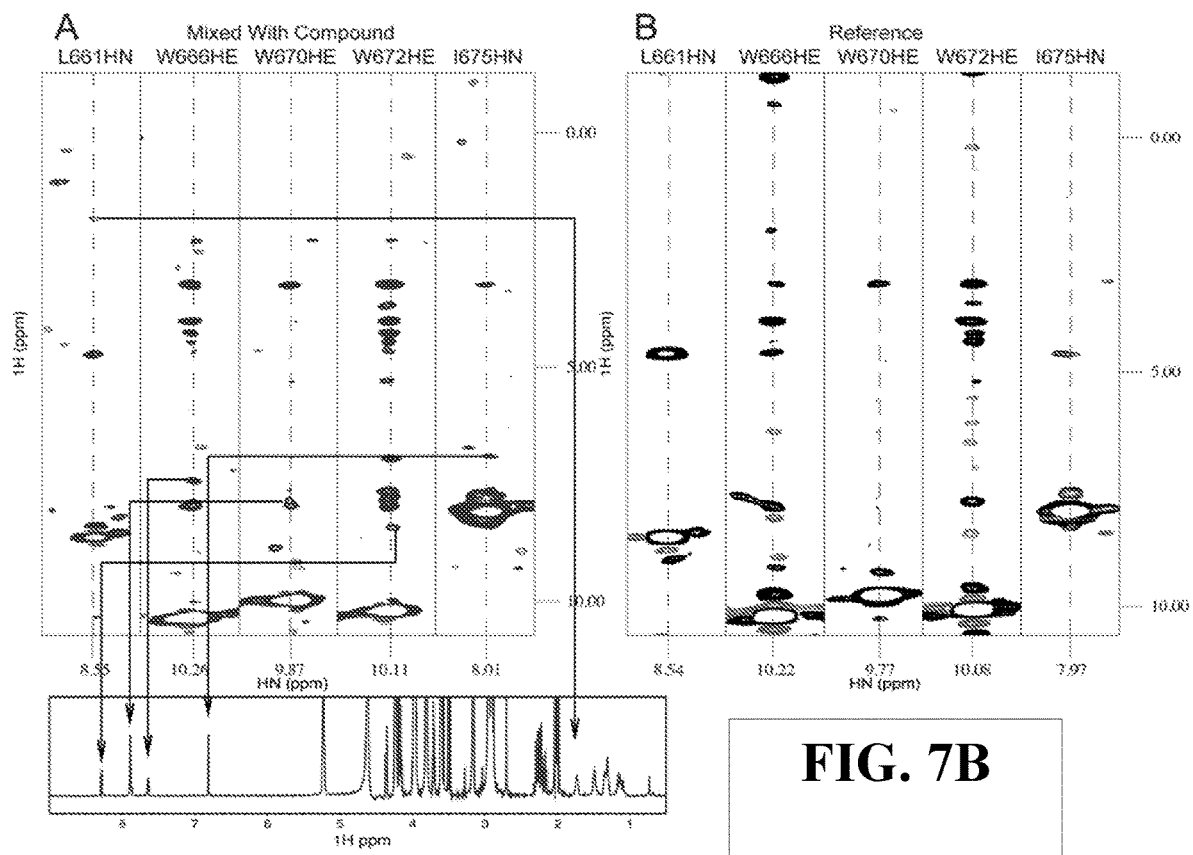
Figure 7C:
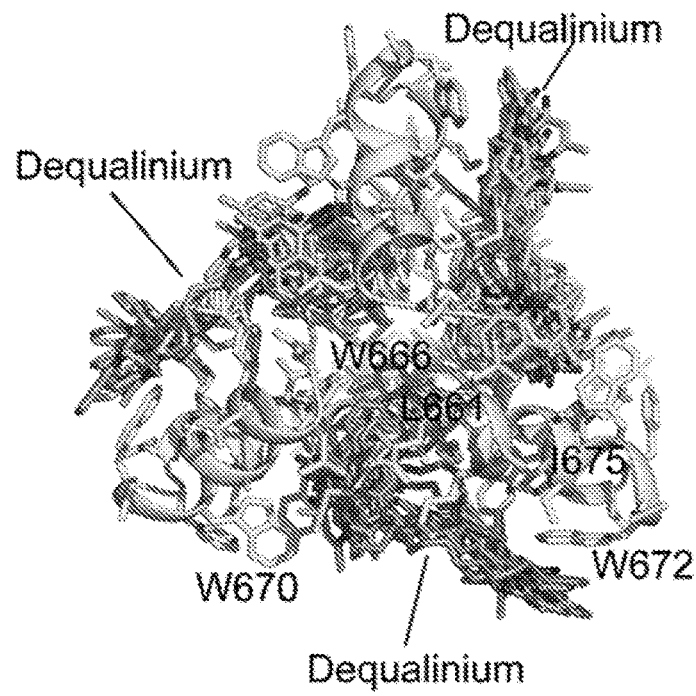
Figure 7D:
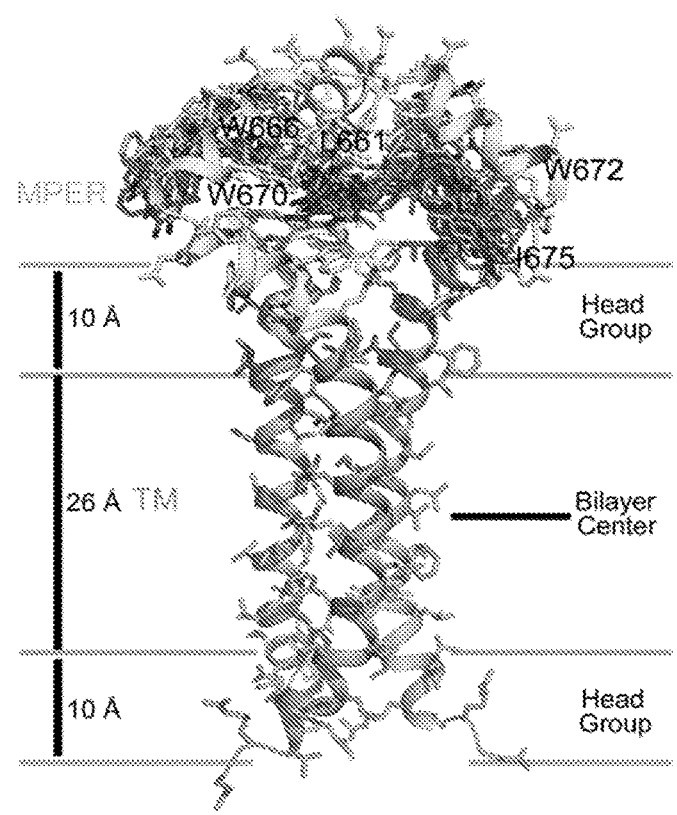

The MPER, a hydrophobic region of about 25 residues, adjacent to the viral membrane, is one of the most conserved regions in gp41, but it has yet to be explored as a therapeutic target. The MPER is required for viral infectivity. Its role in the mechanism of viral fusion is still unknown. Despite their remarkable neutralization potencies against a wide spectrum of HIV-1 isolates in vitro, studies involving passive transfer of 2F5 and 4E10 in HIV-1 infected patients suggest that the antibodies may not be effective in blocking HIV-1 propagation in vivo. The latest NMR studies described herein show that the MPER is well-structured and indeed contains a small-molecule binding site (FIG. 7A-7C). Several small-molecule compounds have been identified that bind the MPER and specifically block HIV-1 Env-mediated membrane fusion. These results suggest that small-molecule fusion inhibitors may be developed to prevent HIV-1 infection by targeting the MPER. The search for next-generation fusion inhibitors against HIV-1 has been an active area of research. New strategies and novel targets will allow the development of effective therapeutics that can improve cART. The latest advances in the HIV-1 vaccine field have been employed to rationally design Env constructs, together with anti-HIV-1 antibodies to enable the discovery of fusion inhibitors.

Provided herein is a new strategy to identify small-molecule inhibitors guided by neutralizing antibodies. Use of well-characterized neutralizing antibodies to guide drug discovery is also innovative. Small-molecule fusion inhibitors can be developed that target functionally critical sites (neutralizing epitopes) pre-selected by the human immune system. MPER was chosen as a test case, which contains neutralizing epitopes of 2F5, 4E10 and 10E8. The concept of using known neutralizing antibodies to direct drug development was applied to other epitopes on HIV-1 Env, and can be applied to other infectious agents.

Described herein is the development of therapeutic candidates of HIV-1 targeting the membrane proximal external region of gp41- the core machinery for viral entry. To not be bound by a particular theory, it is hypothesized that the MPER of HIV-1 Env is a target for developing small-molecule fusion inhibitors of viral membrane fusion. To test this hypothesis, a number of methods are described herein.

Identification of Small-Molecule Fusion Inhibitors Targeting the MPER of HIV-1 Env The prehairpin conformation of gp41 is a transient, fusion-intermediate state. To capture this conformation, a construct was designed, designated gp41-inter, with the following sequence: (HR2)-linker-[NR1-CCloop-HR2-MPER]-(trimerization foldon tag) (FIG. 2A-2B). The linker is a short, flexible connector of serines and glycines. When gp41-inter chains trimerize, the N-terminal HR2 segments form a six-helix bundle with the HR1 segments, because the C-terminal HR2 segments, constrained by the foldon tag, will be unable to form a six-helix bundle. This construct thus can be pictured as the prehairpin intermediate captured by a covalently-linker HR2 peptide, such as Enfuvirtide. Purified gp41-inter is a stable and soluble trimer in solution. Extensive biochemical and antigenicity studies of gp41-inter confirms that it indeed represents the prehairpin intermediate conformation of gp41. It was observed that 2F5, 4E10 and 10E8 block HIV-1 entry by a common mechanism—targeting the gp41 fusion intermediate. To screen small-molecule compounds that bind the MPER and may mimic the neutralizing antibodies to abort membrane fusion, a sensitive, fluorescence polarization (FP) assay has been developed to detect binding of 2F5 or 4E10 to gp41-inter (FIG. 3A). Any compound that binds the antibody epitope with high enough affinity can disrupt this interaction and compete for binding to gp41-inter. FITC (Fluorescein isothiocyanate)-labeled 2F5 or 4E10 Fab binds with high affinity to gp41-inter as measured by fluorescence polarization (FIG. 3B and 3C). Unlabeled antibody effectively competes with the labeled Fab to diminish the fluorescence signal. The Z' factor is 0.52 for the 2F5 assay and 0.65 for the 4E10 assay, when the unlabeled Fab was used as a positive control and DMSO as a negative control, suggesting they are suitable for high throughput screening (HTS). It has been established that a secondary assay by substituting gp41-inter with a short corresponding epitope peptide of gp41 in the primary assay to distinguish compounds that bind 2F5 from those that bind gp41-inter. The epitope peptide is flexible and has no defined structure in solution; compounds that specifically interact with the gp41-inter trimer cannot bind the unstructured, monomeric peptide to block the peptide-antibody interaction, but those that bind the antibody can interfere with its binding to both the peptide and gp41-inter. In this case, the labeled peptide and unlabeled antibody was used, which yielded the best signals for fluorescence polarization.

An initial screen was completed with 144,844 compounds from libraries found on the Harvard Institute for Chemistry and Chemical Biology (ICCB) website available on the world-wide web at http <iccb.med.harvard.edu/>. All screening was performed in duplicate, using the labeled 2F5 Fab. Any compounds that fluoresce or scatter light were eliminated, thus interfering with the FP assay. Duplicate values were averaged and selected those with a Z score of 5 or greater. The 75 compounds meeting these criteria were considered "hits", giving a hit rate of 0.05%. Hits were further screened by surface plasmon resonance (SPR) for binding to gp41-inter but not to 2F5, and for their ability to inhibit cell-cell fusion mediated by HIV-1 Env but not by SIV Env. The two best compounds were chosen for further analysis. To analyze HIV-1 fusion inhibitors, a cell-cell fusion assay has been adapted based on the α-complementation of *E. coli*β-galactosidase. As depicted in FIG. 4, the function of an inactive mutant β-galactosidase with N-terminal residues 11-41 deleted (co fragment) is rescued by its N-terminal fragment (a fragment; residues 3-90), upon Env-mediated cell-cell fusion. This α-complementation-based method is simple, robust and independent of new transcription, protein synthesis and trafficking in the fused cells, requiring only 2 hr incubation time. The assay is extremely sensitive with an excellent signal-to-noise ratio.

One hit compound, dequalinium (quinolinium,1,1'-(1,10-decanediyl)-bis(4-amino-2-methyl diiodide); FIG. 5D), is an FDA-approved, antimicrobial drug. It effectively inhibits cell-cell fusion mediated by HIV-1 Env with an $IC_{50}$ of 13.8 μM, but not by SIV Env (FIG. 5A). It showed a minimal level of cytotoxicity up to 50 μM by an assay measuring ATP concentration, which correlates with the amount of metabolically active cells. Dequalinium can also target Envs from multiple primary HIV-1 isolates of different clades (FIG. 5B), suggesting that it recognizes a conserved binding site. It binds gp41-inter with an affinity of 11 μM and shows no binding to 2F5 (FIG. 5C). An Env mutant containing a mutation W666A in the 2F5 core epitope was significantly more resistant to inhibition of cell-cell fusion by dequalinium than the wildtype Env (not shown), supporting that the compound indeed targets the 2F5 epitope. Inhibition of 1-11V-1 infectivity was tested using a luciferase-based virus inhibition assay with Env pseudoviruses in TZM.b1 cells. In this assay, which requires incubation for 48 hrs to allow the luciferase reporter gene expression, dequalinium showed more cytotoxicity than in the cell-cell fusion assay. Nevertheless, it exhibited greater inhibition to several HIV-1 isolates than to the murine leukemia virus (MuLV) control (FIG. 5E).

Research Methods a. HTS. High throughput screening (HTS) assays are performed in 384 well microtiter plates (Nunc), and fluorescence polarization is measured on an EnVision multilabel reader (Perkin Elmer). Gp41-inter is added to each well at a final concentration of 50 nM in PBS, followed by transfer of 0.5 µl of compound (~150 µM). After incubation for 1 hr at room temperature, fluorescein-labeled 2F5 Fab is added to each well (final concentration 50 nM). After a 90-min incubation period, fluorescence polarization measurements are recorded. A 12 hr time point will also be recorded to ensure that equilibrium has been reached. The hit rate from the 2F5-based HTS is relatively low, probably due to the high affinity between 2F5 and gp41-inter[11], which can exclude weak competitors. Therefore, the screen can encompass all the libraries using the assay with the labeled 2F5 or 4E10 mutants showing weaker binding to gp41-inter than does the wildtype antibody, as previously reported. It will require ~8 mg of FITC-labeled Fab and ~3 mg of gp41-inter to screen 100,000 compounds, which are well within the production capacities. Stable 293T cell lines expressing 2F5 and 4E10 Fabs were generated.

b. Compound libraries. Compound libraries include known bioactives collections (total of 9,659 compounds) and a number of commercial libraries (total of 205,916 compounds): Biomoll, 4 and Biomol ICCBL (Enzo Life Sciences International, Inc.), Microsource 1, MS Discovery, NINDS Custom Collection (Discover Systems, Inc., Gaylordsville, Conn.), NIH clinical collection 1 and 2, Prestwick2 (Prestwick Chemical Inc), TocriScreen Mini Library (Tocris Bioscience), ActiMol TimTec 1 (Newark, Del.), Asinex 1 (Winston-Salem, N.C.), Bionet (Ryan Scientific, Mount Pleasant, S.C.), CEREP (Redmond, Wash.), ChemDiv (San Diego, Calif.), and ChemBridge (San Diego, Calif.), ENAMINE (Ukraine), Life Chemicals (Burlington, ON, Canada), Maybridge (Trevillet, Tintagel, Cornwall, U.K.). ICCB also has a collection of natural product extracts with a total of 70,423 wells. Most of these biological compounds are naturally produced to interact with proteins. If necessary, the Molecular Libraries Program (MLP) collection can be screened with additional 328,633 compounds assembled by the NIH Molecular Libraries Initiative. Compound libraries can be prioritized with the following order: 1) known bioactives; 2) natural product extracts; 3) academic collections; 4) most recently plated commercial compounds and 5) other commercial compounds available on the worldwide web at http <iccb.med.harvard.edu/libraries/compound-libraries/>.

c. "Secondary screen. Potential hits will be subjected to a secondary screen using the primary assay at different concentrations. All hits will be tested in the secondary screen for antibody binding as described herein. True hits can be positive in the primary screen, and negative in the secondary screen.

d. SPR binding. Direct binding of the selected compounds to gp41-inter by SPR were confirmed. Binding kinetics of interactions between gp41-inter and the selected compounds can be analyzed following protocols as described herein. Briefly, gp41-inter will be immobilized on a sensor chip; various concentrations of the compounds will flow over the gp41-inter surface; sensorgrams will be recorded using Biacore T200 (with sensitivity to detect small-molecule binding); and binding kinetics will be evaluated with BiaEvaluation® software (Biacore).

e. Cytotoxicity Assay. To measure cytotoxicity of the compounds, the compounds are incubated at different concentrations with untransfected cells using a the CellTiter-Glo 2.0 Assay (Promega), which measures changes in the amount of ATP due to cell death, according to the protocol recommended by manufacturer.

Hit validation by cell fusion and viral infectivity assay. Once additional hit compounds are identified, commercially available analogs and custom-synthesized analogs can also be screened. The effects on both cell-cell fusion and HIV-1 infectivity of the selected compounds can be identified by performing the cell fusion and viral infectivity assays. For the viral infectivity assays, inhibition of HIV-1 infectivity can be measured using luciferase-based virus inhibition assays with Env pseudoviruses in TZM.bl cells according to a protocol described previously. These assays measure the reduction in luciferase reporter gene expression in TZM.bl cells following a single round of virus infection. Three-fold serial dilutions of compounds by 10% DMEM growth medium will be performed in duplicate in a 96-well plate. Virus will be added to each well, and the plate will be incubated for 1 hour at 37° C. TZM.bl cells will then be added ($1\times10^4$/well) in 10% DMEM growth medium containing DEAE-Dextran (Sigma) at a final concentration of 11 µg/ml. Murine leukemia virus (MuLV) will be used as a negative control. HIV-1 Env pseudoviruses will be prepared as previously described.[38]

Viral inhibition by compounds can be confirmed using a peripheral blood mononuclear cell (PBMC)-based assay. Briefly, serial dilutions of compounds can be performed in 10% RPMI growth medium in a 96-well flat bottom plate. Infectious molecular clone (IMC) HIV-1 expressing Renilla luciferase[42] can be added, and the plate can be incubated for 1 hour at 37° C. PBMCs will be then added ($9\times10^4$/well) in 10% RPMI growth medium containing DEAE-Dextran (11 µg/ml). Assay controls include replicate wells of PBMCs alone (cell control), and PBMCs with virus (virus control). Following 5 day incubation at 37° C., cell suspension will be transferred to a 96-well white solid plate. Diluted ViviRen Renilla luciferase substrate (Promega) can be added to each well, and after 4 minutes the plates can be read on a Victor 3 luminometer. Clade C IMC Renilla luciferase viruses Du422.1.LucR.T2A.ecto, Ce2010 F5.LucR.T2A.ecto, and Ce1086_B2.LucR.T2A.ecto and stocks will be prepared in 293T/17 cells.

Based on the results, additional HTS, in particular, with the use of 2F5 or 4E10 mutants is specifically contemplated herein. FP assays can be set up with two other MPER-specific bnAbs, 10E8, Z13e1, and their mutants to identify other targets. Each of these antibodies recognizes a slightly different epitope within the MPER with different affinity. The screens with different antibodies will probably give different hits and thus complement each other.

A Structure-Based Platform for Lead Optimization

Structural biology has proven to be a highly effective tool throughout the early stages of drug discovery. High-resolution structures of the hit compounds can be determined in complex with gp41 constructs by NMR, x-ray crystallography or cryoEM. An NMR structure at atomic resolution has been constructed of a gp41 construct (MPER-TMD) containing the MPER and TMD, reconstituted in a membrane-like environment. A similar strategy has been used to determine the structure of dequalinium in complex with the MPER-TMD. This NMR system provides an unprecedented structure-based platform in the presence of membrane for us to understand molecular mechanisms of how these small-molecule compounds interact with the MPER and to guide effective SAR studies. X-ray crystallography and cryoEM can be employed as alternative approaches.

a. Structure determination of complexes of the MPER-TMD construct and hit compounds by NMR. Solution NMR is a proven approach to study protein-ligand interactions, even with weak ligands and membrane proteins. A general strategy for determining NMR structures of the complexes of the MPER-TMD protein and small-molecule inhibitors is described herein. To first identify the proximal compound binding site, a mixture of ($^{15}$N, $^2$H)-labeled MPER-TMD protein reconstituted in completely $^2$H-labeled bicelles with the compound to unambiguously assign NOEs between protein amide protons and compound protons can be completed. To further refine the binding site, NOEs can be identified between protein side chains and the compound. For this, selective side chain labeling and side chain NOE experiments can be tailored as needed depending on the initial binding site. If necessary, labeled compounds can be synthesized to obtain additional NOE restraints for high-precision structural information.

Additional data can be collected to finalize this structure. In the current NMR model, the conformation of dequalinium is not fully characterized due to the insufficient number of distance restraints. To further refine the structure, additional distance restraints can be obtained from NOESY spectra using selectively $^{15}$N-, $^2$H-labeled MPER-TMD with only the backbone amide groups and the side chain methyl groups of Ile, Leu and Val protonated. The MPER contains 5 Leu and 3 Ile and their protonated methyl groups will allow the ability to observe the NOE peaks between dequalinium and these side chains. The exact conformation of the compound can be well resolved when additional distance restraints to the calculation are added. In addition, this strategy can be applied to determine structures of other promising small-molecule compounds, such as the more potent analogs of dequalinium.

b. X-ray crystallography. The NMR system requires reconstitution of the MPER-TMD in detergent/lipid-mixed bicelles, which may pose technical challenges for other compounds more hydrophobic than dequalinium. As an alternative approach, crystallization of the complexes of gp41-inter and the hit compounds can be completed. A "Mosquito" crystallization robot (TTP LabTech) can be used to set up crystallization drops of 100 nl. For the hanging drop method, 100 nl of protein be added in each well of a 96-well crystallization tray with an equal volume of the crystallization solution. Initially, 960 crystallization conditions can be tested, using grid screens with different precipitants, and a few sparse-matrix screens from Hampton Research and Emerald Biostructures. A laboratory X-ray source can then be used to characterize the crystals. All full data sets will be collected at a synchrotron source. The 24-ID beamlines of NE-CAT at APS, are equipped with MD-2 Microdiffractometers and Pilatus detector for small crystals can also be used. HKL2000 or XDS will be used for data processing. For gp41-inter crystals, molecular replacement will provide initial phases. Phase improvement, model building and refinement will follow standard procedures. Phaser and other CCP4 programs will be used for MR and phase improvement. Program Coot will be used for model building. Refmac or Phenix were used for refinement.

c. CryoEM. Gp41-inter can form very stable complexes with Fabs derived from anti-gp41 cluster I or cluster II antibodies, which can significantly increase its size to the range suitable for cryoEM analysis. Images of protein molecules in random orientations can be recorded in their native conformation in vitreous ice by electron microscopy and provide enough information for reconstruction of a 3D image of the protein. Electron microscopes such as an FEI G2 Polara and an FEI F20, both equipped with K2 Summit direct electron detectors, an FEI T12 and a Philips CM10, can be used to identify interactions with MPER. For CCR5, large data sets have been collected using the Talos Arctica and the Titan Krios microscopes.

Briefly, cryo grids are prepared and can be used to optimize freezing conditions using the FEI Vitrobot. Cryo grids can be screened with the Talos Arctica microscope based on protein concentration, ice thickness and particle distribution. Large data sets can be collected using the Titan Krios microscope. Data collection will use SerialEM® software[68]. In a movie mode, entire exposures are recorded on multiple frames. These frames will be aligned and averaged to reduce the blurring effect introduced by drift of the stage or holder and by beam-induced ice movement using MotionCor2[69]. The contrast transfer function (CTF) can be estimated by CTFFIND4[70] using motion-corrected images. RELION®[71] can be used for particle selection, initial map generation, 2D classification, and 3D classification and refinement. The MPER has been reported to form helical extension from the gp41 six-helical bundle core structure in the post-fusion conformation[73] The NMR structure presented herein is incompatible with binding to MPER-directed bnAbs, suggesting that it most likely represents a state prior to the prehairpin intermediate, such as the pre-fusion or CD4-triggered conformation. Thus, without being bound by a particular theory, it is hypothesized that dequalinium blocks Env-mediated membrane fusion by preventing coreceptor-induced conformational changes. This suggests that the MPER in the pre-hairpin intermediate is conformationally dynamic and dequalinium may drive the equilibrium towards the conformation observed by NMR, thereby competing with 2F5 for gp41 binding allosterically.

Small-Molecule Fusion Inhibitors Targeting the MPER

Figure 8A:
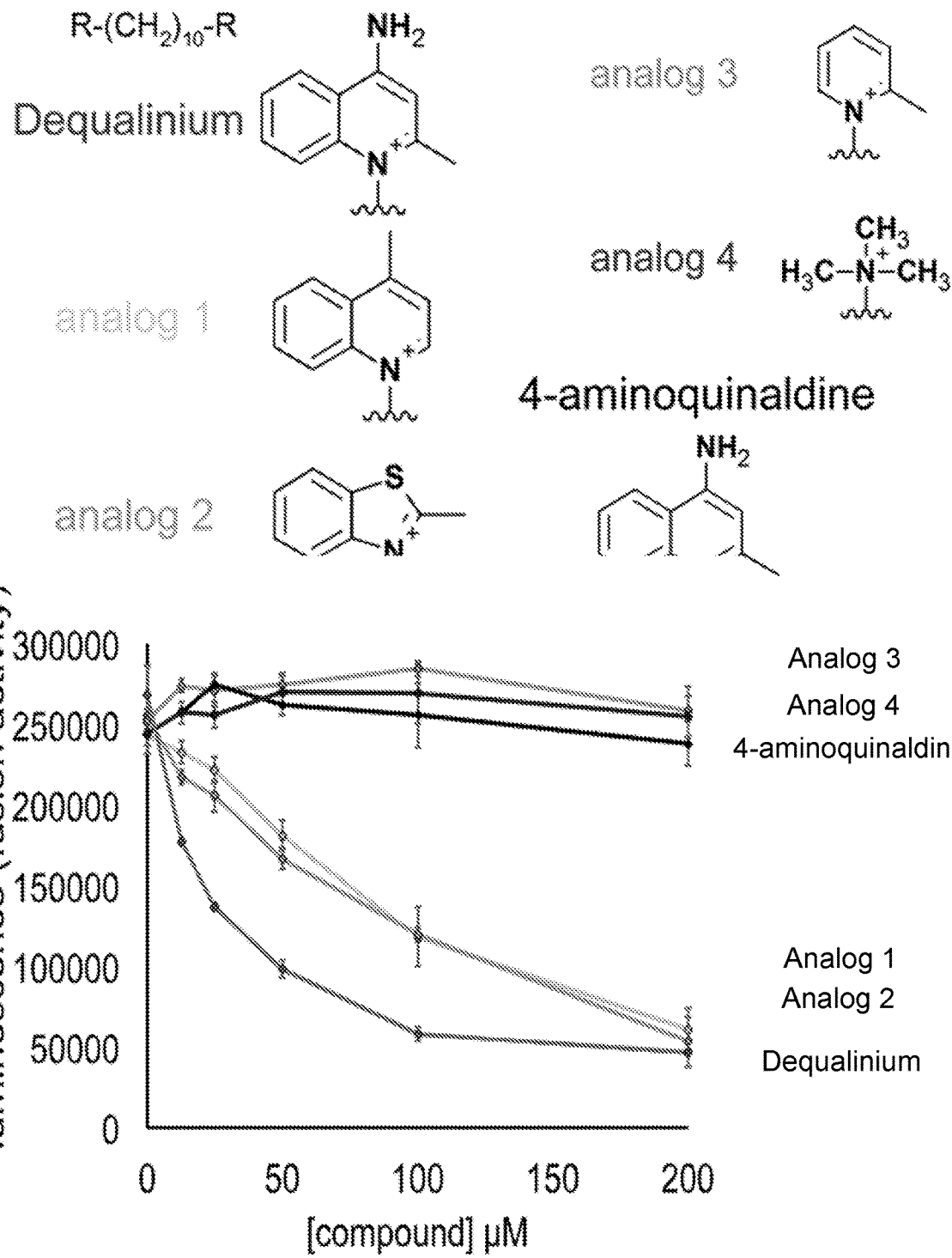
Figure 8B:
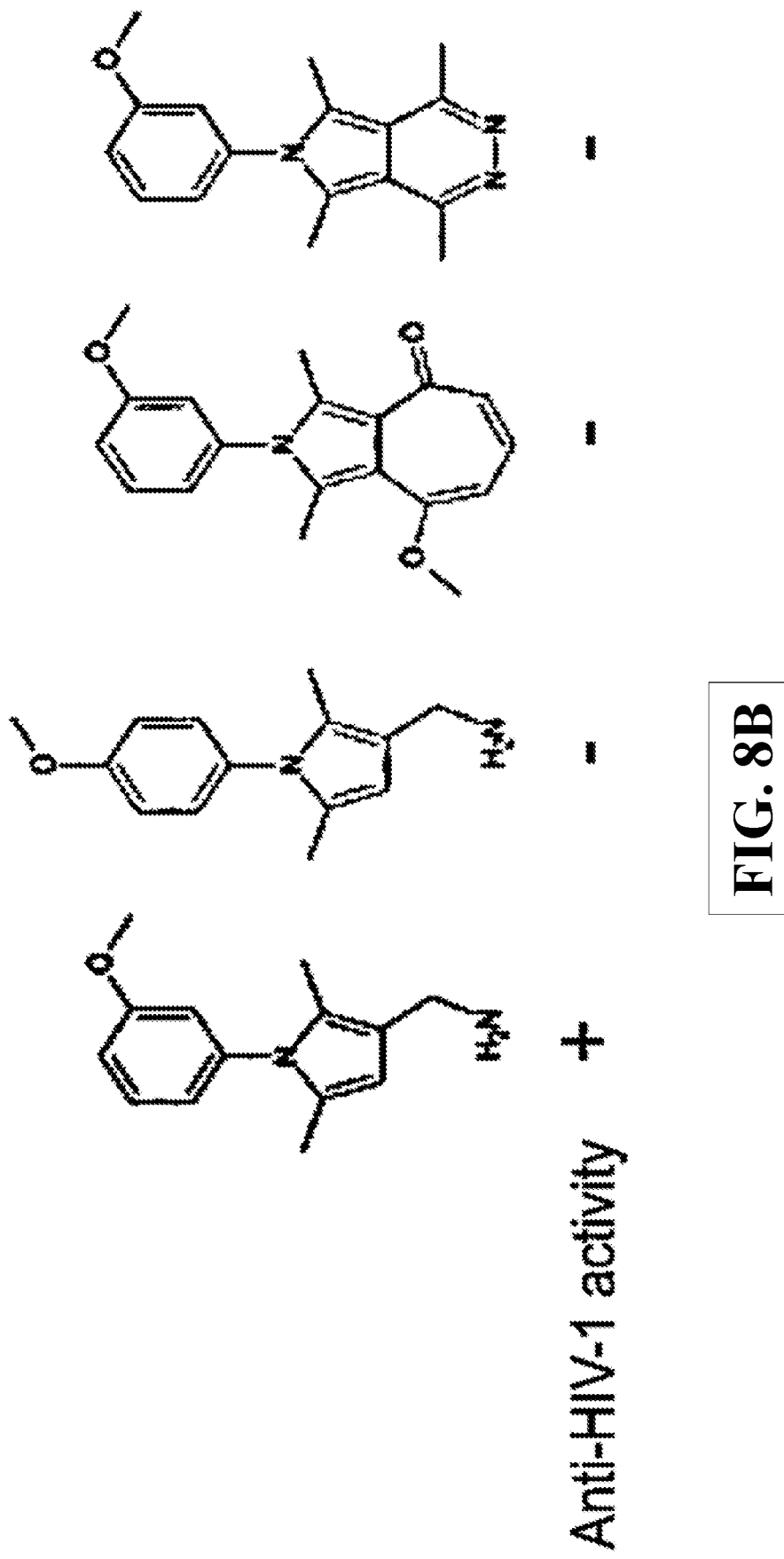

Modern drug discovery process includes a hit to lead (H2L) stage that involves hit confirmation and hit expansion, following the HTS. SAR profiles have been generated using commercially available analogs for dequalinium and C800, and performed the first round of SAR study using custom-synthesized dequalinium analogs (see below). The data and high-resolution structural information will be used, to guide further compound synthesis to identify promising leads that meet the criteria of high affinity to gp41-inter (in nM range), high selectivity to HIV-1 versus SIV, improved efficacy in cell-cell fusion and viral infectivity assays, druglikeness (molecular weight and lipophilicity), low cytotoxicity, as well as compound stability, solubility and synthetic tractability. In a pilot SAR study using commercial analogs, it has been observed that two additional dequalinium-like compounds with different head groups are also active, while the other two are not, in blocking HIV-1 Env mediated cell-cell fusion (FIG. 8A). The compound, 4-aminoquinaldine, containing the head group of dequalinium, showed no activity. None of these compounds showed significant cytotoxicity within the tested concentration range (not shown). In addition, more than 40 dimethyl pyrrole compounds were tested in the primary HTS assay and most of them have no anti-HIV-1 activity. Comparison of C800 and the inactive compounds suggest an initial SAR profile for this hit (FIG. 8B).

Figure 9A:
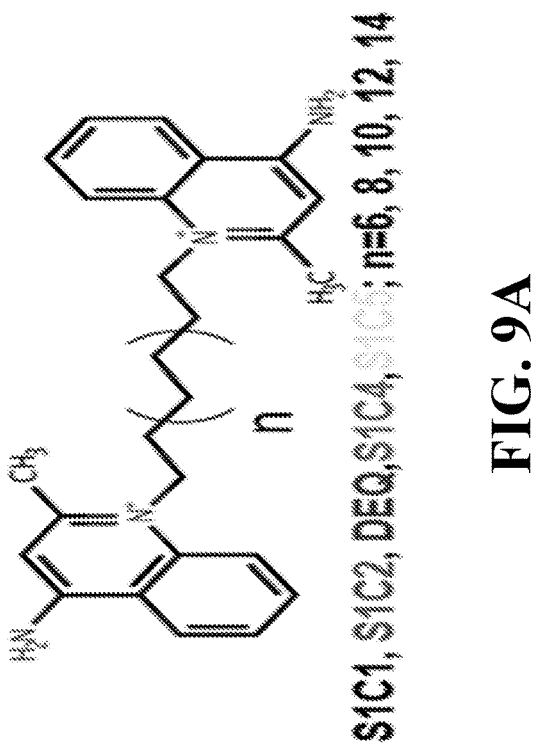
Figure 9B:
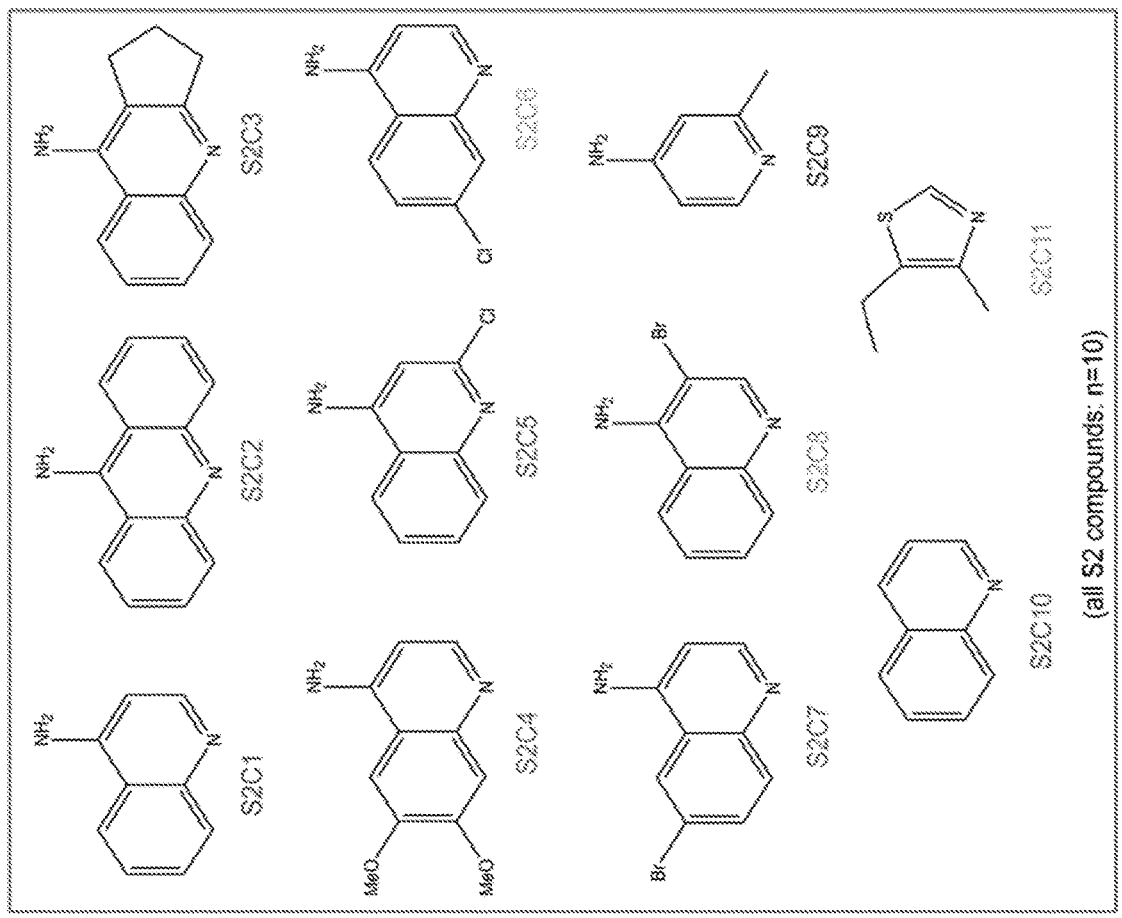
Figure 9C:
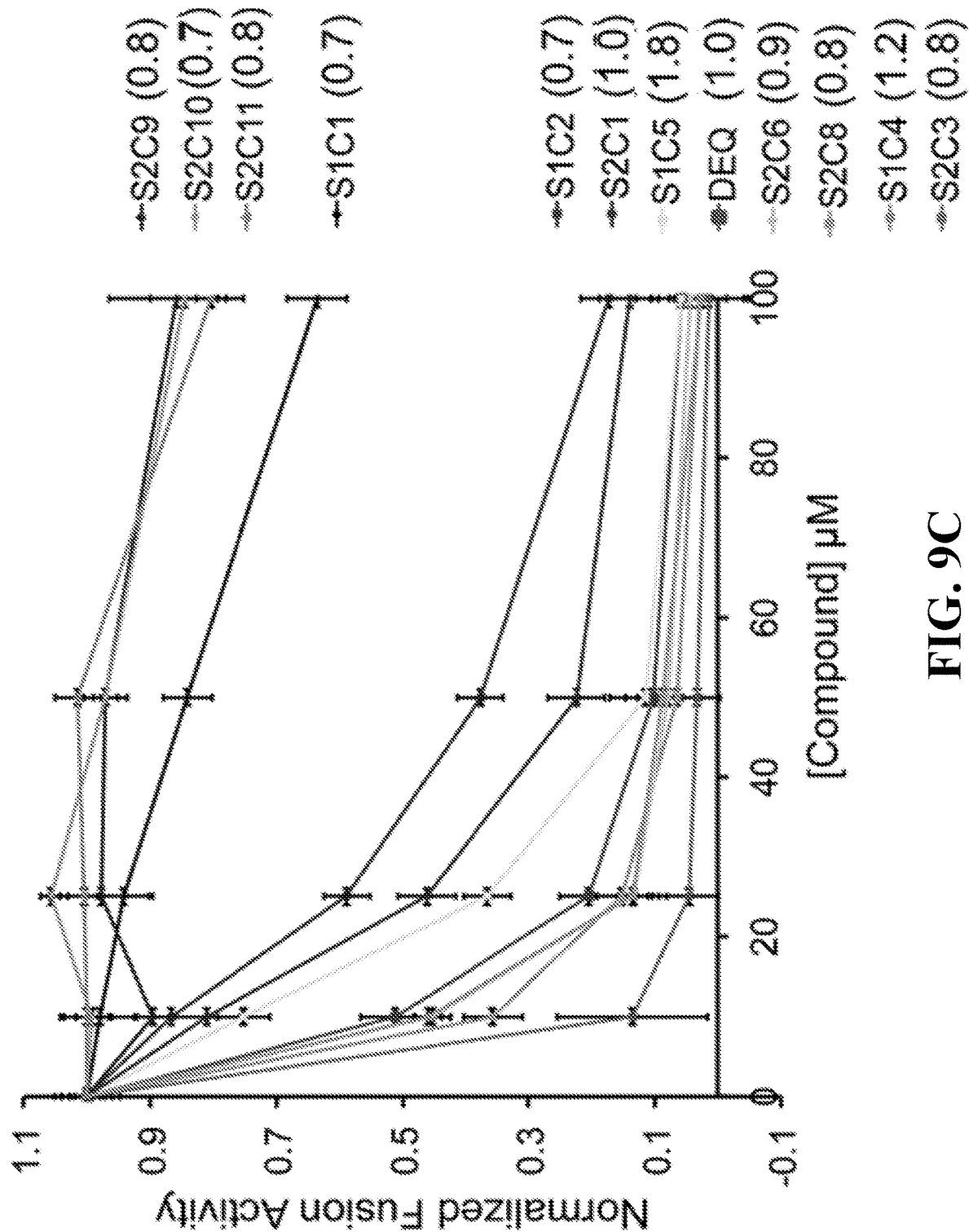

Dequalinium contains two aminoquinoline head groups connected by a 10 carbon linker. Medicinal chemistry was used to explore contributions from both the linker and the head groups. Linker lengths were varied from 6 to 14 carbons and different head groups were synthesized, as listed in FIG. 9A and FIG. 9B. For the head group, the 2-methyl group (S2C1) was removed, increased, or decreased the ring size of the head group (compounds S2C2, S2C3, S2C9, and S2C11), removed both the 4-amine and 2-methyl (S2C10) and also used different substituents on the quinoline ring (S2C4, S2C5, S2C6, S2C7 and S2C8). The inhibitory activity of the dequalinium analogs were tested in the cell-cell fusion assay, as well as their cytotoxicity. Most compounds showed toxicity comparable to that of dequalinium, as indicated by the relative toxicity, with S1C5 being the most toxic one (FIG. 9C). Inhibition potency increased with the increasing linker length, but peaked at a length of 12 carbons. Smaller groups such as S2C9 and S2C11 showed significant decreases in potency, as did the removal of the 2-methyl group (S2C1) and removal of 2-methyl and 4-amine (S2C10). Halogenated compounds S2C6 and S2C8 showed similar potency to dequalinium. A significant improvement was observed with compound S2C3, which contains the addition of a cyclopentyl group in the 2,3 positions, suggesting that larger hydrophobic groups in these positions enhance the potency.

Figure 10:
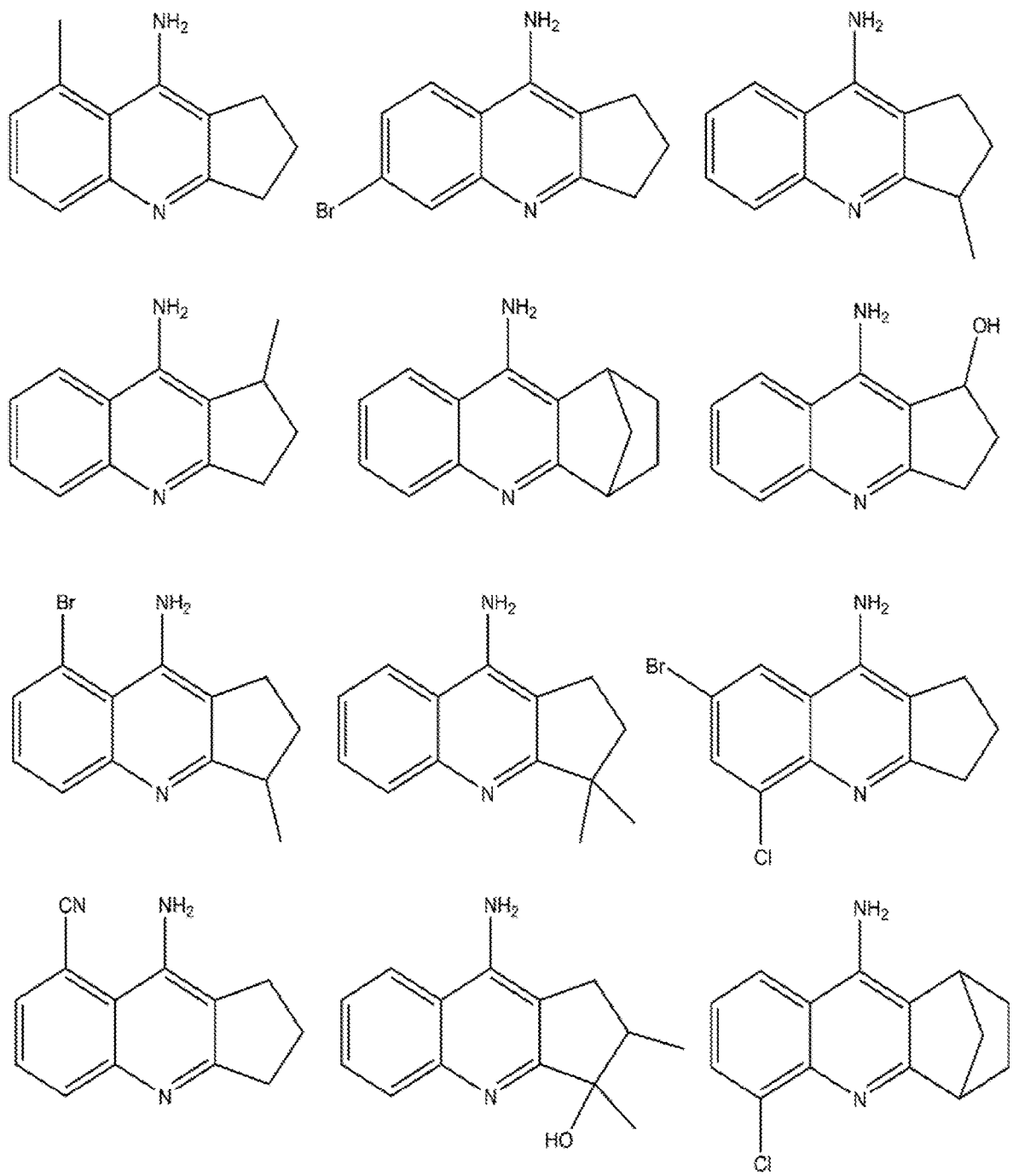
FIG. 10 shows the design of the second round of dequalinium analogs. Different head groups are designed based on the S2C3 scaffold using commercially available analogs.

Methods a. SAR studies on dequalinium. A large number of analogs of dequalinium have been reported through extensive SAR studies to explore its other biological effects, in addition to its antibacterial activity[74]. Several iterative rounds of medicinal chemistry will be done to generate two focused libraries. Library 1 optimizes the linker length, as preliminary SAR data showed the importance of the linker (FIGS. 10 and 11). To test linker lengths ranging from 4 to 20 carbons, 8-10 analogs will be produced following the published synthesis strategy[75]. Single- and double-head group versions will be compared. Library 2 optimizes the dequalinium head group, since the inhibitory activity was sensitive to substituents on the quinoline ring (FIGS. 10 and 11). Using commercially available 4-amino quanolinamine derivatives, a series of linked constructs will be synthesized to test the effects of substituents at various positions on the quinoline ring. Substituents will be selected to represent a diverse set of electron withdrawing, electron donating and steric groups.

The first round of custom synthesis was designed according to the general strategy described herein and has yielded a new promising lead compound, S2C3. A second set of compounds will be designed based on the S2C3 scaffold. Using commercially available analogs (FIG. 10) and previously established synthesis methods, to explore the effects of substituents on the cyclopentyl ring as well as the quinoline ring. New compounds were evaluated for affinity to gp41-inter, selectivity, efficacy in inhibition of HIV-1 membrane fusion, druglikeness, cytotoxicity, as well as compound stability, solubility and synthetic tractability. Results from these compounds can be used to direct future rounds of medicinal chemistry.

b. SAR studies on C800. The preliminary SAR profile of C800 suggests that its 3-methoxyphenyl and methylamine groups are useful for its anti-HIV-1 activity (FIG. 8B). This compound may therefore represent a minimal pharmacophore from which can be used to perform hit expansion. There are hundreds of commercially available derivatives of this compound containing additional substituents ranging from hydrogen bond donor/acceptors, charged groups and bulky hydrophobic group, located at various positions throughout the compound. These compounds will be tested for their anti-HIV-1 activity as well as other relevant properties and will make custom-synthesized compounds if necessary.

SAR studies guided by high-resolution structures. Once finalized, the high-resolution structure of the dequalinium-MPER complex, the Schrodinger small molecule drug discovery suite can be used to generate a virtual library of new compounds with many possible orientations and conformations within the binding site on the MPER and to predict favorable docking interactions. CombiGlide®[76] can be used such that it combines ligand-receptor scoring, combinatorial docking algorithms, and core-hopping technology, to design focused libraries and identify novel scaffolds; and Phase[77], which models pharmacophores based on spatial arrangements of chemical features critical for drug activities, to construct additional pharmacophores and hit compounds. Any new compounds can be evaluated using Glide[78,79] for binding mode predictions and Liaison[80] for binding affinity calculations. Compounds can be scored based on potential binding affinity, as well as considerations of druglike properties, such as those stated by "Lipinski's Rule"[81]. Iterative rounds of synthesis can be performed with focused libraries suggested by the docking. Compounds can be evaluated according to the flow-chart depicted in FIG. 11. Compounds with improved potency can be subjected to structural studies and evaluation of their SAR. The hit compound, dequalinium, is the active ingredient of several medications, such as DEQUADIN® and FLUOMIZINO, to treat bacterial infection[74,82]. It has also been tested for treatment of cancer and Malaria[75b83-85]. Hit optimization strategies may lead to identification of one or several more potent and druglike lead compounds related to dequalinium. In particular, once the molecular mechanism of how this compound binds the MPER and inhibits HIV-1 membrane fusion from the high-resolution structure of its complex with a gp41 construct, SAR studies of this compound can be much more effective. Currently, C800 is less advanced than dequalinium, but it can also produce promising lead compounds after optimization. The compound optimization system described herein will yield useful leads targeting the MPER of HIV-1 Env.

EXAMPLE 1, REFERENCES

1. Hammer, S. M. et al. A controlled trial of two nucleoside analogues plus indinavir in persons with human immunodeficiency virus infection and CD4 cell counts of 200 per cubic millimeter or less. AIDS Clinical Trials Group 320 Study Team. *The New England journal of medicine* 337, 725-33 (1997).
2. Gulick, R. M. et al. Treatment with indinavir, zidovudine, and lamivudine in adults with human immunodeficiency virus infection and prior antiretroviral therapy. *The New England journal of medicine* 337, 734-9 (1997).
3. Palella, F. J., Jr. et al. Declining morbidity and mortality among patients with advanced human immunodeficiency virus infection. HIV Outpatient Study Investigators. *The New England journal of medicine* 338, 853-60 (1998).
4. Kilby, J. M. & Eron, J. J. Novel therapies based on mechanisms of HIV-1 cell entry. *N Engl J Med* 348, 2228-38 (2003).
5. Robertson, D. US FDA approves new class of HIV therapeutics. *Nature biotechnology* 21, 470-1 (2003).
6. Poveda, E. et al. Dynamics of enfuvirtide resistance in HIV-infected patients during and after long-term enfuvirtide salvage therapy. *Journal of clinical virology: the official publication of the Pan American Society for Clinical Virology* 34, 295-301 (2005).
7. Poveda, E. et al. Evolution of genotypic and phenotypic resistance to Enfuvirtide in HIV-infected patients experiencing prolonged virologic failure. *Journal of medical virology* 74, 21-8 (2004).
8. Sista, P. R. et al. Characterization of determinants of genotypic and phenotypic resistance to enfuvirtide in baseline and on-treatment HIV-1 isolates. *Aids* 18, 1787-94 (2004).
9. Harrison, S. C. Viral membrane fusion. *Nature structural & molecular biology* 15, 690-8 (2008).
10. Chan, D. C. & Kim, P. S. HIV entry and its inhibition. *Cell* 93, 681-4 (1998).
11. Frey, G. et al. A fusion-intermediate state of HIV-1 gp41 targeted by broadly neutralizing antibodies. *Proc Natl Acad Sci USA* 105, 3739-44 (2008).
12. Alam, S. M. et al. Role of HIV membrane in neutralization by two broadly neutralizing antibodies. *Proc Natl Acad Sci USA* 106, 20234-9 (2009).
13. Chen, J. et al. Mechanism of HIV-1 neutralization by antibodies targeting a membrane-proximal region of gp41. *Journal of virology* 88, 1249-58 (2014).
14. Stephenson, K. E. & Barouch, D. H. A global approach to HIV-1 vaccine development. *Immunological reviews* 254, 295-304 (2013).
15. Haynes, B. F. & McElrath, M. J. Progress in HIV-1 vaccine development. *Current opinion in HIV and AIDS* 8, 326-32 (2013).
16. Grant, M., Samuel, R., Bettiker, R. L. & Suh, B. Antiretroviral therapy 2010 update: current practices and controversies. *Archives of pharmacal research* 34, 1045-53 (2011).
17. Thompson, M. A. et al. Antiretroviral treatment of adult HIV infection: 2012 recommendations of the International Antiviral Society-USA panel. *JAMA: the journal of the American Medical Association* 308, 387-402 (2012).
18. Harrison, S. C. Mechanism of membrane fusion by viral envelope proteins. *Advances in Virus Research* 64, 231-259 (2005).
19. Weissenhorn, W., Dessen, A., Harrison, S. C., Skehel, J. J. & Wiley, D. C. Atomic structure of the ectodomain from HIV-1 gp41. *Nature* 387, 426-430 (1997).
20. Chan, D. C., Fass, D., Berger, J. M. & Kim, P. S. Core structure of gp41 from the HIV envelope glycoprotein. *Cell* 89, 263-273 (1997).
21. Julien, J. P. et al. Crystal structure of a soluble cleaved HIV-1 envelope trimer. *Science* 342, 1477-83 (2013).
22. Lyumkis, D. et al. Cryo-EM structure of a fully glycosylated soluble cleaved HIV-1 envelope trimer. *Science* 342, 1484-90 (2013).
23. Pancera, M. et al. Structure and immune recognition of trimeric pre-fusion HIV-1 Env. *Nature* 514, 455-61 (2014).
24. Chernomordik, L. V. & Kozlov, M. M. Mechanics of membrane fusion. *Nat Struct Mol Biol* 15, 675-83 (2008).
25. Dimitrov, A. S., Rawat, S. S., Jiang, S. & Blumenthal, R. Role of the fusion peptide and membrane-proximal domain in HIV-1 envelope glycoprotein-mediated membrane fusion. *Biochemistry* 42, 14150-8 (2003).
26. Munoz-Barroso, I., Salzwedel, K., Hunter, E. & Blumenthal, R. Role of the membrane-proximal domain in the initial stages of human immunodeficiency virus type 1 envelope glycoprotein-mediated membrane fusion. *Journal of virology* 73, 6089-92 (1999).
27. Salzwedel, K., West, J. T. & Hunter, E. A conserved tryptophan-rich motif in the membrane-proximal region of the human immunodeficiency virus type 1 gp41 ectodomain is important for Env-mediated fusion and virus infectivity. *Journal of virology* 73, 2469-80 (1999).
28. Muster, T. et al. A conserved neutralizing epitope on gp41 of human immunodeficiency virus type 1. *J Virol* 67, 6642-7 (1993).
29. Stiegler, G. et al. A potent cross-Glade neutralizing human monoclonal antibody against a novel epitope on gp41 of human immunodeficiency virus type 1. *AIDS Res Hum Retroviruses* 17, 1757-65 (2001).
30. Huang, J. et al. Broad and potent neutralization of HIV-1 by a gp41-specific human antibody. *Nature* 491, 406-12 (2012).
31. Trkola, A. et al. Delay of HIV-1 rebound after cessation of antiretroviral therapy through passive transfer of human neutralizing antibodies. *Nature medicine* 11, 615-22 (2005).
32. Malbec, M. et al. Broadly neutralizing antibodies that inhibit HIV-1 cell to cell transmission. *J Exp Med* 210, 2813-21 (2013).
33. Frey, G. et al. Distinct conformational states of HIV-1 gp41 are recognized by neutralizing and non-neutralizing antibodies. *Nature structural & molecular biology* 17, 1486-91 (2010).
34. Ullmann, A., Jacob, F. & Monod, J. Characterization by in vitro complementation of a peptide corresponding to an operator-proximal segment of the beta-galactosidase structural gene of *Escherichia coli*. *Mol Biol* 24, 339-43 (1967).
35. Dev, J. et al. Structural basis for membrane anchoring of HIV-1 envelope spike. *Science* 353, 172-5 (2016).
36. Weissenbacher, E. R. et al. A comparison of dequalinium chloride vaginal tablets (Fluomizin(R)) and clindamycin vaginal cream in the treatment of bacterial vaginosis: a single-blind, randomized clinical trial of efficacy and safety. *Gynecol Obstet Invest* 73, 8-15 (2012).
37. Nkolola, J. P. et al. Breadth of neutralizing antibodies elicited by stable, homogeneous Glade A and Glade C HIV-1 gp140 envelope trimers in guinea pigs. *Journal of virology* 84, 3270-9 (2010).
38. Li, M. et al. Human immunodeficiency virus type 1 env clones from acute and early subtype B infections for standardized assessments of vaccine-elicited neutralizing antibodies. *J Virol* 79, 10108-25 (2005).
39. Mascola, J. R. et al. Recommendations for the design and use of standard virus panels to assess neutralizing antibody responses elicited by candidate human immunodeficiency virus type 1 vaccines. *J Virol* 79, 10103-7 (2005).
40. Chen, J. et al. HIV-1 ENVELOPE. Effect of the cytoplasmic domain on antigenic characteristics of HIV-1 envelope glycoprotein. *Science* 349, 191-5 (2015).
41. Kovacs, J. M. et al. HIV-1 envelope trimer elicits more potent neutralizing antibody responses than monomeric gp120. *Proceedings of the National Academy of Sciences of the United States of America* 109, 12111-6 (2012).
42. Edmonds, T. G. et al. Replication competent molecular clones of HIV-1 expressing Renilla luciferase facilitate the analysis of antibody inhibition in PBMC. *Virology* 408, 1-13 (2010).
43. Piai, A., Fu, Q., Dev, J. & Chou, J. J. Optimal Bicelle Size q for Solution NMR Studies of the Protein Transmembrane Partition. *Chemistry* 23, 1361-1367 (2017).

44. Liu, J., Bartesaghi, A., Borgnia, M. J., Sapiro, G. & Subramaniam, S. Molecular architecture of native HIV-1 gp120 trimers. *Nature* 455, 109-13 (2008).
45. Schwieters, C. D., Kuszewski, J. J., Tjandra, N. & Clore, G. M. The Xplor-NIH NMR molecular structure determination package. *J Magn Reson* 160, 65-73 (2003).
46. Cheng, Y. Single-Particle Cryo-EM at Crystallographic Resolution. *Cell* 161, 450-7 (2015).
47. Cheng, Y., Grigorieff, N., Penczek, P. A. & Walz, T. A primer to single-particle cryo-electron microscopy. *Cell* 161, 438-49 (2015).
48. Merk, A. et al. Breaking Cryo-EM Resolution Barriers to Facilitate Drug Discovery. *Cell* 165, 1698-707 (2016).
49. Banerjee, S. et al. 2.3 A resolution cryo-EM structure of human p97 and mechanism of allosteric inhibition. *Science* 351, 871-5 (2016).
50. Meyerson, J. R. et al. Structural basis of kainate subtype glutamate receptor desensitization. *Nature* 537, 567-571 (2016).
51. Bartesaghi, A. et al. 2.2 A resolution cryo-EM structure of beta-galactosidase in complex with a cell-permeant inhibitor. *Science* 348, 1147-51 (2015).
52. Gao, Y., Cao, E., Julius, D. & Cheng, Y. TRPV1 structures in nanodiscs reveal mechanisms of ligand and lipid action. *Nature* 534, 347-51 (2016).
53. Shen, P. S. et al. The Structure of the Polycystic Kidney Disease Channel PKD2 in Lipid Nanodiscs. *Cell* 167, 763-773 e11 (2016).
54. Brown, A. et al. Structure of the large ribosomal subunit from human mitochondria. *Science* 346, 718-22 (2014).
55. Wan, R., Yan, C., Bai, R., Huang, G. & Shi, Y. Structure of a yeast catalytic step I spliceosome at 3.4 A resolution. *Science* 353, 895-904 (2016).
56. Bai, X. C. et al. An atomic structure of human gamma-secretase. *Nature* 525, 212-7 (2015).
57. Mi, W. et al. Structural basis of MsbA-mediated lipopolysaccharide transport. *Nature* 549, 233-237 (2017).
58. Schoebel, S. et al. Cryo-EM structure of the protein-conducting ERAD channel Hrd1 in complex with Hrd3. *Nature* 548, 352-355 (2017).
59. Ishima, R. Protein-Inhibitor Interaction Studies Using NMR. *Appl NMR Spectrosc* 1, 143-181 (2015).
60. Oxenoid, K. & Chou, J. J. A functional NMR for membrane proteins: dynamics, ligand binding, and allosteric modulation. *Protein Sci* 25, 959-73 (2016).
61. Otwinowski, Z. & Minor, W. Processing of X-ray diffraction data collected in oscillation mode. *Methods Enzymology* 276, 307-326 (1997).
62. Kabsch, W. Xds. *Acta crystallographica. Section D, Biological crystallography* 66, 125-32 (2010).
63. McCoy, A. J. et al. Phaser crystallographic software. *J Appl Crystallogr* 40, 658-674 (2007).
64. Collaborative Computational Project, N. The CCP4 suite: programs for protein crystallography. *Acta Crystallogr D Biol Crystallogr* 50, 760-3 (1994).
65. Emsley, P., Lohkamp, B., Scott, W. G. & Cowtan, K. Features and development of Coot. *Acta crystallographica. Section D, Biological crystallography* 66, 486-501 (2010).
66. Murshudov, G. N. Refinement of macromolecular structures by the maximum-likelihood method. *Acta Crystallogr D Biol Crystallogr* 53, 240-55 (1997).
67. Adams, P. D. et al. PHENIX: a comprehensive Python-based system for macromolecular structure solution. *Acta crystallographica. Section D, Biological crystallography* 66, 213-21 (2010).
68. Mastronarde, D. N. Automated electron microscope tomography using robust prediction of specimen movements. *Journal of structural biology* 152, 36-51 (2005).
69. Zheng, S. Q. et al. MotionCor2: anisotropic correction of beam-induced motion for improved cryo-electron microscopy. *Nat Methods* 14, 331-332 (2017).
70. Rohou, A. & Grigorieff, N. CTFFIND4: Fast and accurate defocus estimation from electron micrographs. *J Struct Biol* 192, 216-21 (2015).
71. Scheres, S. H. RELION: implementation of a Bayesian approach to cryo-EM structure determination. *J Struct Biol* 180, 519-30 (2012).
72. Morin, A. et al. Collaboration gets the most out of software. *Elife* 2, e01456 (2013).
73. Buzon, V. et al. Crystal structure of HIV-1 gp41 including both fusion peptide and membrane proximal external regions. *PLoS pathogens* 6, e1000880 (2010).
74. Tischer, M., Pradel, G., Ohlsen, K. & Holzgrabe, U. Quaternary ammonium salts and their antimicrobial potential: targets or nonspecific interactions? *ChemMedChem* 7, 22-31 (2012).
75. Qin, D., Sullivan, R., Berkowitz, W. F., Bittman, R. & Rotenberg, S.A. Inhibition of protein kinase C(alpha) by dequalinium analogues: dependence on linker length and geometry. *J Med Chem* 43, 1413-7 (2000).
76. *Schrödinger Release 2014-1: CombiGlide, version 3.2*, (New York, N.Y., 2014).
77. Dixon, S. L., Smondyrev, A. M. & Rao, S. N. PHASE: a novel approach to pharmacophore modeling and 3D database searching. *Chemical biology & drug design* 67, 370-2 (2006).
78. Friesner, R. A. et al. Glide: a new approach for rapid, accurate docking and scoring. 1. Method and assessment of docking accuracy. *Journal of medicinal chemistry* 47, 1739-49 (2004).
79. Halgren, T. A. et al. Glide: a new approach for rapid, accurate docking and scoring. 2. Enrichment factors in database screening. *Journal of medicinal chemistry* 47, 1750-9 (2004).
80. *Small-Molecule Drug Discovery Suite 2014-1: Liaison, version 6.2*, (New York, N.Y., 2014).
81. Lipinski, C. A., Lombardo, F., Dominy, B. W. & Feeney, P. J. Experimental and computational approaches to estimate solubility and permeability in drug discovery and development settings. *Advanced drug delivery reviews* 46, 3-26 (2001).
82. Mendling, W., Weissenbacher, E. R., Gerber, S., Prasauskas, V. & Grob, P. Use of locally delivered dequalinium chloride in the treatment of vaginal infections: a review. *Arch Gynecol Obstet* 293, 469-84 (2016).
83. Abeywickrama, C., Rotenberg, S. A. & Baker, A.D. Inhibition of protein kinase C by dequalinium analogues: structure-activity studies on head group variations. *Bioorg Med Chem* 14, 7796-803 (2006).

84. Berger, O. et al. Reverse-benzamidine antimalarial agents: design, synthesis, and biological evaluation. *Bioorg Med Chem Lett* 20, 5815-7 (2010).

85. Weiss, M. J. et al. Dequalinium, a topical antimicrobial agent, displays anticarcinoma activity based on selective mitochondrial accumulation. *Proc Natl Acad Sci USA* 84, 5444-8 (1987).

Example 2

Small-Molecule Fusion Inhibitors Targeting the Membrane Proximal External Region of HIV-1 Envelope Spike Combination antiretroviral therapy (cART) using different classes of antiviral therapeutics has transformed HIV-1 infection, once a fatal illness, to a manageable chronic condition. Drug resistance, severe side effects and difficulties in treatment compliance have brought challenges to the implementation of the cART in clinical settings and indicate the need for additional molecular targets. Peptides derived from HIV-1 gp41, such as Enfuvirtide, are still the only fusion inhibitors approved for clinical use. Described herein are several small-molecule fusion inhibitors, guided by a broadly neutralizing antibody, against an extensively studied vaccine target—the membrane proximal external region (MPER) of HIV-1 envelope (Env) spikes. These compounds specifically inhibit the membrane fusion mediated by HIV-1 Env in both cell-cell fusion and viral infectivity assays. An NMR structure of the most potent compound complexed with a trimeric MPER construct in the context of lipid bilayer reveals that the compound partially inserts into a hydrophobic binding pocket formed exclusively by the MPER residues, thereby blocking conformational changes of Env required for membrane fusion. These results suggest that the MPER is a potential therapeutic target for developing orally available, small-molecule fusion inhibitors and that strategies employing an antibody-guided search for novel therapeutics may be applied to other human diseases.
Introduction Combination antiretroviral therapy (cART) has transformed HIV-1 infection from a once fatal illness into a manageable chronic condition[1-3]. The latest cART regimen uses several classes of antiviral therapeutics, including nucleoside/nucleotide reverse transcriptase inhibitors (NRTIs), non-nucleoside reverse transcriptase inhibitors (NNRTIs), protease inhibitors (PIs), fusion inhibitors (FIs), coreceptor inhibitors (CRIs) and integrase inhibitors (INIs)[4,5]. A typical therapy requires a combination of three or more drugs from at least two classes. Drug resistance, severe side effects and difficulties in patient compliance all call for additional drugs and drug targets. The first fusion inhibitor approved by FDA is Enfuvirtide, a 36-residue peptide derived from gp41[6,7]. It has to be stored at low temperature, freshly reconstituted and injected subcutaneously twice a day. Moreover, injection site reactions, rapid emergence of resistant viruses and high cost of production have limited its long-term use[8-10]. The next-generation gp41 peptide-based fusion inhibitors, such as Sifuvirtide and Albuvirtide, may suffer similar disadvantages[11-13]. Many patients previously treated with Enfuvirtide have switched to oral CRIs[14], thereby reducing the power of one of the potent weapons from the anti-HIV-1 arsenal. Developing orally available small-molecule fusion inhibitors to overcome the limitations of peptide-based drugs is highly desirable.

HIV-1 envelope spike (Env) mediates fusion of viral and target cell membranes to initiate infection[15]. The Env polypeptide chain is produced as a precursor, gp160, which trimerizes to (gp160)³ and then undergoes cleavage by a furin-like protease into two non-covalently associated fragments: the receptor-binding fragment gp120 and the fusion fragment gp41[16]. Three copies of each fragment constitute the mature viral spike (gp120/gp41)³. Sequential binding of gp120 to primary receptor CD4 and a coreceptor is believed to induce a cascade of refolding events in gp41[17,18]. Gp41, with its C-terminal transmembrane segment inserted in the viral membrane, folds into a pre-fusion conformation within the precursor gp160[19-21]. Cleavage between gp120 and gp41 makes the protein metastable with respect to the post-fusion conformation. When triggered, the N-terminal fusion peptide of gp41 translocates and inserts into the target cell membrane. The extended conformation of gp41, with the fusion peptide inserted into the target cell membrane and the transmembrane anchor in the viral membrane, is referred to as the prehairpin intermediate[22]. This state is targeted by Enfuvirtide[6], as well as by certain broadly neutralizing antibodies (bnAbs), including 2F5, 4E10 and 10E8[23-25]. Subsequent rearrangements involve refolding of gp41 into a hairpin conformation, creating a six-helix bundle known as the post-fusion conformation, which brings the two membranes together and leads to membrane fusion. Success of Enfuvirtide and Albuvirtide as effective therapeutics demonstrate that blocking gp41 refolding steps represents an effective antiviral strategy.

Figure 2A:
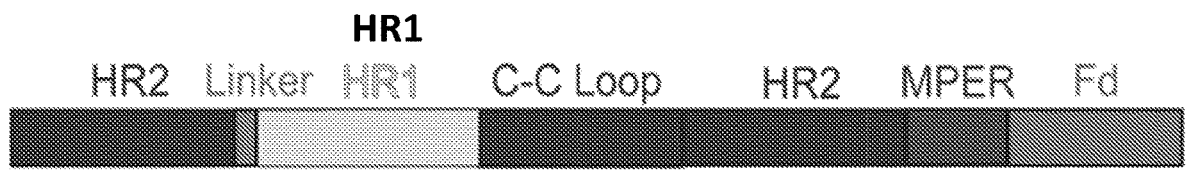
Figure 2B:
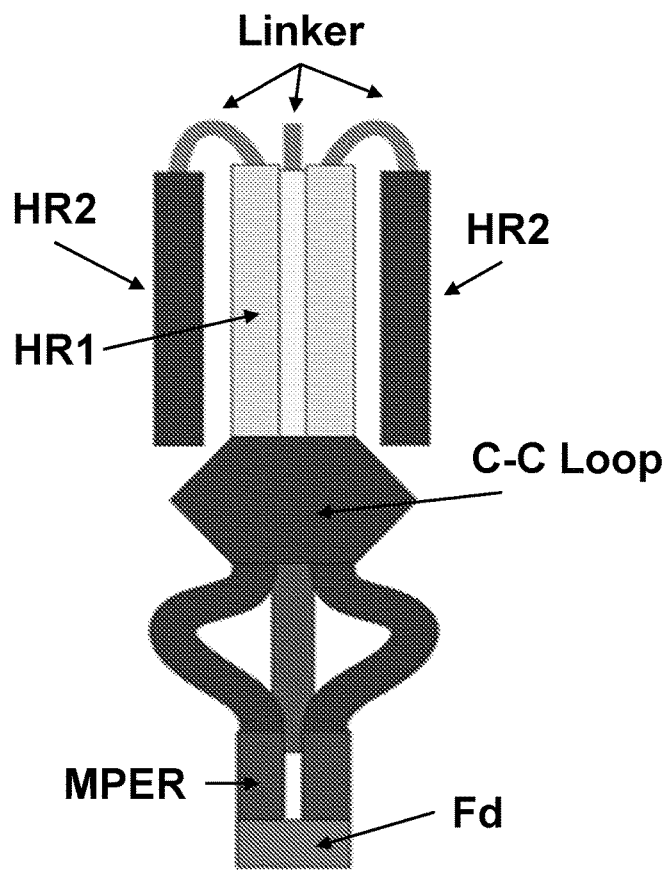
Figure 2C:
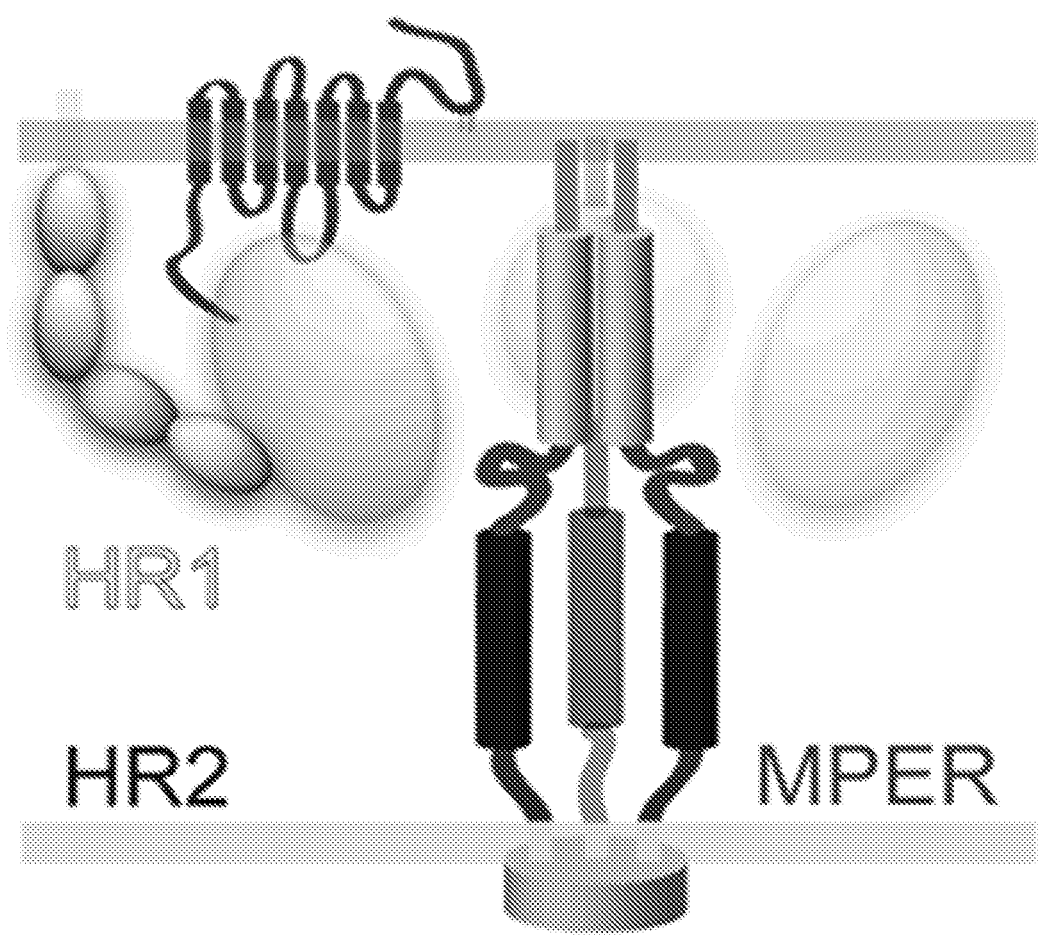

The MPER, a hydrophobic region of ~25 residues, adjacent to the viral membrane, is one of the most conserved regions in gp41 and is required for viral infectivity[26-28]. It is an extensively studied vaccine target recognized by a number of anti-gp41 bnAbs, including 2F5, 4E10, Z13e1 and 10E8[29-31]. Its role in the mechanism of viral fusion is still unknown. These antibodies appear to block HIV-1 infection by a common mechanism—they bind the pre-hairpin intermediate state of gp41 with the help of their lipid binding activity[23-25]. Despite their remarkable neutralization potencies against a wide spectrum of HIV-1 isolates in vitro, studies involving passive transfer of 2F5 and 4E10 in HIV-1 infected patients suggest that the antibodies may not be effective in blocking HIV-1 propagation in vivo[32]. It was investigated whether small-molecule compounds can mimic these bnAbs to bind the MPER and specifically block HIV-1 Env-mediated membrane fusion. Using a high throughput screen involving competition with 2F5, several such small-molecule fusion inhibitors were identified. These compounds are promising leads that can be further optimized. The structural studies by NMR show that the compounds target a hydrophobic binding pocket formed by the trimeric MPER, suggesting they block HIV-1 infection by preventing conformational changes in gp41 required for membrane fusion. Thus, the MPER, a long sought-after vaccine target, is also a potential therapeutic site for developing orally available, small-molecule fusion inhibitors. In addition, the antibody-guided search for novel therapeutics presented here should be a general strategy that may be applied to other human diseases.
Results
Identification of Small-Molecule Fusion Inhibitors Targeting the MPER A construct designed previously, designated gp41-inter, captures the prehairpin intermediate conformation of gp41 using the following sequence: (HR2)-linker[HR1-CCloop-HR2-MPER]-(trimerization foldon tag)[23] (FIG. 2A-2C). When the gp41-inter polypeptide chains trimerize, the N-terminal HR2 segments form a six-helix bundle with the HR1 segments, because the C-terminal HR2 segments, constrained by the foldon tag, will be unable to form a six-helix bundle. This construct thus can be pictured as the prehairpin intermediate captured by a covalently-linked HR2 peptide, such as Enfuvirtide (FIG. 2A-2C). The purified gp41-inter protein is a stable and soluble trimer in solution. Extensive biochemical and antigenicity studies of gp41-inter have confirmed that it indeed represents the prehairpin intermediate conformation of gp41[22-25,33].

Figures 3A, 3B, 3C:
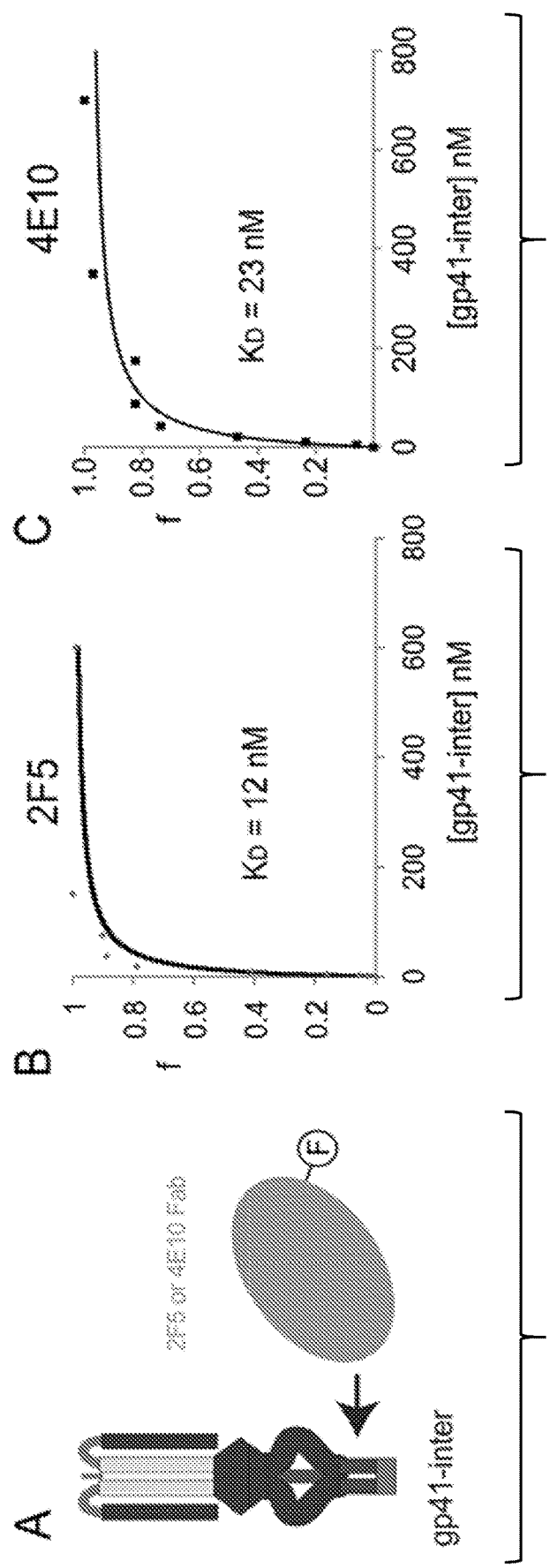

To screen small-molecule compounds that bind the MPER and may mimic the neutralizing antibodies to abort membrane fusion, a sensitive, fluorescence polarization (FP) assay to detect binding of 2F5 to gp41-inter was developed (FIG. 3A). Any compound that binds the antibody epitope with high enough affinity can disrupt this interaction and compete for binding to gp41-inter. Fluorescein isothiocyanate (FITC)-labeled 2F5 Fab bound with high affinity ($K_D$=12 nM) to gp41-inter as measured by fluorescence polarization (FIG. 3B). Unlabeled antibody effectively competed with the labeled Fab to diminish the fluorescence signal. The Z' factor was 0.52 for this assay when the unlabeled Fab was used as a positive control and DMSO as a negative control, suggesting it was suitable for high throughput screening (HTS). A secondary assay was established by substituting gp41-inter with a short corresponding epitope peptide of 2F5 in the primary assay to distinguish compounds that bind the antibody from those that bind gp41-inter. The epitope peptide is flexible and has no defined structure in solution; compounds that specifically interact with the gp41-inter trimer would not bind the unstructured, monomeric peptide to block the peptide-antibody interaction, but those that bind the antibody would interfere with its binding to both the peptide and gp41-inter.

In this case, the labeled peptide and unlabeled antibody were used, which yielded the best signals for fluorescence polarization. A screen was completed with 162,106 compounds from chemical libraries. All screening was performed in duplicate, using the labeled 2F5 Fab. Any compounds that fluoresce or scatter light, thus interfering with the FP assay were eliminated. Duplicate values were averaged and selected those with a Z score of 5 or greater. The 146 compounds meeting these criteria as "hits" were considered, giving a hit rate of 0.09%. Further hits were screened by surface plasmon resonance (SPR) for binding to gp41-inter but not to 2F5, and for their ability to inhibit cell-cell fusion mediated by HIV-1 Env but not by SIV Env.

Figure 5A:
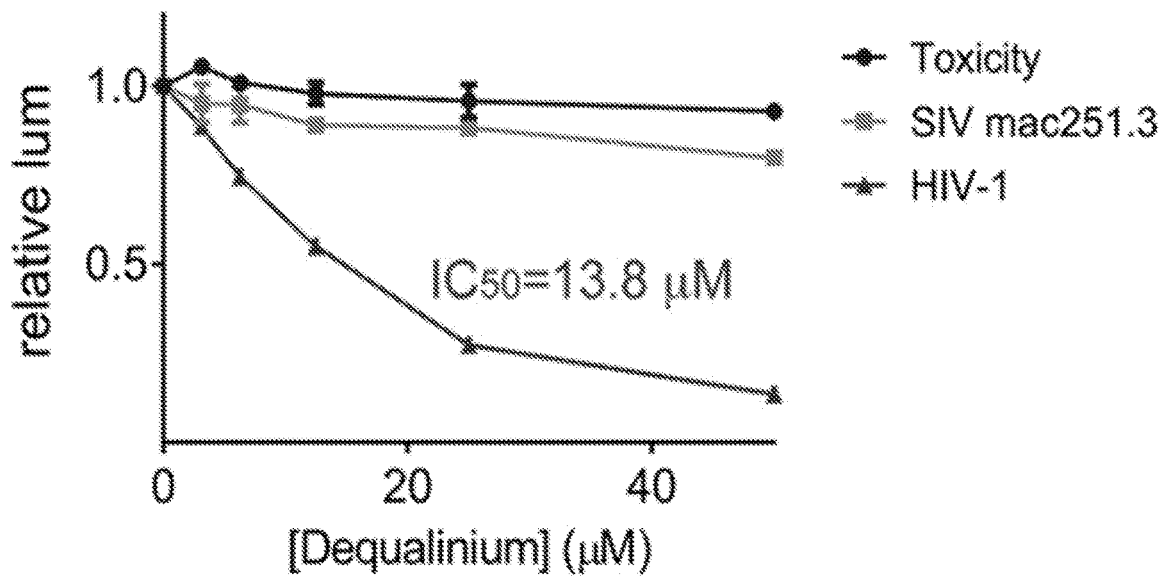
Figure 5B:
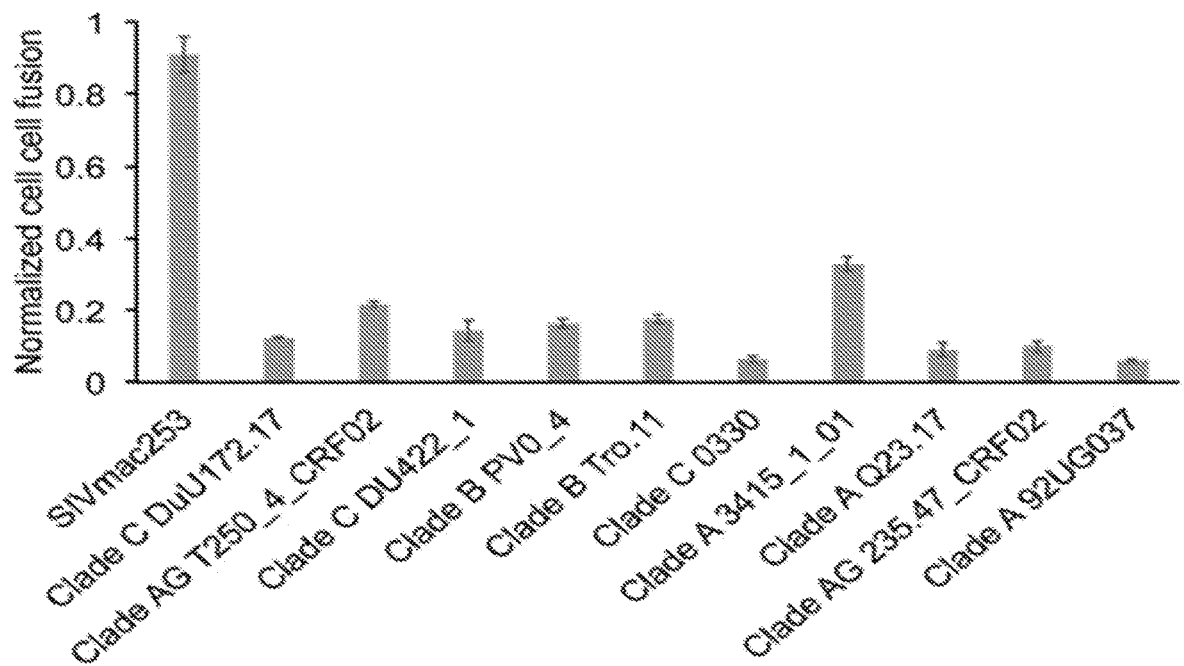
Figure 5C:
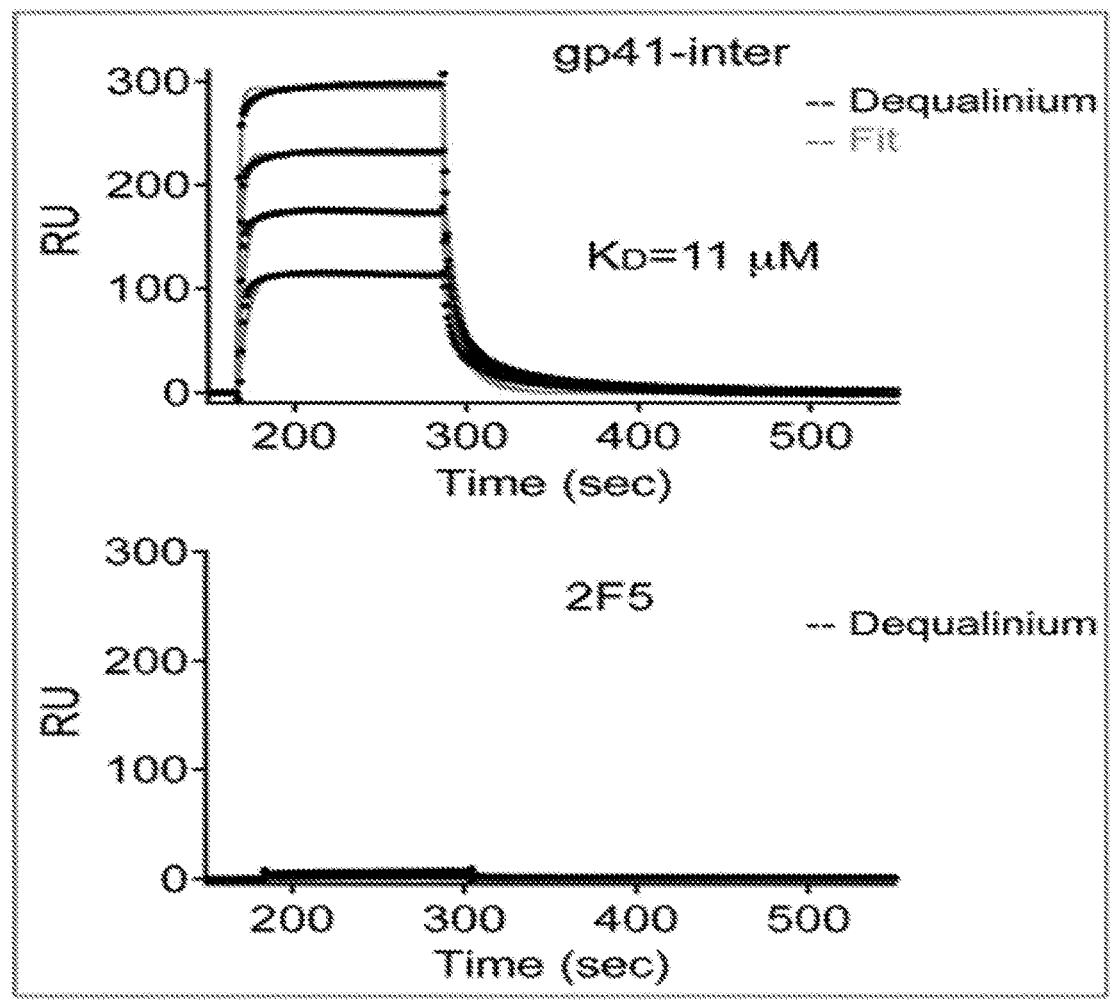
Figure 5D:
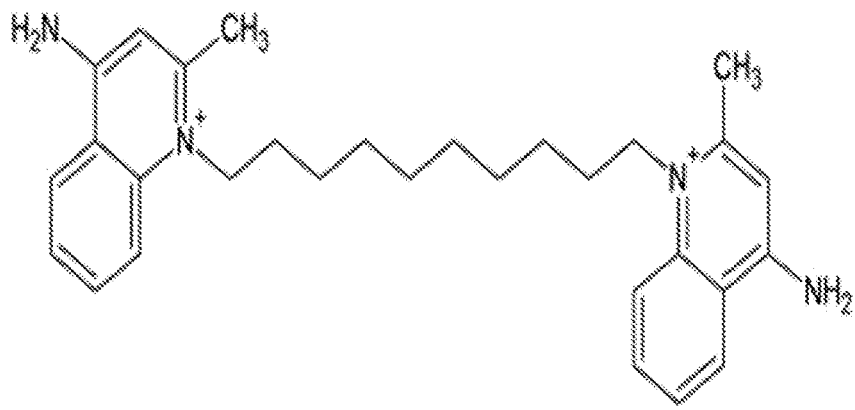
Figure 5E:
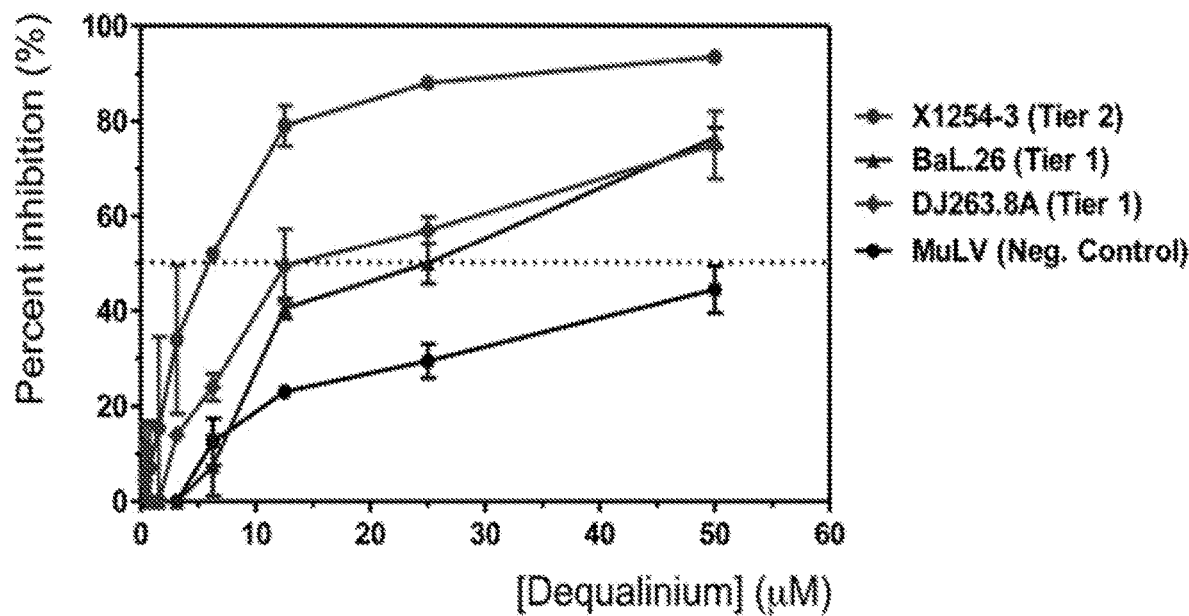
Figure 6:
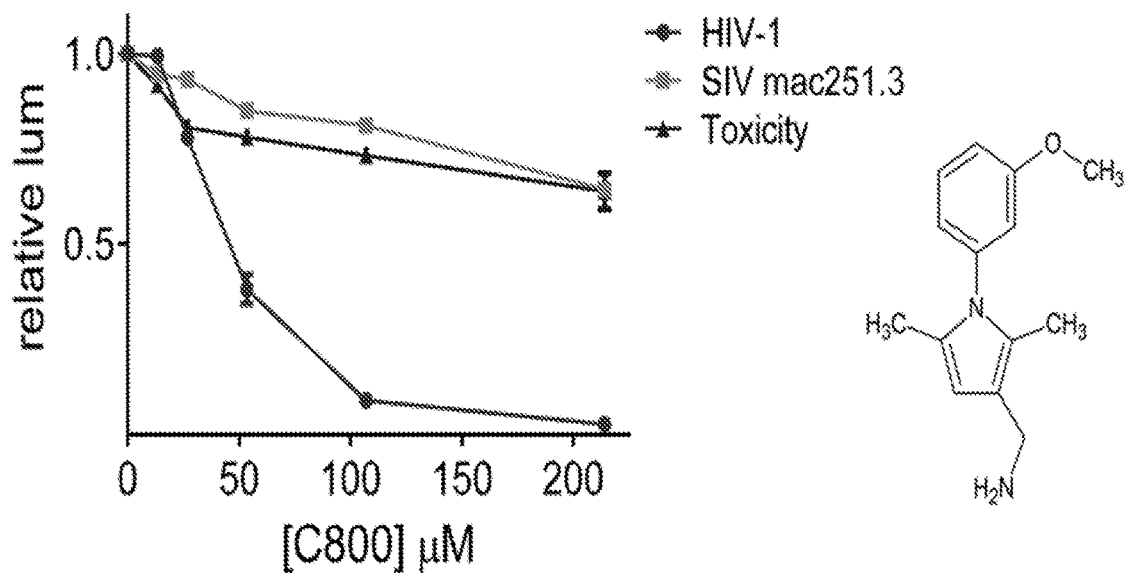

One hit compound, dequalinium (quinolinium,1,1'-(1,10-decanediyl)-bis(4-amino-2-methyl diiodide); (FIG. 5D), is an FDA-approved, antimicrobial drug[34]. It bound gp41-inter with an affinity of 11 µM and showed no binding to 2F5 (FIG. 5C, top), and effectively inhibited cell-cell fusion mediated by HIV-1 Env with an $IC_{50}$ of 13.8 µM, but not by SIV Env (FIG. 5C, bottom). It showed a minimal level of cytotoxicity up to 50 µM within the assay time period (<3 hrs) by an assay measuring ATP concentration, which correlates with the amount of metabolically active cells. Inhibition of HIV-1 infectivity was tested using a luciferase-based virus neutralization assay with Env pseudoviruses in TZM.b1 cells[35-37]. In this assay, which requires incubation for 48 hrs to allow for luciferase reporter gene expression, dequalinium showed more cytotoxicity than in the cell-cell fusion assay. Nevertheless, it exhibited greater inhibition to several HIV-1 isolates than to the murine leukemia virus (MuLV) negative control (FIG. 12A-12B). Furthermore, dequalinium also specifically inhibited cell-cell fusion mediated by Envs of multiple primary HIV-1 isolates of different clades (FIG. 5B), suggesting that it recognizes a conserved binding site.

Structure—Activity Relationship (SAR) Studies of Dequalinium

Dequalinium contains two aminoquinoline head groups connected by a 10 carbon linker. In a pilot SAR study using commercial analogs, two additional dequalinium-like compounds with different head groups were also active in blocking HIV-1 Env mediated cell-cell fusion, while the other two were not (FIG. 8A). The compound, 4-aminoquinaldine, containing only the head group of dequalinium, also showed no activity. It was noted that none of these compounds showed significant cytotoxicity within the tested concentration range. Next, 12 analog compounds were designed and synthesized, modifying the head group of dequalinium or varying the length of the carbon linker or modifying the head group of dequalinium (FIG. 9A, FIG. 9B, and FIG. 13). These compounds were tested for the inhibition activity in the cell-cell fusion assay, as well as their cytotoxicity. Most compounds showed toxicity comparable to that of dequalinium, as indicated by the relative toxicity, with S1C5 being the most toxic one and S2C7 the least toxic (FIG. 8A). Inhibition potency increased with the increasing linker length, but peaked at a length of 12 carbons. Smaller head groups such as S2C9 and S2C11 showed significant decreases in potency, as did the removal of the 2-methyl group (S2C1) and removal of 2-methyl and 4-amine groups (S2C10). Halogenated compounds S2C6, S2C7 and S2C8 showed modestly improved potency as compared to dequalinium. A significant improvement was observed with compound S2C3, which contains the addition of a cyclopentyl group at the 2,3 positions, suggesting that larger hydrophobic groups in these positions enhance the potency.

Binding of S2C3 to gp41-inter was further confirmed by SPR analysis. The compound interacted with gp41-inter with an affinity of 2.0 µM, but showed no binding to 2F5 Fab (FIG. 14A-14D and FIG. 16A-16D). Three selected weak compounds, S1C1, and S2C10, S2C11, from the cell-cell fusion assay, showed very weak binding and no binding to gp41-inter, respectively (FIG. 14A-14D), roughly correlating with their potency in blocking membrane fusion (FIG. 9C). Taken together with the binding data for dequalinium and S2C3, these results indicate that the inhibition efficiency of these compounds against HIV-1 Env mediated membrane fusion of these compounds is primarily determined by their ability to bind their gp41 target. Similarly, improvement in potency of S2C3 as compared to dequalinium was also observed for inhibition of viral infectivity (FIG. 14D). Furthermore, it was confirmed by SPR that S2C3 competed with 2F5 for binding to gp41-inter, but not with a cluster I antibody, 240D Fab, which recognizes an epitope in the C-C loop of gp41[38] (FIG. 16C-16D), suggesting that the MPER remains the target of S2C3. Likewise, improvement of the potency of S2C3 over dequalinium was also observed for inhibition of viral infectivity (FIG. 14D). The inhibitory potency of each selected compound in the virus inhibition assay correlated with that in the cell-cell fusion assay. A similar inhibition profile among selected compounds was also found against several other HIV-1 isolates albeit with reduced potencies (FIG. 17A-17E).

Additional Evidence for the S2C3-MPER Interaction

To gain further insights into the S2C3 binding site on gp41, a chemical shift perturbation study was conducted by titrating an MPER construct with increasing concentrations of S2C3 (FIG. 18A). It was previously reported that an NMR structure of a gp41 fragment containing both the MPER and TMD (transmembrane domain) (residues 660-710) can be reconstituted in bicelles.[41] Using the same MPER-TMD/ bicelle system, a series of 2D TROSY-HSQC spectra were recorded with increasing concentrations of either S2C3 or a DMSO negative control. The most evident S2C3-dependent chemical shift changes were observed in the residues of the MPER, including the backbones of L663, W672 and N677, as well as the side chains of W666, W670 and $R^{683}$ (FIG. 18B and FIG. 18C), suggesting that direct contact of S2C3 to these residues has led to changes of their chemical environment. In addition, the peak intensity of the MPER residues decreased by 40-60% after addition of S2C3, while that of the residues in the TMD (residues 683-698) was not affected (FIG. 19A-19B). These observations imply that S2C3 binding may reduce the backbone dynamics of the MPER. Interestingly, the peak intensity of the C-terminal end of the TMD (residues 699-709) also decreased upon S2C3 addition, probably due to the conformational coupling between the MPER and the C-terminus of TMD observed in the other studies (data not shown).

To further map residues that are in contact with S2C3, 3D $^{15}$N-edited-NOESY spectra were acquired using the ($^{15}$N, $^{13}$C, $^2$H)-labeled MPER-TMD reconstituted in bicelles in the presence or absence of the compound. Under these conditions, only protons of S2C3 and labile protons of the MPER-TMD (backbone and side-chain amide protons) were detected, while non-labile protons of the MPER-TMD (attached to $^{13}$C) were replaced with deuterons and not detected in the NOE experiments. The acyl chains of detergent and lipid were deuterated. To eliminate false positives due to incomplete deuteration of the $^{13}$C sites in the MPER-TMD, the $J_{CH}$-modulated, $^{15}$N-edited NOESY[40] was performed that removes NOEs between $^1$H -$^{15}$N and $^1$H-$^{13}$C spectroscopically. The chemical shifts of S2C3 protons were assigned by comparing its 1D $^1$H spectrum in bicelles with the theoretically predicted one (FIG. 20A-20C). The NOESY strips of the MPER-TMD/S2C3 showed similar patterns of the intra-protein NOE peaks as did the ones without the compound (FIG. 18A, FIG. 21A and FIG. 21B), indicating S2C3 has little impact on those NOEs and the overall protein structure. The NOE correlation peaks were identified between S2C3 protons and the amide protons of the residues of W666, A667, W670, W672, I675 and W680 in the MPER, but not with any residues in the TMD region (FIG. 15A and FIG. 21A-21C). The strongest NOE peaks, from the protons of S2C3 head groups, were observed in the strips of W670 and W672 side chain amide proton (HE) and I675 backbone amide proton (HN). Additional NOEs indicated that the protons of the S2C3 carbon linker were in contact with W6661-HE, A667HN, and W680HE of the MPER (FIG. 15A and FIG. 21A-21C).

A Small-Molecule Binding Pocket Formed by the MPER

Initially, it was observed that there were a similar but a smaller number of NOE peaks between dequalinium and the MPER in the $^{15}$N-edited NOESY spectrum, indicating direct contacts of the compound with residues L663, W666, W670 and W672 (FIG. 22A-22B). A preliminary structure was calculated using these NOEs showing a binding pocket of dequalinium formed by the hydrophobic residues in the MPER (FIG. 15B). Because dequalinium is less soluble in DMSO and has weaker affinity to gp41 than S2C3, we performed further structural studies using S2C3 only.

To define the binding site of S2C3 at the atomic level, the structure of S2C3-bound MPER-TMD was determined using NOE restraints between S2C3 and the MPER, as well as the intra-protein restraints reported previously[40,41]. The final ensemble of structures converged to RMSD of 1.227 Å and 1.766 Å for backbone and all heavy atoms, respectively (FIG. 23 and Table 1). The structure with the lowest energy is shown in FIG. 15B. The two head groups of S2C3 interact with a hydrophobic pocket formed by residues L661, W666, L669, W670, W672, I675, L679 and W680 from two neighboring MPER-TMD protomers (FIG. 15C). One head group of the compound is projecting outward, in contact with W672 and I675 of one MPER protomer. The other head group is inserting into the hydrophobic core of the MPER formed by residues W666, W670 and L661 of the other protomer. The S2C3 carbon linker also makes hydrophobic contacts the side chains of L661, L669 and L679 and contributes to the binding. In addition, the side chain of R683 is also projecting toward the compound, explaining the S2C3 induced chemical shift changes of the side chain amide proton of R683 (HE) (FIG. 18A-18C).

TABLE 1

Statistics of NMR restraints and structure calculation

| NMR distance and dihedral constraints [a] | |
|---|---|
| Distance restraints from NOE [b] | |
| Short-range intra-protomer (∣i-j∣ ≤ 4) | 627 |
| Long-range intra-protomer (∣i-j∣ ≥ 5) | 21 |
| Inter-protomer | 66 |
| Inter-S2C3-protein | 33 |
| Total dihedral angle restraints [b] | 252 |
| Ø (TALOS) | 126 |
| Ψ (TALOS) | 126 |
| Structure statistics [c] | |
| Violations (mean ± s.d.) | |
| Distance constraints (Å) | 0.096 ± 0.006 |
| Dihedral angle constraints (°) | 0.899 ± 0.094 |
| Deviations from idealized geometry | |
| Bond lengths (Å) | 0.011 ± 0.000 |
| Bond angles (°) | 0.946 ± 0.026 |
| Impropers (°) | 0.591 ± 0.031 |
| Average pairwise r.m.s. deviation (Å) [d] | |
| Heavy | 1.766 |
| Backbone | 1.227 |

[a] The numbers of constraints are summed over all three subunits.
[b] The inter-S2C3-protein restraints were obtained from the current study on MPER/TMD in complex with S2C3. The intra-protomer and inter-protomer NOE restraints as well as the dihedral angle restraints were the ones used for the structure calculation of MPER-TMD in the previous study[40].
[c] Statistics are calculated and averaged for an ensemble of the 15 lowest energy structures out of 100 calculated structures.
[d] The precision of the atomic coordinates is defined as the average r.m.s. difference between the 15 final structures and their mean coordinates.

S2C3 (also dequalinium) is a symmetrical molecule. The NOE restraints cannot rule out the possibility that the two head groups of the compound occupy two adjacent binding pockets instead of one. Therefore, the structure was calculated using the same NOE restraints but with an assumption that the two identical head groups of S2C3 make contacts only one MPER protomer. The resulting structures had a much higher energy than the one shown in FIG. 15B-15D because of the increased number of NOE violations, suggesting that one S2C3 molecule primarily, if not exclusively, occupies a single hydrophobic pocket formed by two neighboring MPER protomers. Indeed, the single-pocket binding mode is also consistent with the observation that there is an optimal length of the linker connecting the two head groups for its inhibitory activity (FIG. 9C).

MPER Mutations Affecting Env Sensitivity to S2C3

To validate the NMR structure of the S2C3-MPER complex, several mutants were generated in the context of the full-length 92UG037.8 HIV-1 Env, to alter the hydrophobicity of the binding pocket. S2C3 inhibition of these Env mutants were analyzed in the cell-cell fusion assay in comparison with the wild type Env. All mutants showed a readily detectable level of fusion activity ranging 20-100% of that of the wildtype Env (FIG. 24A). In the presence of S2C3, the single mutant W666A showed an $IC_{50}$ of 9.9 µM, as compared to 4.4 µM for the wild type Env (FIG. 24B and Table 2, below). A triple mutant W666S/L669S/I675S exhibited the greatest resistance to S2C3 with an $IC_{50}$ of 16.7 µM. Moreover, two other mutants, K683A and K683A/$R^{696}A$, became more sensitive to S2C3 than the wildtype Env, suggesting the increased hydrophobicity of the binding pocket may lead to more effective recognition by the compound. As a comparison, a mutant (mTMD) containing multiple changes in the TMD even with reversed hydrophobicity in the region showed no significant difference in S2C3 inhibition from the wild type Env (FIG. 24B and Table 2). These results suggest that the hydrophobicity of the S2C3 binding pocket in the MPER is a useful determinant for the compound inhibition of HIV-1 Env-mediated membrane fusion.

TABLE 2

$IC_{50}$s of HIV-1 Env mutants measured in the cell-cell fusion assay.

| HIV-1 Env | IC50 (µM) |
| --- | --- |
| Wild type | 4.4 ± 0.41 |
| W666S/L669S/I675S | 16.7 ± 2.16 |
| W666A/L669S/I675S | 11.5 ± 1.11 |
| W666A/L669S/I675S/W680S | 14.9 ± 0.75 |
| W666S | 7.8 ± 0.57 |
| W666A/W672K | 7.6 ± 1.24 |
| W666A | 9.9 ± 0.58 |
| K683A | 2.6 ± 0.97 |
| R696A | 2.1 ± 0.23 |
| K683A/R696A | ~0.9 |
| mTMD (L704S/V705S/N706A/V708S/R709A/Q710A) | 5.3 ± 0.21 |

*The data were generated in triplicate from two independent experiments. IC50 values were obtained by fitting to the model [Inhibitor] vs. response - Variable slope provided in GraphPad Prism version 8 for Mac OS (GraphPad Software, La Jolla California USA).

Summary of Experiments

Modern drug discovery is a very time-consuming and increasingly expensive process. Most drug targets involve either an enzyme active site (such as those of HIV-1 reverse transcriptase and protease) or a ligand binding site (such as those of cell receptors). It has also been suggested that all the obvious human "druggable" targets may have been exhausted by conventional approaches, and thus the pharmaceutical industry has begun to shift its focus towards protein-based biologics. There are some limitations of protein-based therapy, however, including high cost for production, inability to penetrate membranes to reach intracellular targets and unwanted immune responses. It is therefore still desirable, for treatment of most diseases, to develop orally available small-molecule drugs.

In this study, a neutralizing monoclonal antibody was used that targeted HIV-1 gp41 to guide the search for leads of novel therapeutics against a nonconventional site—the MPER. Monoclonal antibodies have been used as therapeutics to treat human diseases because they can specifically target functional sites of key proteins in disease-related pathways[48,49]. They too, however, may suffer from drawbacks similar to those of other biologics. As described herein a neutralizing antibody was turned into small-molecule drug leads based on the following considerations. First, interactions between an antibody and its cognate antigen involve hydrophobic interactions, hydrogen bonds and salt bridges, similar to those between a small-molecule drug and its protein target. Second, protein-protein interactions often rely on a small set of contact residues (hot spot) for the majority of binding free energy despite large interfaces[50], suggesting that a small-molecule compound may be sufficient not only to mimic how an inhibitory antibody binds its antigen, but also to compete with it for antigen binding. A small-molecule lead can thus be identified through competition with the antibody for antigen binding and it may mimic the action of the antibody to block or modulate physiological functions of the protein (antigen). Third, effective antibodies often target functionally critical sites (inhibitory or neutralizing epitopes) on a protein of interest, which may not necessarily be an active or ligand-binding site. This general strategy can expand the repertoire of druggable sites on disease-related proteins that are not accessible by conventional approaches.

As a proof of concept for the antibody-based screening strategy to search for promising drug leads or targets, dequalinium and its more potent analog S2C3 were identified as small-molecule fusion inhibitors that effectively block HIV-1 infection. In particular, S2C3 binds a hydrophobic pocket formed exclusively by the residues in the MPER, as revealed by our NMR structure (FIG. 15A-15D). The MPER has long been considered a promising vaccine target because it contains linear epitopes recognized by several well-characterized (bnAbs)[30-32,51]. Previous structural studies have shown that it mainly adopts an a-helical conformation with or without a kink in the middle[40]. One such structure was determined by NMR using a monomeric MPER peptide reconstituted in detergent micelles, which folded into a kinked helix with many hydrophobic residues embedded in the micelles[52,53], leading to a widely-held belief that the MPER should be buried in viral membrane. Nevertheless, none of these structures even hinted that the MPER could form a small-molecule binding site. Recently, our NMR structure of a gp41 construct containing both the MPER and TMD reconstituted in a lipid bilayer revealed that the MPER is not buried in membrane but instead forms a tightly packed trimeric cluster[40]. This new structure most likely represents a prefusion conformation of the MPER in a native Env spike, underscoring the important structural role of the lipid bilayer in maintaining physiologically relevant conformation of Env. Using the same system, the binding pocket in the MPER formed by highly conserved hydrophobic residues was confirmed and demonstrated how a small molecule interacts with this unexpected binding site. It is noteworthy that the HTS campaign started long before the structure determination of the MPER trimer, demonstrating the power of using a neutralizing antibody as a guide for searching novel small-molecule binding sites even in absence of any high-resolution structural information.

Previous studies have indicated that the MPER-TMD in bicelles mainly adopts a conformation that is incompatible with 2F5 binding, but the MPER is conformationally dynamic and transiently samples various conformations, accessible up to ~10% of the time to 2F5[40]. S2C3 probably stabilizes the prefusion conformation of the MPER, driving the conformational equilibrium towards the direction of disfavoring antibody binding and thus blocking 2F5 binding allosterically instead of by direct competition. Indeed, the decreased peak intensity of the MPER residues in the NMR titration experiment observed upon S2C3 addition suggested the reduced conformational dynamics of the MPER in the presence of the compound. Conceivably, this may also be the mechanism by which S2C3-like compounds inhibit HIV-1 infection—by preventing conformational changes of gp41 from the prefusion state to the receptor-triggered fusion intermediate state, required for productive membrane fusion. It is anticipated that these compounds are useful reagents or probes that dissect the functional roles of the MPER during HIV-1 entry.

Dequalinium is the active ingredient of several topical medications, such as DEQUADIN® and FLUOMIZIN®, to treat bacterial infections[54,55], but thes medications have also been tested for the treatment of cancer and malaria[56-59]. The discovery of a small-molecule binding site in the MPER drastically expands the medical relevance of this vaccine target. Finally, the antibody-based screening strategy for drug discovery is contemplated to be applicable to many other human diseases.

Methods

Protein Expression and Purification

Gp41-inter proteins were produced as described previous[24,34]. Briefly, the proteins were overexpressed in Rosetta 2 codon plus cells (Novagen) as inclusion bodies after induction with 1 mM IPTG at 37 °C. for 6 hours. The bacteria cells were lysed by freezing-thawing cycles and sonication; the gp41-inter proteins were purified by acid extraction and refolded by a rapid-dilution protocol as described[24,60], and further purified by gel-filtration chromatography on a prep-grade Superdex 200 (GE Healthcare Life Sciences) in 25 mM Tris-HCl, pH 7.5 and 150 mM NaCl. Purified proteins were concentrated and stored at −80° C.

Anti-HIV-1 Env monoclonal antibodies and their Fab fragments were produced as described[42,61]. 2F5 Fab was labeled with fluorescein isothiocyanate (FITC). Briefly, 2F5 Fab was treated with a 10-fold molar excess of FITC in 50 mM borate, pH 8.5. The reaction was closely monitored by the 280 nm/495 nm absorbance ratio to avoid multiple labeling per Fab. When a single label was achieved (usually in 1 hr at room temperature), the reaction was quenched with sodium azide and free FITC molecules removed by dialysis. The labeled Fab was further purified using gel filtration chromatography.

Production of the MPER-TMD protein containing residues 660-710 from a Glade D HIV-1 isolate 92UG024.2 was carried out as described[40]. Briefly, the protein was expressed as a trpLE fusion in Escherichia coli strain BL21 (DE3) cells using M9 minimal media supplemented with stable isotopes $^{15}$N, $^{13}$C or $^2$H according to the specific labeling requirement for each experiment. The protein was extracted from inclusion bodies, cleaved by cyanogen bromide, purified by Ni-NTA and HPLC, and then reconstituted in DHPC/DMPC bicelles following the previous protocols[40].

High-Throughput Screening and Chemical Synthesis

All screening experiments were carried out at Harvard Medical School ICCB-Longwood Screening Facility. For the screening assay, 10 µl of the gp41-inter protein in phosphate buffered saline (PBS) at a concentration of 180 nM was added to each well of a Corning 384-well low volume microtitre plate using a Multidrop Combi Reagent Dispenser (Thermo Fisher Scientific). 100 nl of each compound dissolved in DMSO with a concentration of ~10 mM was transferred to each well via pin transfer. Plates were gently vortexed for 5 seconds and then incubated for 1 hr at room temperature. After the incubation, 10 µl of FITC-labeled 2F5 Fab (100 nM in PBS) was added using the reagent dispenser, gently vortexed for 5 seconds and incubated for additional 30 min at room temperature. Plates were spun for 1 min prior to fluorescent measurements. For each screening plate, positive controls containing unlabeled 2F5 Fab and negative controls containing DMSO were included and Z'-factors were calculated as a quality control measure. Fluorescent polarization measurements were recorded on a PerkinElmer EnVision plate reader (excitation=480 nm, emission=535 nm, light=100%, number of flashes=50, detector gain=500). All screening was performed in duplicate. During data analysis, any compounds that fluoresce or scatter light, thus interfering with the FP calculation were eliminated. Duplicate values were averaged and those having a Z' score of 5 or greater were selected for further analysis. Compound libraries at the ICCB-Longwood used for this project include the known bioactives collections (total of 9,659 compounds) and a number of commercial libraries (total of 160,127 compounds): Biomol 1, 4 and Biomol ICCBL-2012 (Enzo Life Sciences International, Inc.), Microsource 1, MS Discovery, NINDS Custom Collection (Discover Systems, Inc., Gaylordsville, Conn.), NIH clinical collection 1 and 2, Prestwick2 (Prestwick Chemical Inc), TocriScreen Mini Library (Tocris Bioscience), ActiMol TimTec 1 (Newark, DE), Asinex 1 (Winston-Salem, N.C.), Bionet (Ryan Scientific, Mount Pleasant, S.C.), CEREP (Redmond, Wash.), ChemDiv (San Diego, Calif.), and ChemBridge (San Diego, Calif.), ENAMINE (Ukraine), Life Chemicals (Burlington, ON, Canada), Maybridge (Trevillet, Tintagel, Cornwall, U.K.). We screened 162,106 compounds and 146 compounds met our criteria as "hits", giving a hit rate of 0.09%. The synthesis of dequalinium analogs was conducted at Chemveda Life Sciences Pvt. Ltd., Plot #: B-11/1, IDA, Uppal, Hyderabad-500 039, Telangana, India. All compounds were purified by recrystallization and purity was confirmed by both mass spec and NMR analysis.

Cell-Cell Fusion Assay and Compound Inhibition

The cell-cell fusion assay, based on the α-complementation of E. coli β-galactosidase, was conducted as described previously[62], with minor modifications for analyzing inhibitory potency of small-molecule compounds. Briefly, Env-expressing cells ($1.0 \times 10^6$ cells/ml) were mixed with CD4- and CCR5-expressing cells ($1.0 \times 10^6$ cells/ml). Cell-cell fusion was allowed to proceed at 37° C. for 2 hr. Cell-cell fusion activity was quantified using a chemiluminescent assay system, Gal-Screen (Applied Biosystems, Foster City, Calif.). To analyze small-molecule compounds, Env-expressing cells were first incubated with each of them at various concentrations (10-100 µM) at 37° C. for 20 min before mixing with CD4- and CCR5-expressing cells. Each compound was dissolved in DMSO to produce a 5 mM stock, which was subsequently diluted by 2-fold, 4-fold and 10-fold in DMSO, respectively. 1 µl of each of these compound solutions at different concentrations (0.5-5 mM) was mixed with 50 µl Env-expressing cells to give the final compound concentrations of 10-100 µM. The cells with equal amount of DMSO only were used as a negative control for compound inhibition and all fusion activity values were normalized by the readout of the DMSO control. For analyzing S2C3 inhibition with Env mutants, the final S2C3 concentrations after mixed with Env-expressing cells ranged between 2 and 25 µM, by addition of 1 µl S2C3 solutions at 0.1-1.25 mM to a well of 50 µl Env-expressing cells.

Cytotoxicity Assay

The cytotoxicity assay was performed using the CellTiter-Glo 2.0 kit (Promega) to measure the cell viability (changes in the amount of ATP due to cell death) when exposed to different compounds. Another identical set of Env-expressing cells, CD4- and CCR5-expressing cells and compounds were mixed in parallel when the cell-cell fusion assay was performed, followed by incubation at 37° C. for 2 hr. The cells were cooled to room temperature for 30 min before adding 100 µl of the CellTiter-Glo 2.0 reagent. The mixture was incubated in room temperature in dark for 10 min before recording luminescence using a Synergy Neo microplane reader (BioTek).

Viral Infectivity Assay and Compound Inhibition

Inhibition of HIV-1 infectivity was measured using a luciferase-based viral infectivity assay with Env pseudoviruses in TZM.b1 cells according to a protocol described previously[37,38]. The assay measures the reduction in luciferase reporter gene expression in TZM.b1 cells following a single round of virus infection. All the compounds were dissolved in a sodium acetate buffer (50 mM, pH 4.5) to produce stocks of 0.5 mM. Two-fold serial dilutions of compounds by 10% DMEM growth medium were performed in duplicate in a 96-well plate. The same dilution of the acetate buffer was performed as an empty control. Virus was added to each well, and the plate was incubated for 1 hr at 37° C. TZM.b1 cells ($1\times10^4$/well) in 10% DMEM growth medium containing DEAE-Dextran (Sigma) at a final concentration of 11 μg/ml were then added. Following a 48 hour incubation, luminescence was measured using Bright-Glo luciferase reagent (Promega). Murine leukemia virus (MuLV) was used as a negative control. HIV-1 Env pseudoviruses was prepared as previously describee.

SPR (Surface Plasm on Resonance) Analysis

All experiments were performed with a Biacore 3000 system (GE Healthcare) at 25° C. in HBS-E buffer (10 mM HEPES, pH 7.0, 150 mM NaCl, 3 mM EDTA) containing 0.5% DMSO. Protein immobilization to CM5 chips was performed following the standard amine coupling procedure as recommended by the manufacturer. The immobilization level was 3,000, RU for small-molecule binding experiments unless specified. For S2C3 competition with antibodies for binding to gp41-inter, 2F5 Fab or 240D Fab was immobilized at a level of 1,500, RU. Small molecule compounds were dissolved in DMSO and diluted in the HBS-E buffer by 200-fold, so that the final DMSO concentration matched that in the running buffer. Sensorgrams were recorded by passing various concentrations of an analyte over the immobilized ligand surface at a flow rate of 40 μl/min either with a 2-min association phase followed by a 10-min dissociation phase for binding to gp41-inter surfaces or with a 4-min association phase followed by a 10-min dissociation phase for binding to antibody surfaces. Identical injections over blank surfaces were subtracted from the data for kinetic analysis. Binding kinetics were analyzed by BiaEvaluation software using a 1:1 Langmuir binding model. All injections were carried out in duplicate and gave essentially identical results.

Chemical Shift Perturbation Upon S2C3 Titration

NMR data of chemical shift perturbation were acquired on Bruker spectrometers operating at $^1$H frequency of 600 MHz and equipped with cryogenic probes at 35° C. A series of 2D $^{15}$N TROSY-HSQC spectra were acquired using 350 μl of the $^{15}$N-labeled MPER-TMD/bicelle (0.25 mM) after sequential addition of 52C3 to a final concentration of 0.5 mM, 1.5 mM and 2.5 mM, respectively. Specifically, a TROSY-HSQC spectrum was first acquired without S2C3 as a reference. S2C3 was dissolved in DMSO to make a 50 mM stock solution and it was added to the protein sample stepwise to give a final S2C3 concentration of 0.5 mM, 1.5 mM and 2.5 mM, respectively. At each step, a 2D TROSY-HSQC spectrum of the sample was acquired. As negative controls, TROSY-HSQC spectra were also acquired using the same batch of the MPER-TMD/bicelle sample (350 μl at 0.25 mM) after stepwise addition of equal amount of DMSO that was in the S2C3-added sample at each concentration. NMR data were processed with NMRpipe[63]. The spectra were analyzed using SPARKY (T. D. Goddard and D. G. Kneller, SPARKY 3, University of California, San Francisco). All the parameters were identical for all data acquisition and processing. The chemical shift differences in $^1$H and $^{15}$N were averaged using the following equation to generate the averaged chemical shift difference (FIG. 19A-19B):

$$\delta_{ave} = \sqrt{(0.2\times\delta N + \delta H)/2}$$

The δN stands for the chemical shift difference in the $^{15}$N dimension. The δH stands for the chemical shift difference in the $^1$H dimension.

NMR Structure Determination

To obtain distance restraints between S2C3 and the MPER-TMD, a $^{13}$C-selected, 3D $^{15}$N-edited NOESY-TROSY-HSQC spectrum[40] was acquired at 35° C. on Bruker spectrometers operating at $^1$H frequency of 900 MHz using 0.6 mM $^{15}$N-, $^{13}$C- and $^2$H-labeled MPER-TMD reconstituted in perdeuterated bicelles in the presence of 2 mM S2C3. Perdeuteration was used to eliminate signals from carbon side chains of the MPER-TMD and acyl chains of DMPC/DHPC bicelles. $^{13}$C-$^1$H J-coupling allowed us to remove any residual signals from protein carbon side chains in case deuteration was incomplete[40]. In the NOESY spectrum, only signals from S2C3, protein backbones, side-chain amide groups, head groups of DMPC and DHPC were detectable.

The NMR data were processed and analyzed using NMRpipe[63] and XEASY[64]. The NOESY stripes of the MPER-TMD/S2C3 sample and its 2D TROSY-HSQC spectrum exhibited very similar patterns compared to those from an MPER-TMD sample without S2C3 (FIG. 18A, FIG. 20A and FIG. 20B). Assignment of the amide group resonance was performed based on the assignments published previously[40,62]. Chemical shifts of most residues in the construct had no significant differences between the samples in the presence or absence of S2C3. Assignment of the S2C3 protons was performed based on the predicted $^1$H NMR spectrum of S2C3 generated by the online software available on the world wide web at http://<www.cheminfo.org/Spectra/NMR/Predictions/1H_Prediction/>. Since S2C3 had little impact on NOESY and TROSY-HSQC spectra of the MPER-TMD, we used the inter- and intra-protomer NOE restraints and the dihedral angle restraints from the previously published MPER-TMD structure, together with distance restraints extracted from NOE peaks between S2C3 and the MPER-TMD for structure calculation of the MPER-TMD/S2C3 complex. We assumed that three S2C3 molecules bound with one MPER-TMD trimer and each compound molecule interacted with two neighboring protomers of the protein. 100 structures were generated in total by software XPLOR-NIH[65], and 15 structures with the lowest energies were selected for the final ensemble (FIG. 23).

For the MPER-TMD/dequalinium complex, 3D $^{15}$N-edited NOESY-TROSY-HSQC spectrum was acquired using 0.6 mM $^{15}$N, $^2$H-labeled perdeuterated MPER-TMD reconstituted in perdeuterated bicelles in the presence of 3 mM dequalinium at 35° C. on Bruker spectrometers operating at $^1$H frequency of 800 MHz. Similar procedures of assignment and structure calculation were performed.

EXAMPLE 2, REFERENCES

1. Hammer, S. M. et al. A controlled trial of two nucleoside analogues plus indinavir in persons with human immunodeficiency virus infection and CD4 cell counts of 200 per cubic millimeter or less. AIDS Clinical Trials Group 320 Study Team. The New England journal of medicine 337, 725-733, doi:10.1056/NEJM199709113371101 (1997).

2. Gulick, R. M. et al. Treatment with indinavir, zidovudine, and lamivudine in adults with human immunodeficiency virus infection and prior antiretroviral therapy. The New England journal of medicine 337, 734-739, doi:10.1056/NEJM199709113371102 (1997).
3. Palella, F. J., Jr. et al. Declining morbidity and mortality among patients with advanced human immunodeficiency virus infection. HIV Outpatient Study Investigators. The New England journal of medicine 338, 853-860, doi: 10.1056/NEJM199803263381301 (1998).
4. Grant, M., Samuel, R., Bettiker, R. L. & Suh, B. Antiretroviral therapy 2010 update: current practices and controversies. Arch Pharm Res 34, 1045-1053, doi: 10.1007/s12272-011-0701-3 (2011).
5. Thompson, M. A. et al. Antiretroviral treatment of adult HIV infection: 2012 recommendations of the International Antiviral Society-USA panel. Jama 308, 387-402, doi : 10.1001/j ama.2012.7961 (2012).
6. Kilby, J. M. & Eron, J. J. Novel therapies based on mechanisms of HIV-1 cell entry. N Engl J Med 348, 2228-2238 (2003).
7. Robertson, D. US FDA approves new class of HIV therapeutics. Nat Biotechnol 21, 470-471, doi:10.1038/nbt0503-470 (2003).
8. Poveda, E. et al. Dynamics of enfuvirtide resistance in HIV-infected patients during and after long-term enfuvirtide salvage therapy. J Clin Virol 34, 295-301, doi: 10.1016/j jcv.2005.02.004 (2005).
9. Poveda, E. et al. Evolution of genotypic and phenotypic resistance to Enfuvirtide in HIV-infected patients experiencing prolonged virologic failure. Journal of medical virology 74, 21-28, doi:10.1002/jmv.20141 (2004).
10. Sista, P. R. et al. Characterization of determinants of genotypic and phenotypic resistance to enfuvirtide in baseline and on-treatment HIV-1 isolates. Aids 18, 1787-1794 (2004).
11. He, Y. et al. Design and evaluation of sifuvirtide, a novel HIV-1 fusion inhibitor. The Journal of biological chemistry 283, 11126-11134, doi:10.1074/jbc.M800200200 (2008).
12. Pan, C., Cai, L., Lu, H., Qi, Z. & Jiang, S. Combinations of the first and next generations of human immunodeficiency virus (HIV) fusion inhibitors exhibit a highly potent synergistic effect against enfuvirtide-sensitive and -resistant HIV type 1 strains. Journal of virology 83, 7862-7872, doi:10.1128/JVI.00168-09 (2009).
13. Xie, D. et al. An albumin-conjugated peptide exhibits potent anti-HIV activity and long in vivo half-life. Antimicrob Agents Chemother 54, 191-196, doi:10.1128/AAC.00976-09 (2010).
14. Santos, J. R. et al. Efficacy and safety of switching from enfuvirtide to raltegravir in patients with virological suppression. HIV Clin Trials 10, 432-438, doi:10.1310/hct1006-432 (2009).
15. Harrison, S. C. Mechanism of membrane fusion by viral envelope proteins. Adv Virus Res 64, 231-259 (2005).
16. Harrison, S. C. Viral membrane fusion. Nature structural & molecular biology 15, 690-698, doi:10.1038/nsmb.1456 (2008).
17. Weissenhorn, W., Dessen, A., Harrison, S. C., Skehel, J. J. & Wiley, D. C. Atomic structure of the ectodomain from HIV-1 gp41. Nature 387, 426-430 (1997).
18. Chan, D. C., Fass, D., Berger, J. M. & Kim, P. S. Core structure of gp41 from the HIV envelope glycoprotein. Cell 89, 263-273 (1997).
19. Julien, J. P. et al. Crystal structure of a soluble cleaved HIV-1 envelope trimer. Science 342, 1477-1483, doi: 10.1126/science.1245625 (2013).
20. Lyumkis, D. et al. Cryo-EM structure of a fully glycosylated soluble cleaved HIV-1 envelope trimer. Science 342, 1484-1490, doi:10.1126/science.1245627 (2013).
21. Pancera, M. et al. Structure and immune recognition of trimeric pre-fusion HIV-1 Env. Nature 514, 455-461, doi : 10.1038/nature 13808 (2014).
22. Chan, D. C. & Kim, P. S. HIV entry and its inhibition. Cell 93, 681-684 (1998).
23. Frey, G. et al. A fusion-intermediate state of HIV-1 gp41 targeted by broadly neutralizing antibodies. Proc Natl Acad Sci U S A 105, 3739-3744 (2008).
24. Chen, J. et al. Mechanism of HIV-1 neutralization by antibodies targeting a membrane-proximal region of gp41. Journal of virology 88, 1249-1258, doi:10.1128/JVI.02664-13 (2014).
25. Alam, S. M. et al. Role of HIV membrane in neutralization by two broadly neutralizing antibodies. Proc Natl Acad Sci USA 106, 20234-20239, doi:0908713106 [pii] 10.1073/pnas.0908713106 (2009).
26. Dimitrov, A. S., Rawat, S. S., Jiang, S. & Blumenthal, R. Role of the fusion peptide and membrane-proximal domain in HIV-1 envelope glycoprotein-mediated membrane fusion. Biochemistry 42, 14150-14158 (2003).
27. Munoz-Barroso, I., Salzwedel, K., Hunter, E. & Blumenthal, R. Role of the membrane-proximal domain in the initial stages of human immunodeficiency virus type 1 envelope glycoprotein-mediated membrane fusion. Journal of virology 73, 6089-6092 (1999).
28. Salzwedel, K., West, J. T. & Hunter, E. A conserved tryptophan-rich motif in the membrane-proximal region of the human immunodeficiency virus type 1 gp41 ectodomain is important for Env-mediated fusion and virus infectivity. Journal of virology 73, 2469-2480 (1999).
29. Muster, T. et al. A conserved neutralizing epitope on gp41 of human immunodeficiency virus type 1. J Virol 67, 6642-6647 (1993).
30. Stiegler, G. et al. A potent cross-clade neutralizing human monoclonal antibody against a novel epitope on gp41 of human immunodeficiency virus type 1. AIDS Res Hum Retroviruses 17, 1757-1765 (2001).
31. Huang, J. et al. Broad and potent neutralization of HIV-1 by a gp41-specific human antibody. Nature 491, 406-412, doi: 10.1038/nature 11544 (2012).
32. Trkola, A. et al. Delay of HIV-1 rebound after cessation of antiretroviral therapy through passive transfer of human neutralizing antibodies. Nature medicine 11, 615-622, doi:10.1038/nm1244 (2005).
33. Frey, G. et al. Distinct conformational states of HIV-1 gp41 are recognized by neutralizing and non-neutralizing antibodies. Nature structural & molecular biology 17, 1486-1491, doi:10.1038/nsmb.1950 (2010).
34. Weissenbacher, E. R. et al. A comparison of dequalinium chloride vaginal tablets (Fluomizin(R)) and clindamycin vaginal cream in the treatment of bacterial vaginosis: a single-blind, randomized clinical trial of efficacy and safety. Gynecologic and obstetric investigation 73, 8-15, doi:10.1159/000332398 (2012).
35. Nkolola, J. P. et al. Breadth of neutralizing antibodies elicited by stable, homogeneous Clade A and Clade C HIV-1 gp140 envelope trimers in guinea pigs. Journal of virology 84, 3270-3279, doi:10.1128/JVI.02252-09 (2010).

36. Li, M. et al. Human immunodeficiency virus type 1 env clones from acute and early subtype B infections for standardized assessments of vaccine-elicited neutralizing antibodies. J Virol 79, 10108-10125 (2005).
37. Mascola, J. R. et al. Recommendations for the design and use of standard virus panels to assess neutralizing antibody responses elicited by candidate human immunodeficiency virus type 1 vaccines. J Virol 79, 10103-10107 (2005).
38. Robinson, W. E., Jr. et al. Antibodies to the primary immunodominant domain of human immunodeficiency virus type 1 (HIV-1) glycoprotein gp41 enhance HIV-1 infection in vitro. J Virol 64, 5301-5305 (1990).
39. Clackson, T. & Wells, J. A. A hot spot of binding energy in a hormone-receptor interface. Science 267, 383-386, doi:10.1126/science.7529940 (1995).
40. Liao, Y., Zhang, S. M., Neo, T. L. & Tam, J. P. Tryptophan-dependent membrane interaction and heteromerization with the internal fusion peptide by the membrane proximal external region of SARS-CoV spike protein. Biochemistry 54, 1819-1830, doi:10.1021/bi501352u (2015).
41. Song, L. et al. Broadly neutralizing anti-HIV-1 antibodies disrupt a hinge-related function of gp41 at the membrane interface. Proc Natl Acad Sci U S A 106, 9057-9062, doi:10.1073/pnas.0901474106 (2009).
42. Fu, Q. et al. Structure of the membrane proximal external region of HIV-1 envelope glycoprotein. Proc Natl Acad Sci USA 115, E8892-E8899, doi:10.1073/pnas.1807259115 (2018).
43. Pace, C. N. et al. Contribution of hydrophobic interactions to protein stability. J Mol Biol 408, 514-528, doi: 10.1016/j.jmb.2011.02.053 (2011).
44. Bryson, S., Julien, J. P., Hynes, R. C. & Pai, E. F. Crystallographic definition of the epitope promiscuity of the broadly neutralizing anti-human immunodeficiency virus type 1 antibody 2F5: vaccine design implications. J Virol 83, 11862-11875, doi:10.1128/JVI.01604-09 (2009).
45. Delaglio, F. et al. NMRPipe: a multidimensional spectral processing system based on UNIX pipes. Journal of biomolecular NMR 6, 277-293 (1995).
46. Schwieters, C. D., Kuszewski, J. J., Tjandra, N. & Clore, G. M. The Xplor-NIH NMR molecular structure determination package. Journal of magnetic resonance 160, 65-73 (2003).

What is claimed is:

1. A method of treating a viral infection, the method comprising:
administering to a subject in need thereof an agent that inhibits the membrane proximal external region (MPER) of a viral envelope (Env), wherein the viral infection is a human immunodeficiency virus-1 (HIV-1) infection or a human immunodeficiency virus-2 (HIV-2) infection, wherein the agent that inhibits MPER is S2C3.

2. The method of claim 1, wherein the viral envelope is the HIV-1 or HIV-2 Env.

3. The method of claim 1, wherein inhibiting MPER results in the inhibition of Env fusion to the target cell.

4. The method of claim 1, further comprising, prior to administering, the step of diagnosing a subject as having an HIV-1 or HIV-2 infection, or receiving the results of an assay that diagnoses a subject as having an HIV-1 or HIV-2 infection.

5. The method of claim 1, wherein the HIV-1 or HIV-2 infection is resistant to at least one HIV treatment.

6. The method of claim 5, wherein the HIV-1 infection is resistant to an inhibitor of HIV-1 fusion to a target cell.

7. The method of claim 6, wherein the inhibitor of HIV-1 fusion is Maravirox, Enfuvirtide, Sifuvirtide, or Albuvirtide.

8. The method of claim 6, wherein the target cell is a leukocyte, a lymphocyte, a T cell, or a CD4+T cell.

* * * * *

SEQUENCE LISTING

<160> NUMBER OF SEQ ID NOS: 7

<210> SEQ ID NO 1
<211> LENGTH: 2571
<212> TYPE: DNA
<213> ORGANISM: Human immunodeficiency virus 1

<400> SEQUENCE: 1

```
atgagagtga aggagaaata tcagcacttg tggagatggg ggtggagatg gggcaccatg      60
ctccttggga tgttgatgat ctgtagtgct acagaaaaat tgtgggtcac agtctattat     120
ggggtacctg tgtggaagga agcaaccacc actctatttt gtgcatcaga tgctaaagca     180
tatgatacag aggtacataa tgtttgggcc acacatgcct gtgtacccac agaccccaac     240
ccacaagaag tagtattggt aaatgtgaca gaaaattttta acatgtggaa aaatgacatg     300
gtagaacaga tgcatgagga tataatcagt ttatgggatc aaagcctaaa gccatgtgta     360
aaattaaccc cactctgtgt tagtttaaag tgcactgatt tgaagaatga tactaatacc     420
aatagtagta gcgggagaat gataatggag aaaggagaga taaaaaactg ctctttcaat     480
atcagcacaa gcataagagg taaggtgcag aaagaatatg catttttttta taaacttgat     540 ataataccaa tagataatga tactaccagc tataagttga caagttgtaa cacctcagtc     600
attacacagg cctgtccaaa ggtatccttt gagccaattc ccatacatta ttgtgccccg     660
gctggttttg cgattctaaa atgtaataat aagacgttca atggaacagg accatgtaca     720
aatgtcagca cagtacaatg tacacatgga attaggccag tagtatcaac tcaactgctg     780
ttaaatggca gtctagcaga agaagggta gtaattgat ctgtcaattt cacggacaat     840
gctaaaacca taatagtaca gctgaacaca tctgtagaaa ttaattgtac aagacccaac     900 aacaataca gaaaaagaat ccgtatccag agaggaccag ggagagcatt tgttacaata     960
ggaaaaatag gaaatatgag acaagcacat tgtaacatta gtagagcaaa atggaataac    1020
actttaaaac agatagctag caaattaaga gaacaatttg gaataataa aacaataatc    1080 tttaagcaat cctcaggagg ggacccagaa attgtaacgc acagttttaa ttgtggaggg    1140 gaattttttct actgtaattc aacacaactg tttaatagta cttggtttaa tagtacttgg    1200
```

-continued

```
agtactgaag ggtcaaataa cactgaagga agtgacacaa tcaccctccc atgcagaata    1260
aaacaaatta taaacatgtg gcagaaagta ggaaaagcaa tgtatgcccc tcccatcagt    1320
ggacaaatta gatgttcatc aaatattaca gggctgctat taacaagaga tggtggtaat    1380
agcaacaatg agtccgagat cttcagacct ggaggaggag atatgaggga caattggaga    1440
agtgaattat ataaatataa agtagtaaaa attgaaccat taggagtagc acccaccaag    1500
gcaaagagaa gagtggtgca gagagaaaaa agagcagtgg gaataggagc tttgttcctt    1560
gggttcttgg gagcagcagg aagcactatg ggcgcagcct caatgacgct gacggtacag    1620
gccagacaat tattgtctgg tatagtgcag cagcagaaca atttgctgag ggctattgag    1680
gcgcaacagc atctgttgca actcacagtc tggggcatca agcagctcca ggcaagaatc    1740
ctggctgtgg aaagatacct aaaggatcaa cagctcctgg ggatttgggg ttgctctgga    1800
aaactcattt gcaccactgc tgtgccttgg aatgctagtt ggagtaataa atctctggaa    1860
cagatttgga atcacacgac ctggatggag tgggacagag aaattaacaa ttacacaagc    1920
ttaatacact ccttaattga agaatcgcaa aaccagcaag aaaagaatga acaagaatta    1980
ttggaattag ataaatgggc aagtttgtgg aattggttta acataacaaa ttggctgtgg    2040
tatataaaat tattcataat gatagtagga ggcttggtag gtttaagaat agttttgct    2100 gtactttcta tagtgaatag agttaggcag ggatattcac cattatcgtt tcagacccac    2160
ctcccaaccc cgaggggacc cgacaggccc gaaggaatag aagaagaagg tggagagaga    2220
gacagagaca gatccattcg attagtgaac ggatccttgg cacttatctg ggacgatctg    2280
cggagcctgt gcctcttcag ctaccaccgc ttgagagact tactcttgat tgtaacgagg    2340
attgtggaac ttctgggacg cagggggtgg aagccctca aatattggtg gaatctccta    2400
cagtattgga gtcaggaact aaagaatagt gctgttagct tgctcaatgc cacagccata    2460
gcagtagctg aggggacaga taggttata gaagtagtac aaggagcttg tagagctatt    2520
cgccacatac ctagaagaat aagacagggc ttggaaagga ttttgctata a              2571
```

<210> SEQ ID NO 2
<211> LENGTH: 856
<212> TYPE: PRT
<213> ORGANISM: Human immunodeficiency virus 1

<400> SEQUENCE: 2

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125
```

```
Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
    275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
530                 535                 540

Leu Ser Gly Ile Val Gln Gln Gln Asn Asn Leu Leu Arg Ala Ile Glu
```

```
                545                 550                 555                 560
Ala Gln Gln His Leu Leu Gln Leu Thr Val Trp Gly Ile Lys Gln Leu
                    565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 3
<211> LENGTH: 483
<212> TYPE: PRT
<213> ORGANISM: Human immunodeficiency virus 1

<400> SEQUENCE: 3

Ser Ala Thr Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Val Val Leu Val Asn Val Thr Glu Asn
    50                  55                  60
```

-continued

```
Phe Asn Met Trp Lys Asn Asp Met Val Glu Gln Met His Glu Asp Ile
 65                  70                  75                  80

Ile Ser Leu Trp Asp Gln Ser Leu Lys Pro Cys Val Lys Leu Thr Pro
                 85                  90                  95

Leu Cys Val Ser Leu Lys Cys Thr Asp Leu Lys Asn Asp Thr Asn Thr
                100                 105                 110

Asn Ser Ser Ser Gly Arg Met Ile Met Glu Lys Gly Glu Ile Lys Asn
            115                 120                 125

Cys Ser Phe Asn Ile Ser Thr Ser Ile Arg Gly Lys Val Gln Lys Glu
130                 135                 140

Tyr Ala Phe Phe Tyr Lys Leu Asp Ile Ile Pro Ile Asp Asn Asp Thr
145                 150                 155                 160

Thr Ser Tyr Lys Leu Thr Ser Cys Asn Thr Ser Val Ile Thr Gln Ala
                165                 170                 175

Cys Pro Lys Val Ser Phe Glu Pro Ile Pro Ile His Tyr Cys Ala Pro
                180                 185                 190

Ala Gly Phe Ala Ile Leu Lys Cys Asn Asn Lys Thr Phe Asn Gly Thr
            195                 200                 205

Gly Pro Cys Thr Asn Val Ser Thr Val Gln Cys Thr His Gly Ile Arg
210                 215                 220

Pro Val Val Ser Thr Gln Leu Leu Leu Asn Gly Ser Leu Ala Glu Glu
225                 230                 235                 240

Glu Val Val Ile Arg Ser Val Asn Phe Thr Asp Asn Ala Lys Thr Ile
                245                 250                 255

Ile Val Gln Leu Asn Thr Ser Val Glu Ile Asn Cys Thr Arg Pro Asn
                260                 265                 270

Asn Asn Thr Arg Lys Arg Ile Arg Ile Gln Arg Gly Pro Gly Arg Ala
            275                 280                 285

Phe Val Thr Ile Gly Lys Ile Gly Asn Met Arg Gln Ala His Cys Asn
290                 295                 300

Ile Ser Arg Ala Lys Trp Asn Asn Thr Leu Lys Gln Ile Ala Ser Lys
305                 310                 315                 320

Leu Arg Glu Gln Phe Gly Asn Asn Lys Thr Ile Ile Phe Lys Gln Ser
                325                 330                 335

Ser Gly Gly Asp Pro Glu Ile Val Thr His Ser Phe Asn Cys Gly Gly
            340                 345                 350

Glu Phe Phe Tyr Cys Asn Ser Thr Gln Leu Phe Asn Ser Thr Trp Phe
355                 360                 365

Asn Ser Thr Trp Ser Thr Glu Gly Ser Asn Asn Thr Glu Gly Ser Asp
370                 375                 380

Thr Ile Thr Leu Pro Cys Arg Ile Lys Gln Ile Ile Asn Met Trp Gln
385                 390                 395                 400

Lys Val Gly Lys Ala Met Tyr Ala Pro Pro Ile Ser Gly Gln Ile Arg
                405                 410                 415

Cys Ser Ser Asn Ile Thr Gly Leu Leu Leu Thr Arg Asp Gly Gly Asn
                420                 425                 430

Ser Asn Asn Glu Ser Glu Ile Phe Arg Pro Gly Gly Gly Asp Met Arg
            435                 440                 445

Asp Asn Trp Arg Ser Glu Leu Tyr Lys Tyr Lys Val Val Lys Ile Glu
450                 455                 460

Pro Leu Gly Val Ala Pro Thr Lys Ala Lys Arg Arg Val Val Gln Arg
465                 470                 475                 480

Glu Lys Arg
```

<210> SEQ ID NO 4
<211> LENGTH: 345
<212> TYPE: PRT
<213> ORGANISM: Human immunodeficiency virus 1

<400> SEQUENCE: 4

```
Ala Val Gly Ile Gly Ala Leu Phe Leu Gly Phe Leu Gly Ala Gly
 1               5                  10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
 50                  55                  60

Leu Gln Ala Arg Ile Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn His Thr Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
        195                 200                 205

His Leu Pro Thr Pro Arg Gly Pro Asp Arg Pro Glu Gly Ile Glu Glu
    210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
            260                 265                 270

Leu Leu Gly Arg Arg Gly Trp Glu Ala Leu Lys Tyr Trp Trp Asn Leu
        275                 280                 285

Leu Gln Tyr Trp Ser Gln Glu Leu Lys Asn Ser Ala Val Ser Leu Leu
    290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
            340                 345
```

<210> SEQ ID NO 5
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: L, D, W, Y, I or K
<220> FEATURE:
<221> NAME/KEY: MOD_RES
<222> LOCATION: (5)..(7)
<223> OTHER INFORMATION: L, D, W, Y, I or K
<220> FEATURE:
<221> NAME/KEY: MOD_RES
<222> LOCATION: (9)..(9)
<223> OTHER INFORMATION: L, D, W, Y, I or K
<220> FEATURE:
<221> NAME/KEY: MOD_RES
<222> LOCATION: (11)..(12)
<223> OTHER INFORMATION: L, D, W, Y, I or K
<220> FEATURE:
<221> NAME/KEY: MOD_RES
<222> LOCATION: (14)..(15)
<223> OTHER INFORMATION: L, D, W, Y, I or K

<400> SEQUENCE: 5

Leu Asp Xaa Trp Xaa Xaa Xaa Trp Xaa Trp Xaa Xaa Ile Xaa Xaa Trp
1               5                   10                  15

Leu Trp Tyr Ile Lys
            20

<210> SEQ ID NO 6
<211> LENGTH: 25
<212> TYPE: PRT
<213> ORGANISM: Human immunodeficiency virus 1

<400> SEQUENCE: 6

Asp Leu Leu Glu Leu Asp Lys Trp Ala Ser Leu Trp Asn Trp Phe Asp
1               5                   10                  15

Ile Thr Asn Trp Leu Trp Tyr Ile Arg
            20                  25

<210> SEQ ID NO 7
<211> LENGTH: 25
<212> TYPE: PRT
<213> ORGANISM: Human immunodeficiency virus 1

<400> SEQUENCE: 7

Glu Leu Leu Glu Leu Asp Lys Trp Ala Asn Leu Trp Asn Trp Phe Asp
1               5                   10                  15

Ile Ser Asn Trp Leu Trp Tyr Ile Lys
            20                  25
```